US011384137B2

(12) United States Patent
Diamond et al.

(10) Patent No.: US 11,384,137 B2
(45) Date of Patent: *Jul. 12, 2022

(54) MVA-GH/GL-PC VACCINE DERIVED ANTIBODIES NEUTRALIZING HUMAN CYTOMEGALOVIRUS INFECTIVITY AND METHODS THEREOF

(71) Applicant: CITY OF HOPE, Duarte, CA (US)

(72) Inventors: Don J. Diamond, Glendora, CA (US); Flavia Chiuppesi, Monrovia, CA (US); Felix Wussow, Glendora, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/680,205

(22) Filed: Nov. 11, 2019

(65) Prior Publication Data

US 2020/0157191 A1 May 21, 2020

Related U.S. Application Data

(63) Continuation of application No. 15/917,502, filed on Mar. 9, 2018, now Pat. No. 10,487,139, which is a continuation of application No. PCT/US2016/051167, filed on Sep. 9, 2016.

(60) Provisional application No. 62/216,939, filed on Sep. 10, 2015.

(51) Int. Cl.
| | |
|---|---|
| *C07K 16/08* | (2006.01) |
| *A61K 39/12* | (2006.01) |
| *A61P 31/22* | (2006.01) |
| *C07K 7/06* | (2006.01) |
| *C07K 7/08* | (2006.01) |
| *G01N 33/569* | (2006.01) |
| *A61K 39/00* | (2006.01) |

(52) U.S. Cl.
CPC ............ *C07K 16/088* (2013.01); *A61K 39/12* (2013.01); *A61P 31/22* (2018.01); *C07K 7/06* (2013.01); *C07K 7/08* (2013.01); *G01N 33/56994* (2013.01); *A61K 2039/70* (2013.01); *C07K 2317/24* (2013.01); *C07K 2317/34* (2013.01); *C07K 2317/76* (2013.01); *C12N 2710/16134* (2013.01); *G01N 2333/045* (2013.01); *G01N 2800/26* (2013.01)

(58) Field of Classification Search
CPC .......... C07K 16/088; C07K 7/06; C07K 7/08; C07K 2317/24; C07K 2317/34; C07K 2317/76; C07K 14/005; C07K 14/045; C07K 16/085; A61K 39/12; A61K 2039/70; A61K 39/42; A61K 39/25; A61K 2039/525; A61K 2039/6075; A61K 35/76; A61K 35/763; A61P 31/22; G01N 33/56994; G01N 2333/045; G01N 2800/26; C12N 2710/16134; C12N 7/00; C12N 2710/16122; C12N 2710/16151; C12N 2710/16111

See application file for complete search history.

(56) References Cited

U.S. PATENT DOCUMENTS

| | | | |
|---|---|---|---|
| 2003/0166848 | A1 | 9/2003 | Eaton et al. |
| 2004/0110188 | A1 | 6/2004 | Hahn |
| 2006/0045873 | A1 | 3/2006 | Taira et al. |
| 2006/0229438 | A1 | 10/2006 | Nagaraja et al. |
| 2010/0329980 | A1 | 12/2010 | Kumar et al. |
| 2011/0209246 | A1 | 8/2011 | Kovalic et al. |
| 2012/0076801 | A1 | 3/2012 | Lanzavecchia et al. |
| 2013/0259876 | A1 | 10/2013 | Murphy et al. |
| 2014/0030292 | A1 | 1/2014 | Franti et al. |
| 2014/0193428 | A1 | 7/2014 | Lanzavecchia et al. |

FOREIGN PATENT DOCUMENTS

| | | | |
|---|---|---|---|
| WO | 2014/005959 | A1 | 1/2014 |
| WO | 2014/018117 | A1 | 1/2014 |
| WO | 2014/099908 | A1 | 6/2014 |

OTHER PUBLICATIONS

Loomis RJ, Lilja AE, Monroe J, Balabanis KA, Brito LA, Palladino G, Franti M, Mandi CW, Barnett SW, Mason PW. Vectored co-delivery of human cytomegalovirus gH and gL proteins elicits potent complement-independent neutralizing antibodies. Vaccine. Jan. 30, 2013;31(6):919-26. Epub Dec. 14, 2012. (Year: 2012).*
Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

(Continued)

*Primary Examiner* — Rachel B Gill

(74) *Attorney, Agent, or Firm* — Perkins Coie LLP; Lara J. Dueppen; Yang Tang

(57) ABSTRACT

Vaccine-derived neutralizing antibodies (NAbs) for CMV infections and small peptides which define precise recognition elements of the antigens by the NAbs. The vaccine-derived NAbs may be produced by immunizing a subject with a gH/gL/UL128/UL130/UL131A pentameric glycoprotein complex (gH/gLPC). The vaccine-derived NAbs may have properties similar or identical to those of NAbs induced in a subject naturally infected with CMV. Native and non-native small peptides from UL128 and gH have been defined by mapping epitopes and deriving artificial sequences which are minimal recognition elements of vaccine-derived NAbs. These small peptides can be used to elicit vaccine-derived NAbs that prevent CMV entry into susceptible cell types and protect humans from infection and disease. Multivalent vaccines comprising these small peptides and/or epitopes as well as methods of using the vaccine-derived NAbs and small peptides for treating or preventing CMV infection in a subject are also provided.

4 Claims, 17 Drawing Sheets

Specification includes a Sequence Listing.

(56) References Cited

OTHER PUBLICATIONS

Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. NatCommun. Mar. 30, 2015;6:6714. (Year :2015).*

Sela-Culang I, Kunik V, Ofran Y. The structural basis of antibody-antigen recognition. Front Immunol. Oct. 8, 2013;4:302. (Year: 2013).*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*

Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*

Andreoni, M., et al., "A rapid microneutralization assay for the measurement of neutralizing antibody reactive with human cytomegalovirus," J. Virol. Meth. 23:157-168 (1989).

Bernstein, D. I., et al., "Safety and efficacy of a cytomegalovirus glycoprotein B (gB) vaccine in adolescent girls: A randomized clinical trial," Vaccine 34:313-319 (2016).

Boppana, S. B., et al., "Antiviral antibody responses and intrauterine transmission after primary maternal cytomegalovirus infection," J. Infect. Dis. 171:1115-1121 (1995).

Boppana, S. B., et al., "Inrauterine transmission of cytomegalovirus to infants of women with preconceptional immunity," New Engl. J. Med. 344:1366-1371 (2001).

Bowie, J. U., et al., "Deciphering the message in protein sequences: Tolerance to amino acid substitutions," Science 247:1306-1310 (1990).

Britt, W. J., et al., "Indentification of a 65 000 dalton virion envelope protein of human cytomegalovirus," Virus Res. 4:31-36 (1985).

Britt, W., "Controversies in the natural history of congenital human cytomegalovirus infection: the paradox of infection and disease in offspring of women with immunity prior to pregnancy," Med. Microbiol. Immunol. 204:263-271 (2015).

Buscher, N., et al., "The proteome of human cytomegalovirus virions and dense bodies is conserved across different strains," Med. Microbiol. Immunol. 204:285-293 (2015).

Cannon, M. J., et al., "Washing our hands of the congenital cytomegalovirus disease epidemic," BMC Public Health 5:70 (2005).

Cannon, M. J., et al., "Awareness of and behaviors related to child-to-mother transmission of cytomegalovirus," Prev. Med. 54(5):351-357 (2012).

Chen, Z., et al., "Human monoclonal antibodies targeting the haemagglutinin glycoprotein can neutralize H7N9 influenza virus," Nat. Commun. 6:6714 (2015).

Ciferri, C., et al., "Antigenic characterization of the HCMV gH/gL/gO and pentamer cell entry complexes reveals binding sites for potently neutralizing human antibodies," PLoS Pathog. 11(10):e1005230 (2015).

Ciferri, C., et al., "Structural and biochemical studies of HCMV gH/gL/gO and Pentamer reveal mutually exclusive cell entry complexes," PNAS 112(6):1767-1772 (2015).

Cui, X., et al., "Cytomegalovirus vaccines fail to induce epithelial entry neutralizing antibodies comparable to natural infection," Vaccine 26(45):5760-5766 (2008).

Cui, X., et al., "Antibody inhibition of human cytomegalovirus spread in epithelial cell cultures," J. Virol. Methods 192:44-50 (2013).

Dasari, V., et al., " Recent advances in designing an effective vaccine to prevent cytomegalovirus-associated clinical diseases," Expert Rev. Vaccines 12(6):661-676 (2013).

Davison, A.J., et al. RecName: Full=Uncharacterized protein UL128. UniProtKB/Swiss-Prot: P16837.2. Updatede Nov. 3, 2009.

European Patent Office, partial supplementary European search report dated Mar. 25, 2019 for EP 16845227.4.

Even-Desrumeaux, K., et al., "Affinity determination of biotinylated antibodies by flow cytometry," Methods Mol. Biol. 907:443-449 (2012).

Fields, C., et al., "Creation of recombinant antigen-binding molecules derived from hybridomas secreting specific antibodies," Nat. Protoc. 8(6):1125-1148 (2013).

Fisher, S., et al., "Human cytomegalovirus infection of placental cytotrophoblasts in vitro and in utero: Implications for transmission and pathogenesis," J. Virol. 74(15):6808-6820 (2000).

Fouts, A. E., "Pentameric complex of viral glycoprotein H is the primary target for potent neutralization by a human cytomegalovirus vaccine," J. Virol. 86(13):7444-7447 (2012).

Frank, H. G., et al., "Cell culture models of human trophoblast—Primary culture of trophoblast—A workshop report," Placenta 21(Suppl. A):S120-S122 (2000).

Freed, D. C., et al., "Pentameric complex of viral glycoprotein H is the primary target for potent neutralization by a human cytomegalovirus vaccine," PNAS 110:E4997-E5005 (2013).

Gerna, G., et al., "Human cytomegalovirus serum neutralizing antibodies block virus infection of endothelial/epithelial cells, but not fibroblasts, early during primary infection," J. Gen. Virol. 89:853-865 (2008).

Greenspan, N. S., et al., "Defining epitopes: It's not as easy as it seems," Nat. Biotechnol. 17:936-937 (1999).

Griffiths, P. D., et al., "Cytomegalovirus glycoprotein-B vaccine with MF59 adjuvant in transplant recipients: a phase 2 randomised placebo-controlled trial," Lancet 377:1256-1263 (2011).

Griffiths, P., et al., "Desirability and feasibility of a vaccine against cytomegalovirus," Vaccine 31(Suppl 2):B197-B203 (2013).

Hahn, G., et al., "Human cytomegalovirus UL131-128 genes are indidpensable for virus growth in endothelial cells and virus transfer to leukocytes," J. Virol. 78(18):10023-10033 (2004).

Harrer, E., et al., "Therapeutic vaccination of HIV-1-infected patients on HAART with a recombinant HIV-1 nef-expressing MVA: safety, immunogenicity and influence on viral load during treatment interruption," Antiviral Therapy 10:285-300 (2005).

Jacob, C. L., et al., "Neutralizing antibodies are unable to inhibit direct viral cell-to-cell spread of human cytomegalovirus," Virol. 444:140-147 (2013).

Johnson, E. L., et al., "Placental Hofbauer cells limit HIV-1 replication and potentially offset mother to child transmission (MTCT) by induction of immunoregulatory cytokines," Retrovirol. 9:101 (2012).

Johnson, E. L., et al., "Placental Hofbauer cells assemble and sequester HIV-1 in tetraspanin-positive compartments that are accessible to broadly neutralizing antibodies," J. Int. AIDS Soc. 18:19385 (2015).

Kabanova, A., et al., "Antibody-driven design of a human cytomegalovirus gHgLpUL128L subunit vaccine that selectively elicits potent neutralizing antibodies," PNAS 111(50):17965-17970 (2014).

Kauvar, L. M., et al., "A high-affinity native human antibody neutralizes human cytomegalovirus infection of diverse cell types," Antimicrob. Agents Chemother. 59:1558-1568 (2015).

Kenneson, A., et al., "Review and meta-analysis of the epidemiology of congenital cytomegalovirus (CMV) infection," Rev. Med. Virol. 17:253-276 (2007).

Khanna, R., et al., "Human cytomegalovirus vaccine: time to look for alternative options," TRENDS in Mol. Med. 12(1):26-33 (2006).

Krause, P. R., et al., "Priorities for CMV vaccine development," Vaccine 32(1):4-10 (2013).

Kringelum, J. V., et al., "Structural analysis of B-cell epitopes in antibody:protein complexes," Mol. Immunol. 53:24-34 (2013).

Kussie, P. H., et al., "A single engineered amino acid substitution changes antibody fine specificity," J. Immunol. 152:146-152 (1994).

La Rosa, C., et al., "The immune response to human CMV," Future Virol. 7(3):279-293 (2012).

(56) References Cited

OTHER PUBLICATIONS

Lazzarotto, T., et al., "Diagnosis and prognosis of congenital CMV infection: A case report and review of the literature," Scand. J. Clin. Lab. Invest. 74(Suppl. 244):34-40 (2014).
Li, G., et al., "A viral regulator of glycoprotein complexes contributes to human cytomegalovirus cell tropism," PNAS 112(14):4471-4476 (2015).
Li, Z., et al., "The generation of antibody diversity through somatic hypermutation and class switch recombination," Genes Devel. 18:1-11 (2004).
Li, Z., et al., "The generation of antibody diversity through somatic hypermutation and class switch recombination," Genes Dev. 18:1-11 (2004).
Ludwig, A., et al., "Epidemiological impact and disease burden of congenital cytomegalovirus infection in Europe," Eurosurveillance 14(9):1-7 (2009).
Macagno, A., et al., "Isolation of human monoclonal antibodies that potently neutralize human cytomegalovirus infection by targeting different epitopes on the gH/gL/UL128-131A complex," J. Virol. 84(2):1005-1013 (2010).
Maidji, E., et al., "Maternal antibodies enhance or prevent cytomegalovirus infection in the placenta by neonatal Fc receptor-mediated transcytosis," Am. J. Pathol. 168(4):1210-1226 (2006).
Maldonado-Estrada, J., et al., "Evaluation of cytokeratin 7 as an accurate intracellular marker with which to assess the purity of human placental villous trophoblast cells by flow cytometry," J. Immunol. Meth. 286:21-34 (2004).
Manicklal, S., et al., "The "silent" global burden of congenital cytomegalovirus," Clin. Microbiol. Rev. 26(1):86-102 (2013).
Manoussaka, M. S., et al., "Flow cytometric characterisation of cells of differing densities isolated from human term placentae and enrichment of villous trophoblast cells," Placenta 26:308-318 (2005).
Mateu, M. G., et al., "Non-additive effects of multiple amino acid substitutions on antigen-antibody recognition," Eur. J. Immunol. 22:1385-1389 (1992).
McDonagh, S., et al., "Patterns of human cytomegalovirus infection in term placentas: A preliminary analysis," J. Clin. Virol. 35:210-215 (2006).
Meyer, H., et al., "Mapping of deletions in the genome of the highly attenuated vaccinia virus MVA and their influence on virulence," J. Gen. Virol. 72:1031-1038 (1991).
Ornoy, A., et al., "Fetal effects of primary and secondary cytomegalovirus infection in pregnancy," Reprod. Toxicol. 21:399-409 (2006).
Pass, R. F., "Development and evidence for efficacy of CMV glycoprotein B vaccine with MF59 adjuvant," J. Clin. Virol. 46(Suppl 4):S73-S76 (2009).
Pass, R. F., et al., "Vaccine prevention of maternal cytomegalovirus infection," N. Engl. J. Med. 360(12):1191-1199 (2009).
Pass, R. F., et al., "Mother-to-child transmission of cytomegalovirus and prevention of congenital infection," J. Ped. Infect. Dis. Soc. 3(Suppl 1):S2-S6 (2014).
Pereira, L., et al., "Insights into viral transmission at the uterine-placental interface," Trends in Microbiol. 13(4):164-174 (2005).
Pereira, L., et al., "Cytomegalovirus infection in the human placenta Maternal immunity and developmentally regulated receptors on trophoblasts converge," Curr. Topics in Microbiol. Immunol. 325:383-395 (2008).
Pereira, L., et al., "Intrauterine growth restriction caused by underlying congenital cytomegalovirus infection," J. Infect. Dis. 209:1573-1584 (2014).
Potgens, A. J. G., et al., "Characterization of trophoblast cell isolations by a modified flow cytometry assay," Placenta 22:251-255 (2001).
Raliwel, B., et al., "Activation of peroxisome proliferator-activated receptor gamma by human cytomegalovirus for de novo replication impairs migration and invasiveness of cytotrophoblasts from early placentas," J. Virol. 84(6):2946-2954 (2010).
Revello, M. G., et al., "Human cytomegalovirus tropism for endothelial/epithelial cells: scientific background and clinical implications," Rev. Med. Virol. 20:136-155 (2010).
Ryckman, B. J., et al., "Human cytomegalovirus entry into epithelial and endothelial cells depends on genes UL128 to UL150 and occurs by endocytosis and low-pH fusion," J. Virol. 80(2):710-722 (2006).
Ryckman, B. J., et al., "HCMV gH/gL/UL128-131 interferes with virus entry into epithelial cells: Evidence for cell type-specific receptors," PNAS 105(37):14118-14123 (2008).
Saccoccio, F. M., et al., "Peptides from cytomegalovirus UL130 and UL131 proteins induce high titer antibodies that block viral entry into mucosal epithelial cells," Vaccine 29(15):2705-2711 (2011).
Scrivano, L., et al., "HCMV spread and cell tropism are determined by distinct virus populations," PLoS Pathog. 7(1):e1001256 (2011).
Sela-Culang, I, et al., "The structural basis of antibody-antigen recognition," Front. Immunol. 4:302 (2013).
Singh, H., et al., "Improved method for linear B-cell epitope prediction using antigen's primary sequence," PLoS One 8(5):e62216 (2013).
Sinzger, C., et al., "Cloning and sequencing of a highly productive, endotheliotropic virus strain derived from human cytomegalovirus TB40/E," J. Gen. Virol. 89:359-368 (2008).
Stratton, K. R., et al., Vaccines for the 21st century: A toll for decision making, National Academy Press, Washington, DC (2000).
Tabata, T., et al., "Cytotrophoblasts infected with a pathogenic human cytomegalovirus strain dysregulate celleMatrix and cell-cell adhesion molecules: A quantitative analysis," Placenta 28:527-537 (2007).
Tang, Z., et al., "Isolation of Hofbauer cells from human term placentas with high yield and purity," Am. J. Reprod. Immunol. 66(4):336-348 (2011).
Trincado, D. E., et al., "Highly sensitive detection and localization of maternally acquired human cytomegalovirus in placental tissue by in situ polymerase chain reaction," J. Infect. Dis. 192:650-657 (2005).
United States Patent and Trademark Office, International Search Report and Written Opinion dated Mar. 7, 2017 for PCT/US16/51167.
Urban, M., et al., "The dominant linear neutralizing antibody-binding site of glycoprotein gp86 of human cytomegalovirus is strain specific," J. Virol. 66(3):1303-1311 (1992).
Van Regenmortel, M. H. V., "Immunoinformatics may lead to a reappraisal of the nature of B cell epitopes and of the feasibility of synthetic peptide vaccines," J. Mol. Recog. 19:183-187 (2006).
Vanarsdall, A. L., et al., "Human cytomegalovirus glycoprotein gO complexes with gH/gL, promoting interference with viral entry into human fibroblasts but not entry into epithelial cells," J. Virol. 85(22):11638-11645 (2011).
Vanarsdall, A. L., et al., "Human cytomegalovirus entry into cells," Curr. Opin. Virol. 2(1):37-42 (2012).
Wang, D., et al., "Human cytomegalovirus virion protein complex required for epithelial and endothelial cell tropism," PNAS 102(50):18153-18158 (2005).
Wang, D., et al., "Human cytomegalovirus uses two distinct pathways to enter Yetinal pigmented epithelial cells," PNAS 104(50):20037-20042 (2007).
Wang, Z., et al., "Recombinant modified vaccinia virus ankara expressing a soluble form of glycoprotein B causes durable immunity and neutralizing antibodies against multiple strains of human cytomegalovirus," J. Virol. 78(8):3965-3976 (2004).
Wang, Z., et al., "Modified H5 promoter improves stability of insert genes while maintaining immunogenicity during extended passage of genetically engineered MVA vaccines," Vaccine 28(6):1547 (2010).
Wen, Y., et al., "Human cytomegalovirus gH/gL/UL128/UL130/UL131A complex elicits potently neutralizing antibodies in mice," Vaccine 32:3796-3804 (2014).
Wille, P. T., et al., "A human cytomegalovirus gO-null mutant fails to incorporate gH/gL into the virion envelope and is unable to enter fibroblasts and epithelial and endothelial cells," J. Virol. 84(5):2585-2596 (2010).
Wussow, F., et al., "A vaccine based on the rhesus cytomegalovirus UL128 complex induces broadly neutralizing antibodies in rhesus macaques," J. Virol. 87(3):1322-1332 (2013).

(56) References Cited

OTHER PUBLICATIONS

Wussow, F., et al., "Human cytomegalovirus vaccine based on the envelope gH/gL pentamer complex," PLoS Pathog. 10(11):e1004524 (2014).

Yamamoto-Tabata, T., et al., "Human cytomegalovirus interlukin-10 downregulates metalloproteinase activity and impairs endothelial cell migration and placental cytotrophoblast invasiveness in vitro," J. Virol. 78(6):2831-2840 (2004).

Zhang, C., "Hybridoma technology for the generation of monoclonal antibodies," Meth. Mol. Biol. 901:117-135 (2012).

Zhou, M., et al., "Human cytomegalovirus gH/gL/gO promotes the fusion step of entry into all cell types, whereas gH/gL/UL128-131 broadens virus tropism through a distinct mechanism," J. Virol. 89(17):8999-9009 (2015).

Zydek, M., et al., "HCMV infection of human trophoblast progenitor cells of the placenta is neutralized by a human monoclonal antibody to glycoprotein B and not by antibodies to the pentamer complex," Viruses 6:1346-1364 (2014).

\* cited by examiner

| Name | N-term truncations | |
|------|-------------------|---|
| 40   | KRLDVCRAKMGYMLQ   | SEQ ID NO:186 |
| R14Q | RLDVCRAKMGYMLQ    | SEQ ID NO:187 |
| L13Q | LDVCRAKMGYMLQ     | SEQ ID NO:188 |
| D12Q | DVCRAKMGYMLQ      | SEQ ID NO:189 |
| V11Q | VCRAKMGYMLQ       | SEQ ID NO:190 |
| C10Q | CRAKMGYMLQ        | SEQ ID NO:191 |
| R9Q  | RAKMGYMLQ         | SEQ ID NO:192 |
| A8Q  | AKMGYMLQ          | SEQ ID NO:193 |
| K7Q  | KMGYMLQ           | SEQ ID NO:194 |
| M6Q  | MGYMLQ            | SEQ ID NO:195 |

| Name | C-term truncations | |
|------|-------------------|---|
| 40 | KRLDVCRAKMGYMLQ | SEQ ID NO:186 |
| K14L | KRLDVCRAKMGYML | SEQ ID NO:196 |
| K13M | KRLDVCRAKMGYM | SEQ ID NO:177 |
| K12Y | KRLDVCRAKMGY | SEQ ID NO:197 |
| K11G | KRLDVCRAKMG | SEQ ID NO:198 |
| K10M | KRLDVCRAKM | SEQ ID NO:199 |
| K9K | KRLDVCRAK | SEQ ID NO:200 |
| K8A | KRLDVCRA | SEQ ID NO:201 |
| K7R | KRLDVCR | SEQ ID NO:202 |
| K6C | KRLDVC | SEQ ID NO:203 |

| Name | Alanine scan | |
|---|---|---|
| 1 | ARLDVCRAKMGYM | SEQ ID NO:204 |
| 2 | KALDVCRAKMGYM | SEQ ID NO:205 |
| 3 | KRADVCRAKMGYM | SEQ ID NO:206 |
| 4 | KRLAVCRAKMGYM | SEQ ID NO:207 |
| 5 | KRLDACRAKMGYM | SEQ ID NO:208 |
| 6 | KRLDVARAKMGYM | SEQ ID NO:209 |
| 7 | KRLDVCAAKMGYM | SEQ ID NO:210 |
| 8 | KRLDVCRAKMGYM | SEQ ID NO:177 |
| 9 | KRLDVCRAAMGYM | SEQ ID NO:211 |
| 10 | KRLDVCRAKAGYM | SEQ ID NO:212 |
| 11 | KRLDVCRAKMAYM | SEQ ID NO:213 |
| 12 | KRLDVCRAKMGAM | SEQ ID NO:214 |
| 13 | KRLDVCRAKMGYA | SEQ ID NO:215 |

MVA-GH/GL-PC VACCINE DERIVED ANTIBODIES NEUTRALIZING HUMAN CYTOMEGALOVIRUS INFECTIVITY AND METHODS THEREOF

CROSS-REFERENCE TO RELATED APPLICATIONS

The present application is a continuation of U.S. application Ser. No. 15/917,502, filed Mar. 9, 2018, issuing as U.S. Pat. No. 10,487,139 on Nov. 26, 2019, which is a continuation of International Application No. PCT/US2016/051167, filed Sep. 9, 2016, which claims priority to U.S. Provisional Application No. 62/216,939, filed Sep. 10, 2015, which is incorporated herein by reference in its entirety, including drawings.

STATEMENT OF GOVERNMENT INTEREST

This invention was made with government support under Grant Number R01 AI103960, awarded by the National Institutes of Health. The government has certain rights in the invention.

BACKGROUND

Human cytomegalovirus (HCMV) is the most common infectious cause of permanent births defects worldwide, often resulting in auditory and cognitive abnormalities and in rare cases even in multi-organ failure and death (1-4). Congenital HCMV infection occurs in 0.05 to 1% of all pregnancies, and 10 to 25% of congenitally infected newborns develop long-term developmental disabilities (2-6). Annual incidence of HCMV seropositive (HCMV$^+$) infants at birth range from 35,000 in Brazil to 40,000 in the United States, and 250,000 in India (5). In fact, persistent newborn medical conditions are more frequently associated with congenital HCMV infection than with other well-known childhood diseases such as trisomy 21, spina bifida, or fetal-alcohol syndrome (2, 4, 7-10). Besides its leading role in permanent birth defects, HCMV is also a major cause of morbidity and mortality in hematopoetic stem cell and solid organ transplant recipients (11-13). Based on the societal and financial health burden and in the absence of effective treatment options, HCMV has been assigned as one of the highest priority vaccine targets (14, 15). However, incompletely defined correlates of protection, lack of animal models susceptible to HCMV infection, insufficiently powered vaccine trials, and general unawareness, are a number of obstacles that have hampered the development of an effective and safe HCMV vaccine (16).

High titer and durable neutralizing antibodies (NAbs) that block glycoprotein complex-mediated entry into host cells are thought to be essential to prevent or control congenital HCMV infection. For many decades, HCMV subunit vaccine research has primarily focused on stimulation of NAbs targeting the major essential envelope glycoprotein B (gB), culminating in the encouraging findings obtained with recombinant gB admixed in adjuvant MF59 (17). In phase II clinical trials, gB/MF59 has been shown to reduce viremia and the need for antiviral therapy in solid organ transplant recipients and provide moderate efficacy of 38-50% to prevent primary infection in young women of childbearing age (17-20). These findings have spurred interest to improve vaccine-mediated induction of NAb responses as an approach to improve protective efficacy beyond that observed with gB/MF59.

In recent years it has been recognized that HCMV entry into fibroblasts (FB) and epithelial/endothelial cells (EpC/EnC) occurs by alternate routes of entry that are blocked by NAbs of varying potency and cell-type specificity (21-23). HCMV infection of FB depends on the major essential envelope glycoprotein complexes (gC) gM/gN, gB, and gH/gL (22, 23). In contrast to FB entry, HCMV infection of EpC/EnC requires an additional complex formed by gH/gL, UL128, UL130, and UL131A (PC) (21, 24-26). A third gH/gL complex composed of gH/gL/gO appears necessary for entry into both FB and EpC/EnC, though this remains controversial (27-31). NAbs targeting the major gC block both HCMV entry routes (32); however, NAbs recognizing predominantly conformational epitopes formed by two or more of the UL128/130/131A subunits of the PC are unable to prevent FB entry, though they have potency to interfere with EpC/EnC infection that dramatically exceed that of NAb targeting the major gC (32, 33).

Many vaccine strategies based on either live-attenuated viruses, viral vector systems or purified proteins confirm that the PC is the major target of NAbs blocking HCMV infection of EpC/EnC (33-36). All of these vaccine approaches consistently demonstrate in animal models that the PC has superior immunogenicity to elicit NAbs against EpC/EnC entry compared to PC subunit subsets (gH/gL or UL128/UL130/UL131A) or gB (33-36). These studies also show that vaccine approaches employing the PC are equally or even more effective than gB-based vaccine strategies to induce NAbs blocking FB entry (33, 34, 36). Consequently, PC subunit vaccines elicit high titer EpC/EnC specific NAb responses and less potent NAbs against FB entry, which is consistent with the NAb response induced by HCMV during natural infection (37-39).

Although the mechanisms through which HCMV crosses the placenta are still debated, cytotrophoblasts (CTB) including their syncytial forms and progenitors are thought to be the key mediators involved in all potential HCMV vertical transmission routes (40-44). These cells build a bridge at the fetal-maternal interface and can be efficiently infected by HCMV in vitro and in vivo (10, 43-46). In addition, infection of CTB in early gestation often results in placental developmental abnormalities (44, 46-48). However, NAbs that interfere with HCMV infection of placental cells are only poorly characterized. A recent study has shown that HCMV infection of CTB progenitor cells can be efficiently blocked by NAbs to gB, although NAbs targeting the PC are unable to interfere with CTB progenitor infection (49, 50). Whether PC-specific NAbs are able to prevent infection of differentiating CTB is unknown.

Accordingly, there remains a need to develop highly effective antibodies to neutralize CMV infections, particularly HCMV infections.

SUMMARY

In one aspect, the disclosure provided herein relates to a vaccine-derived neutralizing antibody (NAb) against cytomegalovirus (CMV). In some embodiments, the vaccine-derived NAb is against human CMV (HCMV). The vaccine-derived NAb comprises a variable heavy region comprising a CDR1$_{VH}$ sequence, a CDR2$_{VH}$ sequence, and a CDR3$_{VH}$ sequence; a variable light region comprising a CDR1$_{VL}$ sequence, a CDR2$_{VL}$ sequence, and a CDR3$_{VL}$ sequence; wherein the vaccine-derived NAb is produced in response to a recombinant CMV pentameric complex comprising gH, gL, UL128, UL130, and UL131A ("gH/gL-PC").

In some embodiments, the vaccine-derived NAb is similar or identical to a NAb induced in a subject naturally infected with CMV in one or more properties selected from the group consisting of cell-type specificity, neutralization potency, minimal antigen recognition, and frequency to recognize antigenic sites. In some embodiments, the vaccine-derived NAb prevents cell-to-cell spread of CMV, syncytia formation in epithelial cells, or both. In some embodiments, the vaccine-derived NAb has a positive correlation between neutralizing potency and binding affinity of one or more cell surface subunits of the pentameric complex.

In some embodiments, the vaccine-derived NAb specifically binds one or more linear epitopes on the recombinant CMV pentameric complex. The linear epitope is on UL128 of the recombinant CMV pentameric complex, and the linear epitope on UL128 may comprise an amino acid sequence represented by SEQ ID NO: 177 (KRLDVCRAKMGYM). Alternatively, the linear epitope is on gH of the recombinant CMV pentameric complex, and the vaccine-derived NAb neutralizes CMV infection of epithelial cells but not CMV infection of fibroblasts.

In some embodiments, the vaccine-derived NAb specifically binds one or more conformational epitopes on the recombinant CMV pentameric complex. The vaccine-derived NAb specifically binds to one or more conformational epitopes composed of UL128/UL130/UL131A or UL130/UL131A subunits of the recombinant CMV pentameric complex, and neutralizes CMV infection of epithelial cells, endothelial cells, primary placental cytotrophoblast cells or a combination thereof.

In some embodiments, the vaccine-derived NAb specifically binds to one or more conformational epitopes on gH or gH/gL, and the vaccine-derived NAb prevents CMV infection of fibroblasts, epithelial cells, endothelial cells, cytotrophoblasts or a combination thereof.

In some embodiments, the vaccine-derived NAb has a CDR1$_{VH}$ sequence selected from the group consisting of SEQ ID NOs. 3, 11, 19, 27, 35, 43, 51, 59, 67, 75, 83, 91, 99, 107, 115, 123, 131, 139, 147, 155, 163, 171, and sequences sharing at least 90%, at least 91%, at least 92%, at least 93%, at least 94%, at least 95%, at least 96%, at least 97%, at least 98%, or at least 99% identity to SEQ ID NOs. 3, 11, 19, 27, 35, 43, 51, 59, 67, 75, 83, 91, 99, 107, 115, 123, 131, 139, 147, 155, 163, 171, a CDR2$_{VH}$ sequence selected from the group consisting of SEQ ID NOs. 4, 12, 20, 28, 36, 44, 52, 60, 68, 76, 84, 92, 100, 108, 116, 124, 132, 140, 148, 156, 164, 172, and sequences sharing at least 90%, at least 91%, at least 92%, at least 93%, at least 94%, at least 95%, at least 96%, at least 97%, at least 98%, or at least 99% identity to SEQ ID NOs. 4, 12, 20, 28, 36, 44, 52, 60, 68, 76, 84, 92, 100, 108, 116, 124, 132, 140, 148, 156, 164, 172, and/or a CDR3$_{VH}$ sequence selected from the group consisting of SEQ ID NOs. 5, 13, 21, 29, 37, 45, 53, 61, 69, 77, 85, 93, 101, 109, 117, 125, 133, 141, 149, 157, 165, 173, and sequences sharing at least 90%, at least 91%, at least 92%, at least 93%, at least 94%, at least 95%, at least 96%, at least 97%, at least 98%, or at least 99% identity to SEQ ID NOs. 5, 13, 21, 29, 37, 45, 53, 61, 69, 77, 85, 93, 101, 109, 117, 125, 133, 141, 149, 157, 165, 173.

In some embodiments, the vaccine-derived NAb has a CDR1$_{VL}$ sequence selected from the group consisting of SEQ ID NOs. 6, 14, 22, 30, 38, 46, 54, 62, 70, 78, 86, 94, 102, 110, 118, 126, 134, 142, 150, 158, 166, 174, and sequences sharing at least 90%, at least 91%, at least 92%, at least 93%, at least 94%, at least 95%, at least 96%, at least 97%, at least 98%, or at least 99% identity to SEQ ID NOs. 6, 14, 22, 30, 38, 46, 54, 62, 70, 78, 86, 94, 102, 110, 118, 126, 134, 142, 150, 158, 166, 174, a CDR2$_{VL}$ sequence selected from the group consisting of SEQ ID NOs. 7, 15, 23, 31, 39, 47, 55, 63, 71, 79, 87, 95, 103, 111, 119, 127, 135, 143, 151, 159, 167, 175, and sequences sharing at least 90%, at least 91%, at least 92%, at least 93%, at least 94%, at least 95%, at least 96%, at least 97%, at least 98%, or at least 99% identity to SEQ ID NOs. 7, 15, 23, 31, 39, 47, 55, 63, 71, 79, 87, 95, 103, 111, 119, 127, 135, 143, 151, 159, 167, 175, and/or a CDR3$_{VL}$ sequence is selected from the group consisting of SEQ ID NOs. 8, 16, 24, 32, 40, 48, 56, 64, 72, 80, 88, 96, 104, 112, 120, 128, 136, 144, 152, 160, 168, 176, and sequences sharing at least 90%, at least 91%, at least 92%, at least 93%, at least 94%, at least 95%, at least 96%, at least 97%, at least 98%, or at least 99% identity to SEQ ID NOs. 8, 16, 24, 32, 40, 48, 56, 64, 72, 80, 88, 96, 104, 112, 120, 128, 136, 144, 152, 160, 168, 176.

In a related aspect, the disclosure provided herein relates to a composition for treating or preventing CMV infection comprising the vaccine-derived neutralizing antibody (NAb) against cytomegalovirus (CMV) described above. The composition may further comprise a pharmaceutically acceptable carrier, excipient, diluent, adjuvant, or preservative. Optionally, the NAb is a humanized antibody.

In another aspect, the disclosure provided herein relates to a small peptide comprising a linear epitope on UL128. In some embodiments, the small peptide comprises at least one cysteine residue. In some embodiments, the small peptide may have a size of 10 amino acids, 11 amino acids, 12 amino acids, 13 amino acids, 14 amino acids, 15 amino acids, 16 amino acids, 17 amino acids, or 18 amino acids. In some embodiments, the small peptide comprises an amino acid sequence selected from the group consisting of KRLDVCRAKMGYM (SEQ ID NO: 177), HKRLDVCRAKMGYM (SEQ ID NO: 178), KHKRLDVCRAKMGYM (SEQ ID NO: 179), non-native sequence KRLDVSRAKMGYMC (SEQ ID NO: 180), non-native sequence KHKRLDVSRAKMGYMC (SEQ ID NO: 181), and a sequence which is at least 80%, at least 85%, at least 90%, at least 91%, at least 92%, at least 93%, at least 94%, at least 95%, at least 96%, at least 97%, at least 98%, or at least 99% identical to SEQ ID NOs: 177-181. Also disclosed herein is a vaccine composition comprising one or more of the small peptides. The vaccine composition may be used for treating or preventing CMV infections. In certain embodiments, non-native sequence means that the sequence is artificial and is not found in nature.

In another aspect, the disclosure provided herein relates to a method of producing a vaccine-derived NAb against CMV. The method comprises administering to a subject an effective amount of a recombinant CMV pentameric complex comprising gH, gL, UL128, UL130 and UL131A, deriving hybridomas from the subject, and isolating NAbs from the hybridomas. The subject may be a mammal.

In another aspect, the disclosure provided herein relates to a method of detecting the presence of a CMV antigen in a biological sample or a cell culture comprising contacting the sample or the cell culture with a vaccine-derived neutralizing antibody (NAb) against cytomegalovirus (CMV) described above.

In another aspect, the disclosure provided herein relates to a method of treating or preventing CMV infection in a subject, comprising administering to the subject an effective amount of a composition comprising the vaccine-derived neutralizing antibody (NAb) against cytomegalovirus (CMV) described above.

BRIEF DESCRIPTION OF THE DRAWINGS

FIG. 6A shows NAb EC50 and EpC IC50 values that were plotted, and two-tailed Pearson analysis resulted in a positive correlation (r=0.7432, p=0.014). FIG. 6B shows NAb that were grouped in PC specific NAb (UL) and anti-gH NAb based on their subunit recognition (FIG. 2 and Table 2). No statistically significant difference between the two groups was found using an unpaired t-test (p>0.05). FIG. 6C shows that the same groups as in FIG. 6B were analyzed based on their ARPE-19 IC50 values. As evaluated using an unpaired t-test, neutralizing potency of PC specific NAb was significantly different (p=0.0167) from that of gH NAb.

FIG. 7A shows immunoblot detection of gH expressed from Ad vectors in infected ARPE-19 EpC using vaccine-derived anti-gH NAb and anti-gH antibody AP86. Cells infected with Ad-tet were analyzed for control. Shown is chemiluminescence detection of gH after short (5 minutes) or long (1 hour) exposure of X-ray films to the immunoblot. MEK1/2 detection was performed as loading control. FIG. 7B shows immunoblot detection of gH from HCMV strains Towne (TO), TR, Davis (DA), AD169 (AD) or TB40/E (TB) in infected FB using 18F10 and AP86. Uninfected cells (U) were used as a control. For control, samples were analyzed with anti-pp65 antibody (23-103). Mass markers (kDa) are shown next to each panel.

FIG. 8A shows characterization of primary CTB. FSC vs. SSC dot plot on the left indicates the gated population of CTB analyzed. Histograms represent cytokeratin 7 (center) and vimentin (right) expression of the gated CTB population. FIG. 8B shows results from NAb that were tested for their ability to neutralize TB40/E infection of primary CTB isolated from term placentae. Shown are the IC50 values for each vaccine-derived NAb. CMV-HIG was used as a control. Dotted line indicates the highest antibody concentration used in the assay (50 µg/ml).

FIGS. 10A and 10B: C- and N terminal truncated peptides based on library peptide 40 were used in an ELISA to identify the shortest amino acid sequence needed for binding of NAb 13B5. FIG. 10C: ELISA to compare 13B5 binding to K13M comprising the minimal 13B5 epitope sequence and peptides based on K13M with one (H14M) or two (K15M) additional amino acid residues of UL128 added to the N-terminus. FIG. 10D: Alanine scanning based on peptide K13M to identify amino acid residues involved in 13B5 binding. Bars represent standard deviation of triplicate wells.

FIG. 11A: Peptides based on the 13B5 binding site (K15M, K14CS and K16CS) and peptides containing only partial sequences of the 13B5 binding site (UL128 library peptide 38) were coupled to KLH and tested for binding to 13B5 antibody by ELISA. KLH alone was used as a control. Bars represent standard deviation of triplicate wells. FIGS. 11B and 11C: Balb/c mice (5 animals per group) were immunized three times four weeks apart with KLH-coupled peptides adjuvanted in Freund's adjuvant. FIG. 11B shows peptide-specific binding antibodies in sera of immunized mice were measured via ELISA 1 week before (−1wp1st) and 3 weeks post first, second, and third immunization (3wp1st; 3wp2nd, 3wp3rd) by using the peptides as antigens that were used for the immunization. FIG. 11C shows serum neutralizing antibody titers (NT50) from immunized mice were measured against HCMV TB40/E on ARPE-19 EC using a standard microneutralization assay. Lines in B and C indicate the group mean.

DETAILED DESCRIPTION

I. Vaccine-Derived NAbs

Figure 1:
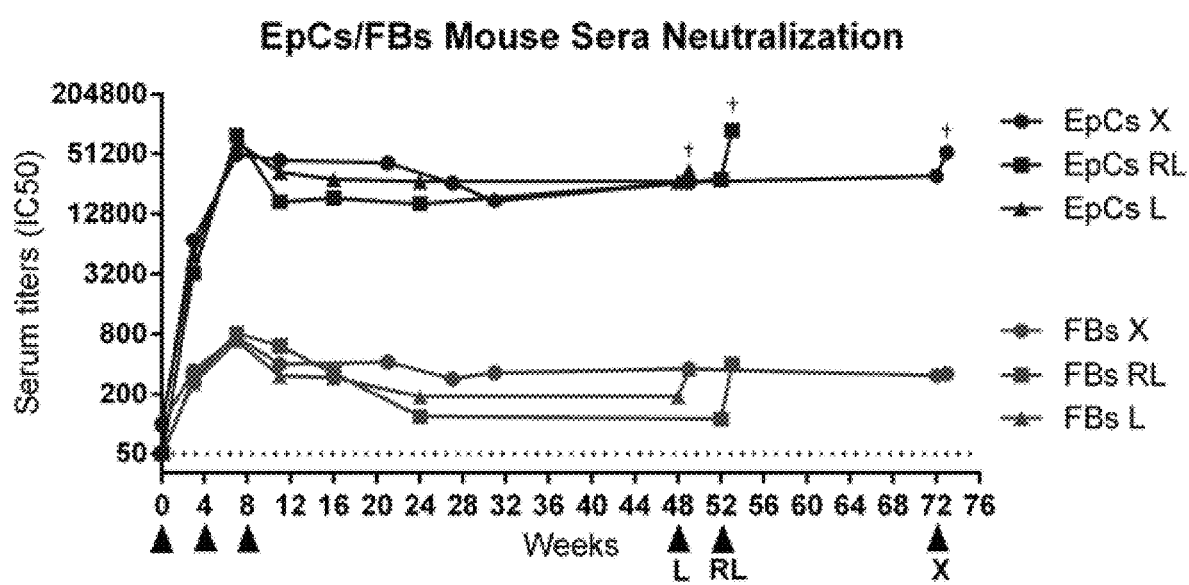
FIG. 1 shows EpC and FBs neutralizing antibody titers on serum samples from immunized mice. Three Balb/C mice (X, RL and L) were vaccinated three times every four weeks by intraperitoneal (i.p.) route with MVA-gH/gL-PC. Mice were boosted with a fourth dose between week 48 and 72 and spleens collected 4 days later for NAbs derivation. HCMV-specific serum NAb titer (IC50) was determined at different time points post-vaccination on EpC (ARPE-19) and FBs (MRC-5) using TB40/E. Arrowheads indicate vaccinations. Vaccinations were performed on all the animals unless indicated under the arrowhead. Crosses represent the time of spleen collection for the different animals. Dotted line indicates the detection limit of the assay.

In one aspect, vaccine-derived neutralizing antibodies (NAbs) against cytomegalovirus (CMV) are provided herein. Human cytomegalovirus (HCMV) elicits neutralizing antibodies (NAbs) of varying potency and cell-type specificity to prevent HCMV entry into fibroblasts (FB) and epithelial/endothelial cells (EpC/EnC). NAbs targeting the major essential envelope glycoprotein complexes gB and gH/gL inhibit both FB and EpC/EnC entry. In contrast to FB infection, HCMV entry into EpC/EnC is additionally blocked by extremely potent NAbs to conformational epitopes of the gH/gL/UL128/UL130/UL131A pentamer complex (PC). A vaccine concept based on the delivery of a membrane tethered-PC by Modified Vaccinia virus Ankara (MVA) (36), a widely used, clinical viral vector platform that has been safely tested in over 120,000 humans (51, 52), was recently developed. This single vector, termed MVA-PC, can co-express all five PC subunits (the gH/gL/UL128/UL130/UL131A pentamer complex, or "gH/gL-PC"). MVA-PC induced high titer and sustained NAbs against EpC/EnC entry in mice and rhesus monkeys and less potent NAbs that blocked FB infection (36), which is consistent with the NAb responses induced by HCMV during natural infection (37-39).

As provided herein, it was unexpectedly discovered that MVA-PC elicits PC- and gH-specific NAbs having properties (such as cell-type specificity, neutralization potency, minimal antigen recognition, and frequency to recognize antigenic sites) similar or identical to previously described NAbs isolated from human HCMV+ patients (32) or NAbs induced in a subject naturally infected with CMV. In addition, vaccine-derived PC-specific NAbs were shown to be significantly more potent than gH-specific NAbs in preventing HCMV spread in EpC and infection of primary cytotrophoblasts (CTBs) from term placentae, suggesting that NAbs recognizing the PC may play an important role in interfering with HCMV vertical transmission.

As used herein, the term "vaccine-derived" antibody means that the antibody is produced by immunizing an animal using a vaccine in contrast to an antibody induced in a subject naturally infected with CMV. For example, an MVA vaccine for delivery of a UL128 complex and preventing CMV infection is described in PCT Publication No. WO 2014/018117 ("the '117 publication"), the content of which is incorporated by reference in its entirety. The vaccine described in the '117 publication, along with other recombinant complexes, may be used herein to immunize the animal from which the NAbs are derived. In certain embodiments, the animal may be a mouse.

As used herein, the term "neutralizing antibody" or "neutralizing antibody against CMV" means that the antibody is capable of preventing or blocking CMV from infecting cells, such as epithelial cells, endothelial cells, primary placental cytotrophoblast cells, fibroblasts, cytotrophoblasts, or a combination thereof, in an animal, preferably in a mammal such as a human. The term can also mean that the antibody is capable of preventing the spread of CMV in cell culture and neutralizing heterologous CMV strains.

The antibodies described herein may be monoclonal antibodies, recombinant antibodies or humanized antibodies.

The vaccine-derived NAbs disclosed herein may comprise a variable heavy region comprising a $CDR1_{VH}$ sequence, a $CDR2_{VH}$ sequence, and a $CDR3_{VH}$ sequence; and a variable light region comprising a $CDR1_{VL}$ sequence, a $CDR2_{VL}$ sequence, and a $CDR3_{VL}$ sequence. Table 1 below lists exemplary vaccine-derived NAbs and their sequences. Also encompassed herein are vaccine-derived NAbs comprising a variable heavy region or a variable light region sharing at least 90% identity to the variable heavy region or the variable light region of the vaccine-derived NAbs disclosed herein, or a combination thereof. In certain embodiments, the vaccine-derived NAbs may comprise a variable heavy region or a variable light region sharing at least 90%, at least 91%, at least 92%, at least 93%, at least 94%, at least 95%, at least 96%, at least 97%, at least 98%, or at least 99% identity to the variable heavy region or the variable light region of the vaccine-derived NAbs disclosed herein or both.

TABLE 1

Sequences of Vaccine-Derived NAbs

| Description | SEQ ID NO | Nucleotide Sequence | SEQ ID NO | Amino Acid Sequence |
|---|---|---|---|---|
| 1B2-VH | 1 | gaagtgcagctggtggagtctgggggaggc ttagtgaagcctggagggtccctgaaactct cctgtgcagcctc<u>tggattcactttcagtgact attac</u>atgtattgggttcgccagactccggaa aagaggctggagtgggtcgcaacc<u>attagt gatgatggtaattacacc</u>aactatccagaca gtgtgaaggggcgattcaccatctccagag acaatgccaagaacaatctttacctgcaaat gagcagtctgaagtctgaggacacagccat gtattactgt<u>gcaagaggatggttactaccag tatttgcttac</u>tggggccaagggactctggtc actgtctctgctg | 89 | EVQLVESGGVLVKP GGSLKLSCAAS<u>GFTF SDYY</u>MWVRQTPEK RLEWVAT<u>ISDDGNYT</u> NYPDSVKGRFTISRD NAKNNLYLQMSSLKS EDTAMYYC<u>ARGWLL PVFAY</u>WGQGTLVTV SA |
| 1B2-VL | 2 | gatattgtgctaactcagtctccagccacct gtctgtgactccaggagatagcgtcagtcttt cctgcagggccagc<u>cagagtattggcaaca acc</u>tacactggtatcaacaaaaatcacatg agtctccaaggcttctcatcaaa<u>tatacttccc</u> agtccatctctggaatccctccaggttcagt ggcagtggatcagggacagatttcactctca atatcaacagtgtggagactgaagattttgg agtgtatttctgt<u>cagcagagtaacagatggc cgtggacg</u>ttcggtggaggcaccaagctgg aaatcaaac | 90 | DIVLTQSPATLSVTPG DSVSLSCRAS<u>QSIGN NLH</u>WYQQKSHESPR LLIK<u>YTSQS</u>ISGIPSRF SGSGSGTDFTLNINS VETEDFGVYFC<u>QQS NRWPWT</u>FGGGTKLE IK |
| 1B2-VH - CDR1 | 3 | ggattcactttcagtgactatta | 91 | GFTFSDYY |
| 1B2-VH - CDR2 | 4 | attagtgatgatggtaattacacc | 92 | ISDDGNYT |

TABLE 1-continued

Sequences of Vaccine-Derived NAbs

| Description | Nucleotide Sequences SEQ ID NO | Sequence | Amino Acid Sequences SEQ ID NO | Sequence |
|---|---|---|---|---|
| 1B2-VH - CDR3 | 5 | gcaagaggatggttactaccagtatttgcttact | 93 | ARGWLLPVFAY |
| 1B2-VL - CDR1 | 6 | cagagtattggcaacaac | 94 | QSIGNN |
| 1B2-VL - CDR2 | 7 | tatacttcc | 95 | YTS |
| 1B2-VL - CDR3 | 8 | cagcagagtaacagatggccgtggacg | 96 | QQSNRWPWT |
| 54E11-VH | 9 | cagatccagttggtgcagtctggacctgagc tgaagaagcctggagagacagtcaagatct cctgcaaggcttctggatataccttcacaagc tatggaatgaactgggtgaagcaggctcca ggaaagggtttaaagtggatgggctggata aacacctacactggagagccaacatatgct gatgacttcaagggacggtttgccttctctttg gaaacctctgccagcactgcctatttacagat caacaacctcaaaaatgaggacacggcta catatttctgtgcaagagaacattactacggt attaaccccctttaggctgctggggccaagg caccactctcacagtctcctcag | 97 | QIQLVQSGPELKKPG ETVKISCKASGYTFT SYGMNWVKQAPGK GLKWMGWINTYTGE PTYADDFKGRFAFSL ETSASTAYLQINNLK NEDTATYFCAREHYY GINPLLGCWGQGTTL TVSS |
| 54E11-VL | 10 | gatatccagatgacacagactacatcctccc tgtctgcctctctgggagacagagtcaccatc agttgcagtgcaagtcagggcattagcaatt atttaaactggtatcagcagaaaccagatgg aactgttaaactcctgatctatgacacatcaa gtttacactcaggagtcccatcaaggttcagt ggcagtgggtctgggacagattattctctcac aatcagcaacctggaacctgaagatattgc cacttactattgtcagcagtatagtaagcttcc ttacacgttcggaggggggaccaagctgga aataaaac | 98 | DIQMTQTTSSLSASL GDRVTISCSASQGIS NYLNWYQQKPDGTV KLLIYDTSSLHSGVPS RFSGSGSGTDYSLTI SNLEPEDIATYYCQQ YSKLPYTFGGGTKLE IK |
| 54E11-VH - CDR1 | 11 | ggatataccttcacaagctatgga | 99 | GYTFTSYG |
| 54E11-VH - CDR2 | 12 | ataaacacctacactggagagcca | 100 | INTYTGEP |
| 54E11-VH - CDR3 | 13 | gcaagagaacattactacggtattaaccccc ttttaggctgc | 101 | AREHYYGINPLLGC |
| 54E11-VL- CDR1 | 14 | cagggcattagcaattat | 102 | QGISNY |
| 54E11-VL- CDR2 | 15 | gacacatca | 103 | DTS |
| 54E11-VL - CDR3 | 16 | cagcagtatagtaagcttccttacacg | 104 | QQYSKLPYT |
| 21F6-VH | 17 | cagatccagttggtgcagtctggacctgagc tgaagaagcctggagagacagtcaagatct cctgcaaggcttctggatataccttcacaagc tatggaatgaactgggtgaagcaggctcca ggaaagggtttaaagtggatgggctggata aacacctacactggagagccaacatatgct gatgacttcaagggacggtttgccttctctttg gaaacctctgccagcactgcctatttacagat caacaacctcaaaaatgaggacacggcta catatttctgtgcaagagaacattactacggt attaaccccctttaggctgctggggccaagg caccactctcacagtctcctcag | 105 | QIQLVQSGPELKKPG ETVKISCKASGYTFT SYGMNWVKQAPGK GLKWMGWINTYTGE PTYADDFKGRFAFSL ETSASTAYLQINNLK NEDTATYFCAREHYY GINPLLGCWGQGTTL TVSS |
| 21F6-VL | 18 | gatatccagatgacacagactacatcctccc tgtctgcctctctgggagacagagtcaccatc agttgcagtgcaagtcagggcattagcaatt atttaaactggtatcagcagaaaccagatgg aactgttaaactcctgatctatgacacatcaa | 106 | DIQMTQTTSSLSASL GDRVTISCSASQGIS NYLNWYQQKPDGTV KLLIYDTSSLHSGVPS RFSGSGSGTDYSLTI |

TABLE 1-continued

Sequences of Vaccine-Derived NAbs

| Description | SEQ ID NO | Nucleotide Sequence | SEQ ID NO | Amino Acid Sequence |
|---|---|---|---|---|
| | | gtttacactcaggagtcccatcaaggttcagt ggcagtgggtctgggacagattattctctcac aatcagcaacctggaacctgaagatattgc cacttactattgt<u>cagcagtatagtaagcttcc ttacacg</u>ttcggagggggaccaagctgga aataaaac | | SNLEPEDIATYYC<u>QQ YSKLPYT</u>FGGGTKLE IK |
| 21F6-VH-CDR1 | 19 | ggatataccttcacaagctatgga | 107 | GYTFTSYG |
| 21F6-VH-CDR2 | 20 | ataaacacctacactggagagcca | 108 | INTYTGEP |
| 21F6-VH-CDR3 | 21 | gcaagagaacattactacggtattaacccc ttttaggctgc | 109 | AREHYYGINPLLGC |
| 21F6-VL-CDR1 | 22 | cagggcattagcaattat | 110 | QGISNY |
| 21F6-VL-CDR2 | 23 | gacacatca | 111 | DTS |
| 21F6-VL-CDR3 | 24 | cagcagtatagtaagcttccttacacg | 112 | QQYSKLPYT |
| 12E2-VH | 25 | gaagtgaagctggtggagtctggggagg cttagtgcagcctggagggtccctgaaactct cctgtgcaacctct<u>ggattcactttcagtgact attac</u>atgttttgggttcgccagactccagag aagaagctggagtgggtcgcatac<u>attagta atggtggtggtagcacc</u>tattatccagacact gtaaagggccgattcaccatctccagagac aatgacaagaacaccctatacctgcaaatg agtcgtctgaagtctgacgacacagccttgt attactgt<u>gtaagaccgaaacgggactttca atacctctatgctatggactac</u>tggggtcaag gaacctcagtcaccgtctcctcag | 113 | EVKLVESGGGLVQP GGSLKLSCATS<u>GFTF SDYY</u>MFWVRQTPEK KLEWVAY<u>ISNGGGST YY</u>PDTVKGRFTISRD NDKNTLYLQMSRLKS DDTALYYC<u>VRPKRDF QYLYAMDY</u>WGQGTS VTVSS |
| 12E2-VL | 26 | gacattgtgctgacacagtctcctgcttccta gctgtatctctggggcagagggccaccatct catgcagggccagc<u>aaaagtgtcagtacat ctggctatagttat</u>atgcactggtaccaacag aaaccaggacagtcacccaaactcctcatc tat<u>cttgcatcc</u>aacctagaatctggggtccct gccaggttcagtggcagtgggtctgggaca gacttcaccctcaacatccatcctgtggagg acgaggatgctgcaacctattactgt<u>cagca cagtagggagcttccgtggacg</u>ttcggtgga ggcaccaagctggaaatcaaac | 114 | DIVLTQSPASLAVSL GQRATISCRAS<u>KSVS TSGYSYMH</u>WYQQKP GQSPKLLIY<u>LASNLES</u> GVPARFSGSGSGTD FTLNIHPVEDEDAAT YYC<u>QHSRELPWT</u>FG GGTKLEIK |
| 12E2-VH-CDR1 | 27 | ggattcactttcagtgactattac | 115 | GFTFSDYY |
| 12E2-VH-CDR2 | 28 | attagtaatggtggtggtagcacc | 116 | ISNGGGST |
| 12E2-VH-CDR3 | 29 | gtaagaccgaaacgggactttcaatacctct atgctatggactac | 117 | VRPKRDFQYLYAMD Y |
| 12E2-VL-CDR1 | 30 | aaaagtgtcagtacatctggctatagttat | 118 | <u>KSVSTSGYSY</u> |
| 12E2-VL-CDR2 | 31 | cttgcatcc | 119 | <u>LAS</u> |
| 12E2-VL-CDR3 | 32 | cagcacagtagggagcttccgtggacg | 120 | <u>QHSRELPVVT</u> |
| 13B5-VH | 33 | caggttactctgaaagagtctggccctggga tattgaagccctcacagaccctcagtctgact tgttctttctctgggttttcactgaccacttctggtt tgggtgtaggctggattcgtcagccttcaggg aagggtctggagtggctggcacac<u>atttggt gggatgatgataaa</u>tactttaacccatccctg | 121 | QVTLKESGPGILKPS QTLSLTCSFS<u>GFSLT TSGLGVG</u>WIRQPSG KGLEWLAH<u>IWWDDD KYFNPSLR</u>NQLTISK DTSRNQVFLEITSVTT |

TABLE 1-continued

Sequences of Vaccine-Derived NAbs

| Description | Nucleotide Sequences SEQ ID NO | Sequence | Amino Acid Sequences SEQ ID NO | Sequence |
|---|---|---|---|---|
|  |  | aggaaccagctcacaatctccaaggatacc tccagaaaccaggtattcctcgagatcacca gtgtgaccactgcagatactgccacttactac tgt<u>gttcgaagcctttatgattacgacgaggg gtactactttgactcc</u>ggggccaaggcacc actctcacagtctcctcag |  | ADTATYYC<u>VRSLYDY DEGYYFDS</u>WGQGTT LTVSS |
| 13B5-VL | 34 | gacattgtgatgactcagtctccagccaccct gtctgtgaatccaggagatagagtctctctct cctgcagggccagc<u>cagagtattagcgact ac</u>ttacactggtatcaacaaaaatcacatga gtctccaaggcttctcatcaaa<u>tacgcttccc</u> aatccatctctgggatccctccaggttcagt ggcagtggatcagggtcagatttcactctca gtatcaacagtgtggaacctgaagatgttgg agtgtattattgt<u>caaaatggtcacaccttt cctccgacg</u>ttcggtggaggcaccaagctgga aatcaaac | 122 | EIVMIQSPATLSVNPG DRVSLSCRAS<u>QSISD YLH</u>WYQQKSHESPR LLIK<u>YAS</u>QSISGIPSR FSGSGSGSDFTLSIN SVEPEDVGVYYC<u>QN GHTFPPT</u>FGGGTKLE IK |
| 13B5-VH-CDR1 | 35 | gggttttcactgaccacttctggtttgggt | 123 | <u>GFSLTTSGLG</u> |
| 13B5-VH-CDR2 | 36 | atttggtgggatgatgataaa | 124 | <u>IWWDDDK</u> |
| 13B5-VH-CDR3 | 37 | gttcgaagcctttatgattacgacgaggggta ctactttgactcc | 125 | <u>VRSLYDYDEGYYFDS</u> |
| 13B5-VL-CDR1 | 38 | cagagtattagcgactac | 126 | <u>QSISDY</u> |
| 13B5-VL-CDR2 | 39 | <u>tacgcttcc</u> | 127 | <u>YAS</u> |
| 13B5-VL-CDR3 | 40 | caaaatggtcacacctttcctccgacg | 128 | <u>QNGHTFPPT</u> |
| 18F10-VH | 41 | cagattactcagaaagagtctggccctggg atattgcagcctcccagaccctcagtctgac ttgttctttctct<u>gggttttcactgagcacttatgg tatagga</u>ataggctggattcgtcagccttcag ggaagggtctggagtggctggcacac<u>atttg gtggaatgataataag</u>aactataacacagc cctgaagagccggctcacaatctccaaggga tccctccaacaaccaggtattcctcaagatc gccagtgtggacactgcagatactgccacat acttctgt<u>gctcgaactgggtacttcgatgtct</u> ggggcgcagggaccacggtcaccgtctcct cag | 129 | QVTLKESGPGILQPS QTLSLTCSFS<u>GFSLS TYGIG</u>IWIRQPSGK GLEWLAH<u>IWWNDNK NYN</u>TALKSRLTISKDP SNNQVFLKIASVDTA DTATYFC<u>ARTGYFDV</u> WGAGTTVTVSS |
| 18F10-VL | 42 | gatgttgtgatgacccaaactccactctccct gcctgtcagtcttggagatcaagtctccatttct tgcagctctagt<u>cagagccttgtgcacagta atggaaacacctat</u>atacattggtacctgca gaaaccaggccagtctccaaagctcctgat ctac<u>acagtttcc</u>aaccgattttctggggtccc agacaggttcagtggcagtggatcagggac agatttcacactcaagatcagcagagtgga ggctgaggatctgggactttatttctgc<u>tctca aagtacacatgttccgtacacg</u>ttcggaggg gggaccaagctggaaataaaac | 130 | DVVLTQTPLSLPVSL GDQVSISCSSS<u>QSLV HSNGNTY</u>IHWYLQKP GQSPKLLIY<u>TVS</u>NRF SGVPDRFSGSGSGT DFTLKISRVEAEDLGL YFC<u>SQSTHVPYT</u>FG GGTKLEIK |
| 18F10-VH-CDR1 | 43 | gggttttcactgagcacttatggtatagga | 131 | <u>GFSLSTYGIG</u> |
| 18F10-VH-CDR2 | 44 | atttggtggaatgataataag | 132 | <u>IWWNDNK</u> |
| 18F10-VH-CDR3 | 45 | gctcgaactgggtacttcgatgtc | 133 | <u>ARTGYFDV</u> |
| 18F10-VL-CDR1 | 46 | cagagccttgtgcacagtaatggaaacacc tat | 134 | <u>QSLVHSNGNTY</u> |

TABLE 1-continued

Sequences of Vaccine-Derived NAbs

| Description | Nucleotide Sequences SEQ ID NO | Sequence | Amino Acid Sequences SEQ ID NO | Sequence |
|---|---|---|---|---|
| 18F10-VL-CDR2 | 47 | acagtttcc | 135 | TVS |
| 18F10-VL-CDR3 | 48 | tctcaaagtacacatgttccgtacacg | 136 | SQSTHVPYT |
| 21E9-VH | 49 | cagatccagttggtgcagtctggacctgagc tgaagaagcctggagagacagtcaagatct cctgcaaggcttctgggtataccttcacaatct atggaatgaactgggtgaagcaggctccag gaaagggtttaaagtggatgggctggataa acacctacactggagagccaacatatgctg atgacttcaggggacggtttgccttctctttgg aaacctctgccagcactgcctatttgcagatc aacaaccctcaaaaatgaggacacggctac atatttctgtgcaagaaaggggtactacggta gtagcgggtactttgactactggggccaagg caccactctcacagtctcctcag | 137 | QIQLVQSGPELKKPG ETVKISCKASGYTFTI YGMNWVKQAPGKGL KWMGWINTYTGEPT YADDFRGRFAFSLET SASTAYLQINNLKNE DTATYFCARKGYYG SSGYFDYWGQGTTL TVSS |
| 21E9-VL | 50 | agtattgtgatgacccagactcccaaattcct gcttgtatcagcaggagacagggttaccata acctgcaaggccagtcagagtgtgagtaat gatgtatcttggtaccaacagaagccagggg cagtctcctaaactgctgatatactatgcgtcc aatcgctacactggagtccctgatcgcttcac tggcagtggatatgggacggatttcactttca ccatcagcactgtgcaggctgaagacctgg cagtttatttctgtcagcaggattatagctctcc gtggacgttcggtggaggcaccaagctgga aatcaaac | 138 | SIVMTQTPKFLLVSA GDRVTITCKASQSVS NDVSWYQQKPGQSP KLLIYYASNRYTGVP DRFTGSGYGTDFTFT ISTVQAEDLAVYFCQ QDYSSPWTFGGGTK LEIK |
| 21E9-VH-CDR1 | 51 | gggtataccttcacaatctatgga | 139 | GYTFTIYG |
| 21E9-VH-CDR2 | 52 | ataaacacctacactggagagcca | 140 | INTYTGEP |
| 21E9-VH-CDR3 | 53 | gcaagaaaggggtactacggtagtagcgg gtactttgactac | 141 | ARKGYYGSSGYFDY |
| 21E9-VL-CDR1 | 54 | cagagtgtgagtaatgat | 142 | QSVSND |
| 21E9-VL-CDR2 | 55 | tatgcgtcc | 143 | YAS |
| 21E9-VL-CDR3 | 56 | cagcaggattatagctctccgtggacg | 144 | QQDYSSPWT |
| 4A3-VH | 57 | caggtccaactgcagcagcctggggctgag ctggtgaggcctggggcttcagtgaaactgt cctgcaaggcttctggctacaccttcaccatct actggatgaactgggtgaagcagaggcctg gacaaggccttgaatggattggtatgattgat ccttcactacacttgaaactcactacaatcaga tgttcaaggacaaggccacattgactgtaga caaatcctccagcactgcctacatgcagctc agcagcctgacatctgaggactctgcggtct attactgtgcaagttctgggacggggcttac tggggccaagggactctgctcactgtctctgc ag | 145 | QVQLQQPGPELVRP GASVKLSCKASGYTF TIYWMNWVKQRPGQ GLEWIGMIDPSDSET HYNQMFKDKATLTV DKSSSTAYMQLSSLT SEDSAVYYCASSGT GAYWGQGTLLTVSA |
| 4A3-VL | 58 | gatgttgtgatgacccagactccactcactttg tcggttaccattggacaaccagcctccatctc ttgcaagtcaagtcagagcctcttagatagtg atggaaagacatatttgaattggttgttacag aggccaggccagtctccaaagcgcctgatc tatttggtgtctaaactggactctggagtccct gacaggttcactctggcagtggatcagggaca gatttcacactgaaaatcagcagattggaag ctgaggatttgggagtttattattgctggcaag gtacacatttccgtacacgttcggaggggg gaccaagctggaaataaaac | 146 | DVVMTQTPLTLSVTI GQPASISCKSSQSLL DSDGKTYLNWLLQR PGQSPKRLIYLVSKL DSGVPDRFTGSGSG TDFTLKISRLEAEDLG VYYCWQGTHFPYTF GGGTKLEIK |

TABLE 1-continued

Sequences of Vaccine-Derived NAbs

| | Nucleotide Sequences | | Amino Acid Sequences | |
|---|---|---|---|---|
| Description | SEQ ID NO | Sequence | SEQ ID NO | Sequence |
| 4A3-VH-CDR1 | 59 | ggctacaccttcaccatctactgg | 147 | GYTFTIYW |
| 4A3-VH-CDR2 | 60 | attgatccttcagacagtgaaact | 148 | IDPSDSET |
| 4A3-VH-CDR3 | 61 | gcaagttctgggacggggcttac | 149 | ASSGTGAY |
| 4A3-VL-CDR1 | 62 | cagagcctcttagatagtgatggaaagacatat | 150 | QSLLDSDGKTY |
| 4A3-VL-CDR2 | 63 | ttggtgtct | 151 | LVS |
| 4A3-VL-CDR3 | 64 | tggcaaggtacacattttccgtacacg | 152 | WQGTHFPYT |
| 62-11-VH | 65 | caggtccaactgcagcagcctggggctgagctggtgaggcctggggcttcagtgaagctgtcctgcaaggcttctggctacaccttcaccagctactggatgaactgggtgaagcagaggcctggacaaggccttgaatggattggtatgattgatccttcactacagtgaaactcactacaatcaaatgttcaaggacaaggccacattgactgtagacaaatcctccagcacagcctacatgcaactcagcagcctgacatctgaggactctgcggtctattactgttcaaatggttactcctcctttgcttactggggccaagggactctggtcactgtctctgtag | 153 | QVQLQQPGAELVRPGASVKLSCKASGYTFTSYWMNWVKQRPGQGLEWIGMIDPSDSETHYNQMFKDKATLTVDKSSSTAYMQLSSLTSEDSAVYYCSNGYSSFAYWGQGTLVTVSV |
| 62-11-VL | 66 | gatgtccagatgacacagactacatcctcccctgtctgcctctctgggagacagagtcaccatcagttgcagtgcaagtcagggcattagcaattatttaaactggtatcagcagaaaccagatggaactgttaaactcctgatctatgacacatcaagtttacactcaggagtcccatcaaggttcagtggcagtgggtctgggacagattattctctcacaatcagcaacctggaacctgaagatattgccacttactattgtcagcagtatagtaagcttccctacacgttcggaggggggaccaagctggaaataaaac | 154 | DVQMTQTTSSLSASLGDRVTISCSASQGISNYLNWYQQKPDGTVKLLIYDTSSLHSGVPSRFSGSGSGTDYSLTISNLEPEDIATYYCQQYSKLPYTFGGGTKLEIK |
| 62-11-VH-CDR1 | 67 | ggctacaccttcaccactctactgg | 155 | GYTFTSYW |
| 62-11-VH-CDR2 | 68 | attgatccttcactacacttgaaact | 156 | IDPSDSET |
| 62-11-VH-CDR3 | 69 | tcaaatggttactcctcctttgcttac | 157 | SNGYSSFAY |
| 62-11-VL-CDR1 | 70 | cagggcattagcaattat | 158 | QGISNY |
| 62-11-VL-CDR2 | 71 | gacacatca | 159 | DTS |
| 62-11-VL-CDR3 | 72 | cagcagtatagtaagcttccctacacg | 160 | QQYSKLPYT |
| 62-100-VH | 73 | caggtccaactgcagcagcctggggctgagctggtgaggcctggggcttcagtgaagctgtcctgcaaggcttctggctacaccttcaccagctactggatgaactgggtgaagcagaggcctggacaaggccttgaatggattggtatgattgatccttcactacagtgaaactcactacaatcaaatgttcaaggacaaggccacattgactgtagacaaatcctccagcacagcctacatgcaactcagcagcctgacatctgaggactctgcggtctattactgttcaaatggttactcctcctttgcttactggggccaagggactctggtcactgtctctgtag | 161 | QVQLQQPGAELVRPGASVKLSCKASGYTFTSYWMNWVKQRPGQGLEWIGMIDPSDSETHYNQMFKDKATLTVDKSSSTAYMQLSSLTSEDSAVYYCSNGYSSFAYWGQGTLVTVSV |

TABLE 1-continued

Sequences of Vaccine-Derived NAbs

| | Nucleotide Sequences | | Amino Acid Sequences | |
|---|---|---|---|---|
| Description | SEQ ID NO | Sequence | SEQ ID NO | Sequence |
| 62-100-VL | 74 | gatattgtgctaactcagtctccagccaccct gtctgtgactccaggagatagcgtcagtcttt cctgcagggccagc<u>caaagtattagcaaca ac</u>ctacactggtatcaacaaaaatcacatg agtctccaaggcttctcatcaag<u>tatgcttcc c</u>agtccatctctgggatcccctccaggttcagt ggcagtggatcagggacagatttcactctca gtatcaacagtgtggagactgaagattttgg aaagtatgtctgt<u>caacagagtaacagctgg ccactcacg</u>ttcggctcggggacaaagttgg aaataaaac | 162 | DIVLTQSPATLSVTPG DSVSLSCRAS<u>QSISN NLH</u>WYQQKSHESPR LLIK<u>YAS</u>QSISGIPSR FSGSGSGTDFTLSIN SVETEDFGKYVC<u>QQ SNSWPLT</u>FGSGTKLE IK |
| 62-100-VH-CDR1 | 75 | <u>ggctacaccttcaccactctactgg</u> | 163 | <u>GYTFTSYW</u> |
| 62-100-VH-CDR2 | 76 | <u>attgatccttcactacacttgaaact</u> | 164 | <u>IDPSDSET</u> |
| 62-100-VH-CDR3 | 77 | <u>tcaaatggttactcctcctttgcttac</u> | 165 | <u>SNGYSSFAY</u> |
| 62-100-VL-CDR1 | 78 | <u>caaagtattagcaacaac</u> | 166 | <u>QSISNN</u> |
| 62-100-VL-CDR2 | 79 | <u>tatgcttcc</u> | 167 | <u>YAS</u> |
| 62-100-VL-CDR3 | 80 | <u>caacagagtaacagctggccactcacg</u> | 168 | <u>QQSNSWPLT</u> |
| 2-80-VH | 81 | cagatccagttggtgcagtctggacctgagc tgaagaagcctggagagacagtcaagatct cctgcaaggcttct<u>ggatataccttcacaaac tttgga</u>atgaactgggtgaagcaggctccag gaaagggtttaaagtggatgggctg<u>gataa acacctacactggagagcca</u>acatatgctg atgacttcaaggacggtttgccttctctttgg aaacctctgccagcactgcctctttgcagatc aacaacctcaaaaatgaggacacggctac atatttctgt<u>gcaagaaggggggatggcctct attctatggactact</u>ggggtcaaggaacctc agtcaccgtctcctcag | 169 | QIQLVQSGPELKKPG ETVKISCKAS<u>GYTFT NFG</u>MNWVKQAPGK GLKWMG<u>WINTYTGE PT</u>YADDFKGRFAFSL ETSASTASLQINNLK NEDTATYFC<u>ARRGD GLYSMDY</u>WGQGTSV TVSS |
| 2-80-VL | 82 | gacattgtgctgacccaatctccagcttctttg gctgtgtctctggggcagagggccaccatat cctgcagagccagt<u>gaaagtattgatagttat ggcaatagtttt</u>atgtactggtaccagcagaa accaggacagccaccccaaactcctcatctat <u>cgtgcatcc</u>aacctagaatctgggatccctg ccaggttcagtggcagtgggtctaggacag acttcaccctcaccattaatcctgtggaggct gatgatgttgcaacctattactgt<u>cagcaaag taatgaggatcctctcacg</u>ttcggtgctggga ccaagctggagctgaaac | 170 | DIVLTQSPASLAVSL GQRATISCRAS<u>ESID SYGNSF</u>MYWYQQKP GQPPKLLIY<u>RAS</u>NLE SGIPARFSGSGSRTD FTLTINPVEADDVATY YC<u>QQSNEDPLT</u>FGA GTKLELK |
| 2-80-VH-CDR1 | 83 | <u>ggatataccttcacaaactttgga</u> | 171 | <u>GYTFTNFG</u> |
| 2-80-VH-CDR2 | 84 | <u>ataaacacctacactggagagcca</u> | 172 | <u>INTYTGEP</u> |
| 2-80-VH-CDR3 | 85 | <u>gcaagaaggggggatggcctctattctatgg actac</u> | 173 | <u>ARRGDGLYSMDY</u> |
| 2-80-VL-CDR1 | 86 | <u>gaaagtattgatagttatggcaatagtttt</u> | 174 | <u>ESIDSYGNSF</u> |
| 2-80-VL-CDR2 | 87 | <u>cgtgcatcc</u> | 175 | <u>RAS</u> |
| 2-80-VL-CDR3 | 88 | <u>cagcaaagtaatgaggatcctctcacg</u> | 176 | <u>QQSNEDPLT</u> |

In some embodiments, the vaccine-derived NAbs disclosed herein such as 1B2, 54E11, 21F6, 12E2, 13B5 and 4A3 are potent NAbs that are able to neutralize HCMV infection of epithelial cells, endothelial cells and primary placental cytotrophoblast cells at picomolar concentrations. These NAbs also prevent the spread of the virus in cell culture and neutralize heterologous HCMV strains with the same potency. Some PC-specific NAbs, such as 1B2, 54E11, 21F6, 12E2, and 4A3, specifically bind to conformational epitopes composed of UL128/UL130/UL131A or UL130/UL131A subunits of the gH/gL-PC. Some PC-specific NAbs such as 13B5 bind a linear epitope on UL128.

In other embodiments, the NAbs disclosed herein such as 21E9, 62-11, 62-100, 2-80, 13B1, 6G2, 10G6, and 25H10 specifically bind to conformational epitopes on gH and prevent HCMV infection of fibroblasts, epithelial cells, endothelial cells and cytotrophoblasts with similar potency, even if less efficiently that the PC-specific NAbs targeting the UL subunits. Some NAbs, such as 18F10, bind to a linear epitope on gH and neutralize CMV infection of epithelial cells but not CMV infection of fibroblasts with potency comparable to other gH NAbs. All the NAbs tested showed binding affinity for the gH/gL-PC in the high nanomolar to low picomolar range.

In some embodiments, the vaccine-derived NAbs disclosed herein potently interfere with HCMV cell-to-cell spread and/or syncytia formation in EpC. Previous reports have shown that CMV-HIG, which represents a pooled IgG antibody repertoire from over 1,000 HCMV$^+$ individuals, potently prevents EpC spread of different HCMV strains (72). In contrast, Jacob et al. have shown that CMV-HIG and monoclonal NAb targeting gB, gH, or the PC are unable to prevent HCMV spread in EpC. However, Jacob et al. investigated spread inhibition in the presence of only very low antibody concentration (76). As disclosed herein, about 1,000-fold higher amounts of the vaccine-derived NAbs than that used by the prior art were shown to be effective in preventing HCMV cell-to-cell spread and/or syncytia formation in EpC of heterologous HCMV strains (Table 3). In addition, the vaccine-derived PC-specific NAbs disclosed herein were significantly more potent than the anti-gH NAbs disclosed herein or CMV-HIG to interfere with EpC spreading of HCMV. Hence, PC-specific NAbs induced by MVA-PC not only confer potent inhibition of HCMV entry, but also have potent ability to prevent HCMV spread and/or syncytia formation in EpC, suggesting that the anti-PC NAbs elicited by MVA-PC can limit cell-associated virus dissemination throughout the human host and transmission to the fetus.

In some embodiments, the vaccine-derived NAbs disclosed herein demonstrate a positive correlation between antibody neutralizing potency and binding affinity of PC- and gH-specific NAbs recognizing cell surface PC. However, in contrast to the difference in neutralization potency of the vaccine-derived PC-specific NAbs and anti-gH NAbs disclosed herein, the difference in binding affinity between these two groups of NAbs was not significant. It is possible that the significant difference in neutralization potency between PC-specific NAbs and NAbs targeting gH/gL (or gB) may reflect the relative low amount of the UL128/130/131A subunits in HCMV virions compared to gH/gL. Hence, much lower antibody concentrations are required to interfere with PC-mediated entry than with the fusion function of gH/gL (77). In contrast, the difference in neutralizing potency of individual NAbs targeting the UL128/130/131A subunits of the PC may be a function of their binding affinity.

II. Small Peptides Comprising Epitopes for Vaccine-Derived NAbs

Two of the isolated NAbs, 13B5 and 18F10, showed recognition of linear epitopes on UL128 and gH respectively. No linear epitope on UL128 with neutralizing properties has been described in the prior art, thus the small peptides disclosed herein can represent the epitope as a surrogate for the whole gH/gL-PC in a peptide vaccine setting. In some embodiments, the small peptide comprises at least one cysteine residue such that a disulfide bridge between UL128 and gL can be formed. In some embodiments, the small peptide may have a size of 10 amino acids, 11 amino acids, 12 amino acids, 13 amino acids, 14 amino acids, 15 amino acids, 16 amino acids, 17 amino acids or 18 amino acids. Other examples include non-native derivatives of SEQ ID NO: 177, e.g. SEQ ID NOs: 180 and 181.

Figure 10A:
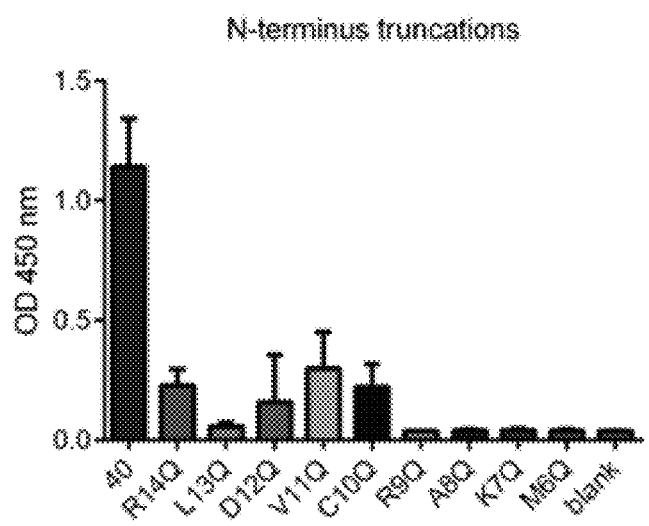
FIGS. 10A-10D show results of studies related to the mapping of the NAb 13B5 minimal binding site.
Figure 10B:
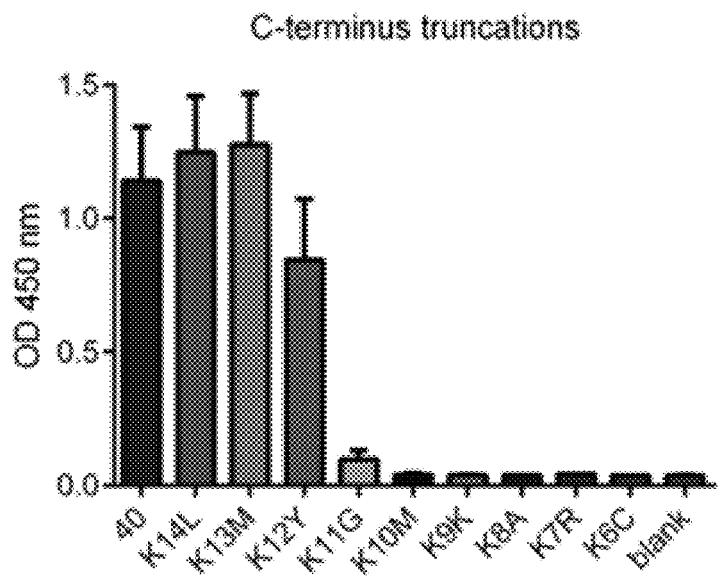
Figure 10C:
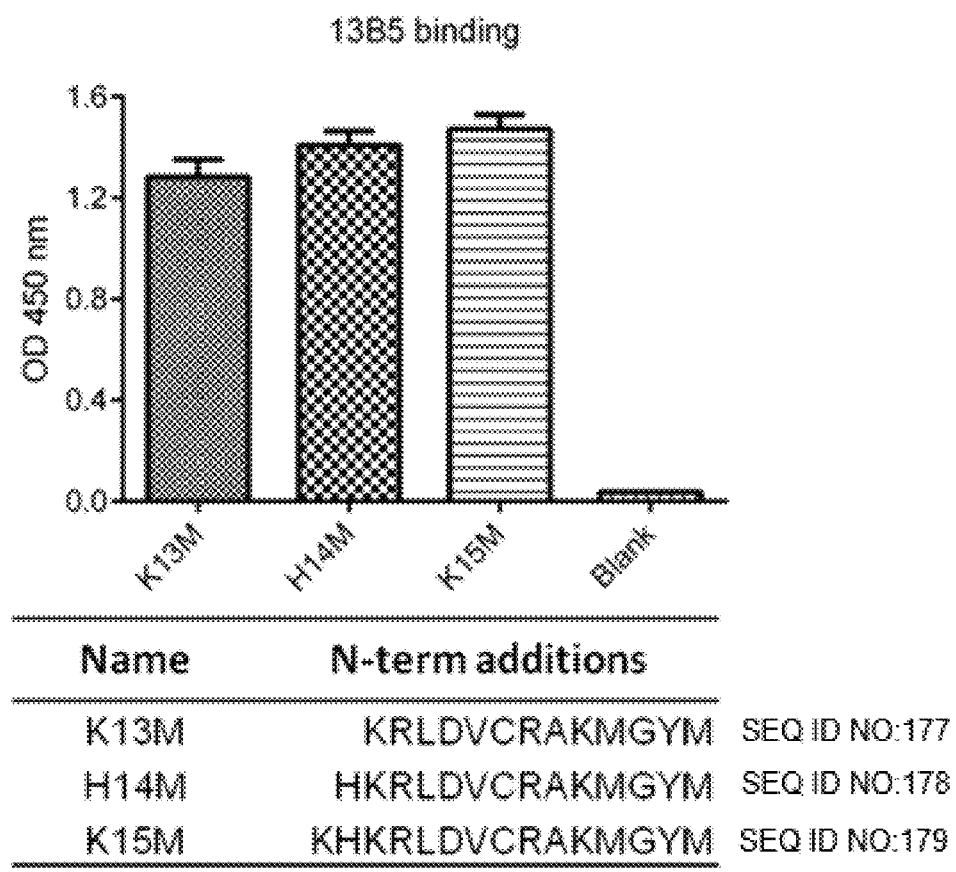

By using 13B5 to bind to a UL128 peptide library in an ELISA assay, peptide K13M (KRLDVCRAKMGYM) (SEQ ID NO: 177) was identified as the minimum sequence required to have a strong binding of the NAb (FIGS. 10A-10B). Moreover, the longer peptides H14M (HKRLDVCRAKMGYM) (SEQ ID NO: 178) and K15M (KHKRLDVCRAKMGYM) (SEQ ID NO: 179) were efficiently recognized by 13B5 (FIG. 10C). The cysteine (Cys-162) residue centrally located in the recognized peptides has been indicated as the amino acid responsible for the disulfide bridge between UL128 and gL thus connecting gH/gL to the UL subunits. The involvement of Cys-162 in 13B5 binding to K13M was evaluated. When a new peptide in which Cys-162 was substituted with serine (K13MS, KRLDVSRAKMGYM) (SEQ ID NO: 182) was tested, 13B5 binding was not detected. When Cys was added to the end of peptide K13MS (i.e., K14CS, KRLDVSRAKMGYMC) (SEQ ID NO: 180)), 13B5 binding was completely restored. It was unexpected that the addition of a cysteine to the 3' end of peptide K13MS (SEQ ID NO: 182) to form peptide K14CS (i.e., SEQ ID NO: 180) would completely restore binding to 13B5 since no binding was detected with K13MS. Similarly, 13B5 binding is detected when Cys was added to the end of K15M and the Cys-162 substituted with serine (i.e., K16CS, KHKRLDVSRAKMGYMC) (SEQ ID NO:181), The small peptides comprising one or more linear epitopes on the gH/gL-PC disclosed herein can be used as peptide vaccines. In some embodiments, K15M (KHKRLDVCRAKMGYM, SEQ ID NO: 179), K14CS (KRLDVSRAKMGYMC, SEQ ID NO: 180), and K16CS (KHKRLDVSRAKMGYMC, SEQ ID NO:181) can be used as peptide vaccines. Upon administration to a subject, a peptide vaccine stimulates antibody production that is specific for CMV antigens on the surface of virus-infected cells or other cells that have incorporated the protein through various processing mechanisms. A peptide vaccine uses one or more small peptides as antigens to elicit an immune response. In order to induce PC specific NAbs the peptides can be coupled to a carrier protein such as Keyhole Limpet Hemocyanin (KLH), Tetanus and diphtheria toxoids (TT and DT respectively), Hepatitis B surface antigen (HBsAg). For example, in some embodiments, KLH-K15M (KLH-coupled SEQ ID NO: 179), KLH-K14CS (KLH-coupled SEQ ID NO: 180), or KLH-K16CS (KLH-coupled SEQ ID NO:181) can be used to elicit an immune response. Given the peptides low immunogenicity in vivo, adjuvants can be added. The peptide vaccine may further comprise one or more adjuvants to boost the immune response. Possible adjuvants include Freud's Complete and Incomplete (CFA, IFA), squalene-based oil-in-water nano-emulsions (MF59, AddaVax), aluminum hydroxide suspensions (Alum, Alhydrogel), toll like receptor agonists (monophosphoryl lipid A), pathogen associated molecular pattern (PAMP) agonists, and damage associated molecular pattern (DAMP) agonists. Other adjuvants in use are so-called oil-in-water emulsions, saponin, LPS, quil-A, Montanide, RIBI, and others that are known in the field. Emulsification of a peptide or peptides in the adjuvant is used as a subcutaneous injection that has benefits for protection against pathogens both in humans and in veterinary applications.

It is desirable to develop effective peptide vaccines due to the ease and low cost for synthesizing small peptides, the effectiveness of the peptide vaccines in inducing immune response, and improved clinical safety in general. Peptides are synthetic molecules which are not live or propagating and have an overwhelming safety advantage. They can be produced using standard clinical manufacturing techniques to high precision and purity. They can be freeze-dried and transported easily and in that condition, avoid the necessity for cold chain. In regards to their specificity, because of the short sequence that defines the peptide vaccine disclosed herein, it has inherent specificity in regards to having limited sequence for the immune system to recognize and process to generate off-target antibodies or T cell responses. Other salutary benefits of peptide vaccines include the possibility of developing a multi-valent formula that is specific for different antigens or different key locations in an antigen that can cause the development of unique and non-overlapping neutralizing antibodies that can aid in protection against a pathogen.

In some embodiments, the small peptides can be administered to a subject, either alone or in combination with one or more adjuvants, to elicit an immune response against CMV infection of the subject. In some embodiments, the small peptides can be administered to a subject such as a mammal to produce NAbs against CMV. In certain embodiments, a method of producing NAbs against CMV may include administering a first dose of one or more small peptides to a subject and administering a second dose of one or more small peptides to the subject after administration of the first dose. In certain embodiments, the second dose may be administered to the subject about one week, about two weeks, about three weeks, about four weeks, or about five weeks after administration of the first dose. In certain embodiments, at least one of the first and second doses includes administering one or more small peptides, at least one of which is selected from SEQ ID NOs: 179, 180, and 181. In certain embodiments, the first dose includes administering one or more small peptides, at least one of which is selected from SEQ ID NOs: 179, 180, and 181. In certain embodiments, the first dose includes administering SEQ ID NO:179, SEQ ID NO: 180, or SEQ ID NO:181 and the second dose includes administering SEQ ID NO:179, SEQ ID NO: 180, or SEQ ID NO:181. In certain embodiments, the first and second doses include administering SEQ ID NO:179, SEQ ID NO: 180, or SEQ ID NO:181. Any combination of SEQ ID NOS 179, 180, and 181 may be used for the first and second doses. For example, the first dose and the second dose comprise at least one of SEQ ID NOS 179, 180, or 181, as shown in the table below:

| First Dose comprises: | Second Dose comprises: |
| --- | --- |
| SEQ ID NO: 179* | SEQ ID NO: 179**** |
| SEQ ID NO: 179* | SEQ ID NO: 180***** |
| SEQ ID NO: 179* | SEQ ID NO: 181****** |

-continued

| First Dose comprises: | Second Dose comprises: |
| --- | --- |
| SEQ ID NO: 180** | SEQ ID NO: 179**** |
| SEQ ID NO: 180** | SEQ ID NO: 180***** |
| SEQ ID NO: 180** | SEQ ID NO: 181****** |
| SEQ ID NO: 181*** | SEQ ID NO: 179**** |
| SEQ ID NO: 181*** | SEQ ID NO: 180***** |
| SEQ ID NO: 181*** | SEQ ID NO: 181****** |

*The first dose may also include SEQ ID NO: 180 and/or SEQ ID NO: 181
**The first dose may also include SEQ ID NO: 179 and/or SEQ ID NO: 181
***The first dose may also include SEQ ID NO: 179 and/or SEQ ID NO: 180
****The second dose may also include SEQ ID NO: 180 and/or SEQ ID NO: 181
*****The second dose may also include SEQ ID NO: 179 and/or SEQ ID NO: 181
******The second dose may also include SEQ ID NO: 179 and/or SEQ ID NO: 180

The NAbs can be used as a therapeutic agent against CMV infection, as discussed above.

III. Therapeutic and Vaccine Compositions

Based on the vaccine-derived NAbs and the small peptides described above, therapeutic or vaccine compositions for treating or preventing CMV infection are also provided. In some embodiments, a therapeutic composition may include one or more vaccine-derived NAbs described above. In certain embodiments, a vaccine composition may include one or more small peptides comprising one or more linear epitopes on the gH/gL-PC. The one or more linear epitopes may be any of the epitopes described above. In such embodiments, the vaccine composition can be a multivalent vaccine comprising two or more small peptides, each peptide comprising a different linear epitope. The linear epitopes may be derived from (i.e., the epitope sequence is part of) the same subunit or different subunits of the gH/gL-PC. In one aspect, a multivalent vaccine may comprise two or more small peptides, each of which comprise a different linear epitope on a single subunit of the gH/gL-PC. For example, the two or more linear epitopes may be derived from the UL128 subunit of the gH/gL-PC; the two or more linear epitopes may be derived from the gH subunit of the gH/gL-PC, the two or more linear epitopes may be derived from the gL subunit of the gH/gL-PC, the two or more linear epitopes may be derived from the UL130 subunit of the gH/gL-PC; or the two or more linear epitopes may be derived from the UL131A subunit of the gH/gL-PC. In another aspect, a multivalent vaccine may comprise two or more small peptides, wherein the two or more small peptides comprise different linear epitopes derived from two or more different subunits of the gH/gL-PC. For example, the multivalent vaccine may comprise two or more small peptides, each of which comprises one or more linear epitopes, wherein at least one of the linear epitopes on one of the small peptides is derived from the UL128 subunit of the gH/gL-PC and at least one of the linear epitopes on another small peptide is derived from the gH subunit of the gH/gL-PC. Such therapeutic or vaccine compositions can be administered to a subject to treat or prevent CMV infections, particularly HCMV infections.

The therapeutic or vaccine compositions described above may also include one or more pharmaceutically acceptable carrier. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

IV. Methods of Treating or Preventing CMV Infections

The therapeutic or vaccine compositions described herein may be used to treat or prevent any HCMV infection that infects epithelial cells, endothelial cells, fibroblasts or a combination thereof. Examples of HCMV infections that may be treated or prevented using the methods described herein may include, but is not limited to, congenital HCMV infection, opportunistic HCMV infections in subjects with compromised immune system (e.g., organ and bone marrow transplant recipients, cancer patients and chemotherapy recipients, patients receiving immunosuppressive drugs and HIV-infected patients) and silent HCMV infections in otherwise healthy subjects.

Passive administration of immunoglobulins (HCMV-HIG) has shown contrasting results in clinical trials. Vaccine-derived NAbs disclosed herein, once humanized, can be used as passive immunotherapy agents to lower the transmission rate of HCMV from the mother to the fetus in documented cases of HCMV primary infection or reactivation. In this setting, a humanized vaccine-derived NAb can be used either alone or in combination with a human derived NAb.

In some embodiments, a method for treating or preventing CMV infection may include administering a therapeutically effective amount of a composition comprising one or more vaccine-derived NAbs, such as those described herein, to a subject.

In some embodiments, a method for treating or preventing CMV infection may include administering a therapeutically effective amount of a composition comprising one or more small peptides, such as those described herein, to a subject. The small peptide comprises one or more epitopes recognized by one or more vaccine-derived NAbs.

In certain embodiments, a method for treating or preventing CMV infection may include administering one or more doses of a therapeutically effective amount of a composition comprising one or more small peptides to a subject. In certain embodiments, a method for treating or preventing CMV infection may include administering a first dose of a therapeutically effective amount of a composition comprising one or more small peptides to a subject and administering a second dose of a therapeutically effective amount of a composition comprising one or more small peptides to the subject after administration of the first dose. In certain embodiments, the second dose may be administered to the subject about one week, about two weeks, about three weeks, about four weeks, or about five weeks after administration of the first dose. In certain embodiments, at least one of the doses includes administering a therapeutically effective amount of a composition comprising one or more small peptides, at least one of which is SEQ ID NO: 180. In certain embodiments, the first dose includes administering a therapeutically effective amount of a composition comprising one or more small peptides, at least one of which is SEQ ID NO: 180. In certain embodiments, the first dose includes administering a therapeutically effective amount of a composition comprising SEQ ID NO: 180 and the second dose includes administering a therapeutically effective amount of a composition comprising SEQ ID NO: 179. In certain embodiments, the first and second dose includes administering a therapeutically effective amount of a composition comprising SEQ ID NO: 180.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, curing the condition, or some combination thereof. Treatment may also mean a prophylactic or preventative treatment of a condition. Treatment using a vaccine may result in prevention of a disease or condition, but also may refer to the generation of a beneficial immune response that may not necessarily prevent the condition or treatment entirely. The treatment entails administering to a subject a therapeutically effective amount of a vaccine-derived NAb, a composition comprising one or more vaccine-derived NAbs, a small peptide, or a composition comprising one or more small peptides described herein.

The term "a therapeutically effective amount" or "an effective amount" as used herein refers to an amount of a substance that produces a desired effect. For example, a population of cells may be contacted or an animal may be administered with an effective amount of the pentameric complex to produce a desired NAb. A therapeutically effective amount of a composition comprising an NAb or a vaccine composition comprising a small peptide disclosed herein may be used to produce a therapeutic effect in a subject, such as preventing or treating a target condition, alleviating symptoms associated with the condition, or producing a desired physiological effect. The precise effective amount or therapeutically effective amount is an amount of the composition that will yield the most effective results in terms of efficacy of treatment in a given subject or population of cells. This amount will vary depending upon a variety of factors, including but not limited to the characteristics of the substance (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further, an effective or therapeutically effective amount may vary depending on whether the substance is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a substance and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, Pa., 2005, which is hereby incorporated by reference as if fully set forth herein.

The therapeutic or vaccine compositions described herein may be administered by any suitable route of administration. A "route of administration" may refer to any administration pathway known in the art, including but not limited to aerosol, enteral, nasal, ophthalmic, oral, parenteral, rectal, transdermal (e.g., topical cream or ointment, patch), or vaginal. "Parenteral" refers to a route of administration that is generally associated with injection, including intraorbital, infusion, intraarterial, intracapsular, intracardiac, intradermal, intralingual, intramuscular, intraperitoneal, intrapulmonary, intraspinal, intrasternal, intrathecal, intrauterine, intravenous, subarachnoid, subcapsular, subcutaneous, transmucosal, or transtracheal. In one embodiment, the composition comprising a vaccine-derived NAb or a small peptide is administered by injection.

V. Methods of Detecting CMV Infection

Screening or testing for CMV infections is very important for pregnant women, newborns, and immunocompromised patients. Vaccine-derived NAbs may be used as a diagnostic tool to detect CMV antigens in humans or animals or other biological samples or to detect CMV in cell cultures inoculated with infected samples. In particular, NAbs binding to conserved epitopes, such as 13B5, which binds a linear epitope on UL128 present on all the clinical strains, are capable of detecting HCMV antigens independently of the strain.

In certain embodiments, a vaccine-derived NAb may be used to detect CMV in a biological sample obtained from a subject by contacting the sample with the vaccine-derived NAb. The vaccine-derived NAb can be used both as a diagnostic tool and as prognostic tool. Once the subject is tested positive for CMV infection, the subject is administered a treatment for CMV infection and then subjected to additional tests to monitor the progress of the treatment.

Also disclosed herein is an assay kit for diagnosing or prognosing CMV infection in a subject including a vaccine-derived NAb and one or more reagents for performing the assay. Optionally, the kit may include an instruction manual for performing the assay, a known CMV antigen as a positive control, and/or a negative control.

VI. Methods of Identifying Small Peptides with Potential Use as Peptide Vaccines As disclosed above, small peptides binding to linear epitopes on subunits of the pentameric complex are particularly useful for developing peptide vaccine compositions for preventing CMV infections. Vaccine-derived NAbs disclosed herein can be used to identify additional small peptides comprising one or more epitopes on the pentameric complex.

In some embodiments, a vaccine-derived NAb is used to bind to a peptide library constructed with one or more subunits of the pentameric complex in an ELISA assay. The peptides having strong binding affinity to the vaccine-derived NAbs are identified. Optionally, these peptides can be further modified by substituting, deleting, or adding one or more amino acid residues. The modified peptides may be tested for binding affinity to the vaccine-derived NAbs to select the peptides having improved binding affinity. Both the peptides without modification and the modified peptides can be used for developing peptide vaccines described above.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entireties, as if fully set forth herein.

EXAMPLES

Materials and Methods

Cells.

ARPE-19 and MRC-5 (ATCC) were maintained in Dulbecco's minimal essential medium (DMEM, Corning, Corning, N.Y., USA) or minimal essential medium (MEM, Corning), respectively, supplemented with 10% fetal bovine serum (FBS, HyClone, Logan, Utah, USA). HUVEC (ATCC) were grown in VascuLife Basal Medium added with VascuLife EnGS LifeFactors (Lifeline Cell Technology, Frederick, Md., USA). BHK-21 cells (ATCC) were maintained in MEM with the addition of 10% FBS, 1 mM sodium pyruvate and 0.1 mM non-essential amino acids (Life Technologies, Grand Island, N.Y., USA).

Isolation and Culture of CTB.

With written informed consent, term (>37 weeks gestation) placentae from HIV-1 seronegative and Hepatitis B uninfected women (>18 years of age) were obtained immediately following elective caesarian section without labor from Emory Midtown Hospital in Atlanta, Ga. Approval of the study was granted by the Emory University Institutional Review Board (IRB). Written informed consent was obtained from donors, and samples were de-identified prior to handling by laboratory personnel. In order to isolate CTB, membrane-free villous was dissected from the placenta, as previously described (53-55). The tissue was thoroughly washed and mechanically dispersed in Hank's balanced salt solution (HBSS) to minimize peripheral blood contamination. Minced tissue fragments were then subjected to three sequential enzymatic digestions in a solution containing 0.25% trypsin (Mediatech Inc., Manassas, Va., USA), 0.2% DNase I (Roche Diagnostics, Mannheim, Germany), 25 mM HEPES, 2 mM $CaCl_2$), and 0.8 mM $MgSO_4$ in HBSS at 37° C. Following each digestion, the undigested tissue was removed by passage through a gauze and 100 μm cell strainer (BD Biosciences, Franklin Lakes, N.J., USA) and washed with PBS. Supernatants from the second and third digestions were collected and the resulting cell pellets were resuspended in 1:1 DMEM/F12 supplemented with 10% FBS, 1 mM L-glutamine, and 1% pen/strep (Sigma-Aldrich, St. Louis, Mo., USA). The CTB were isolated on a discontinuous gradient of Percoll (GE Healthcare, Uppsala, Sweden) (50%/45%/35%/30%) by centrifugation. Cells migrating to the 35%/45% Percoll interface were recovered and immunopurified by negative selection with simultaneous treatment with anti-CD9 (to exclude EnC, FB, platelets, smooth muscle, extravillous trophoblast cells, B cells and monocytes) and anti-CD45RA (to exclude leucocytes) antibodies and magnetic beads (Miltenyi Biotech, Bergisch Gladbach, Germany) (56, 57). The purity of the CTB population was assessed by cytokeratin-7 staining and was on average >97%. Vimentin staining to quantify contamination from mesenchymal cells was on average <3% (56-58).

Antibodies.

Cytogam (CMV-HIG, 50 mg/ml) was obtained from the manufacturer (Baxter-Healthcare Corp., Irvine, Calif., USA). The isolation of anti-gH Ab AP86, anti-pp65 Ab 28-103, and anti-HCMV IE1 Ab (p63-27) has been described (59-61).

Viruses. MVA expressing all five PC subunits (MVA-PC), single PC subunits or subunit combinations were reconstituted from MVA-BAC as previously described (36, 62) and propagated on BHK-21 (63). For preparing MVA virus stocks, MVA was harvested from infected BHK-21, purified by 36% sucrose density ultracentrifugation, and resuspended in 1 mM Tris-HCl (pH 9) (36, 62, 64). MVA stocks were maintained at −80° C. Purified MVA was titrated on BHK-21 by standard procedure. HCMV strain TB40/E-GFP (TB40/E) was kindly provided by Christian Sinzger (Ulm University, Germany) (65). HCMV strain TR-GFP (TR) was a gift from Jay Nelson (Oregon Health & Sciences University, Portland, Oreg., USA). HCMV strains Davis, Towne and AD169 were kindly provided by John Zaia (Beckman Research Institute of the City of Hope, Duarte, Calif., USA)

(64). Generation of HCMV stocks was performed as previously described (36). Briefly, ARPE-19 were infected with HCMV and re-seeded until 70-80% of the cells were GFP-positive. Virus particles were concentrated from clarified medium by ultracentrifugation (70,000×g for one hour) over 20% sucrose (w/v) in Tris-buffered saline (0.1 M Tris-Cl, pH 7.4, 0.1 M NaCl). Concentrated virus was resuspended in Tris-buffered saline and stored at −80° C. Virus titration was performed by adding serial dilution of the virus to ARPE-19, MRC-5, HUVEC and CTB, and by immunostaining for immediate-early-1 protein (IE-1) after 48 hours incubation. HCMV titer on CTB was on average three times lower than the one measured on ARPE-19.

Mice and Immunizations.

The Institutional Animal Care and Use Committee (IACUC) of the Beckman Research Institute of City of Hope approved protocol #98004 assigned for this study. All study procedures were carried out in strict accordance with the recommendations in the Guide for the Care and Use of Laboratory Animals and Public Health Service Policy on the Human Care and Use of laboratory Animals. Methods of euthanasia followed "Report of the AVMA Panel on Euthanasia" (avma.org/kb/policies/documents/euthanasia.pdf). BALB/cJ mice (Jackson Laboratory, Bar Harbor, Me., USA) were vaccinated with MVA-PC as previously described (36) and boosted four days before the spleen was removed for hybridoma production.

Hybridoma Derivation.

Hybridomas were derived by conventional procedure (66). Briefly, myeloma partner cells (P3X63Ag8.653, ATCC) were maintained in RPMI-1640 (Corning) supplemented with 10% FBS. Splenocytes and myeloma cells were counted, and fusion was performed at a 1:5 ratio by adding 1 ml PEG 1500 (Sigma-Aldrich). After centrifugation, fused cells were resuspended in RPMI-1640 supplemented with 15% FBS, 10% UltraCruz Hybridoma Cloning Supplement (HCS, Santa Cruz Biotechnology, Santa Cruz, Calif., USA), HAT media supplement (Sigma-Aldrich) at a concentration of $5 \times 10^5$ splenocytes/ml. Cells were seeded in 96 well plates and incubated in a 5% $CO_2$, 37° C. incubator. Selected hybridoma clones were grown in RPMI-1640 supplemented with 15% FBS and 10% HCS. Each clone underwent 2 rounds of single cell subcloning to ensure the clonality of the antibody (66). Collected hybridoma supernatant was added with 20 mM sodium phosphate buffer (pH 7.0) and NAbs were purified using a HiTrap Protein G HP 5 ml column (GE Healthcare) according to the manufacturer's instructions. Ab concentration was verified with Bradford-Coomassie brilliant blue dye method using a bovine gamma globulin standard (Thermo Scientific/Pierce, Rockford, Ill., USA).

Neutralization Assays.

Cells were seeded at $1.5 \times 10^4$ cells/well (ARPE-19, HUVEC and MRC-5) or $1.5 \times 10^5$ cells/well (CTB) in a clear bottom 96-well plate (Corning). Around 24 hours later the medium in every plate was replaced with 50 μl per well of fresh growth medium. Naturalization assays were performed as previously described (36). Briefly, serial two-fold dilutions of the purified NAbs were prepared in complete growth medium in a final volume of 75 μl. NAb dilutions were mixed with 75 μl of complete growth medium containing approximately 9000 PFU of HCMV TB40/E or TR and incubated for 2 h at 37° C. The mixture was transferred to the cells (50 μl each, duplicate wells). After 48 hours, cells were fixed and IE-1 immunostaining performed as previously described (36). NAb concentration inhibiting 50% of the virus infectivity (IC50) was calculated as previously described (36).

Antibody Purification.

Hybridoma clones of interest were grown in RPMI-1640 supplemented with 15% FBS and 10% HCS. Each clone underwent 2 rounds of single cell cloning to ensure the monoclonality of the antibody. After cloning, the hybridomas were grown in RPMI-1640 supplemented with 15% FBS. Periodically, half of the medium was collected and replaced with fresh one. When the collected hybridoma supernatant was about 500 ml, 200 ml of 20 mM sodium phosphate buffer (pH 7.0) were added and the antibody was purified using a HiTrap Protein G HP 5 ml column (GE Healthcare, Piscataway, N.J., USA) according to the manufacturer's instructions. Concentration of the antibody was verified with Bradford-Coomassie brilliant blue dye method using a bovine gamma globulin standard (both Thermo Scientific/Pierce, Rockford, Ill., USA).

NAb Binding Specificity.

NAb subunit specificity was evaluated by staining BHK-21 cells infected with different MVA recombinants. One or more vectors were used to co-infect BHK-21 at an MOI of 5. The combinations analyzed were: UL128, UL130, UL131A, UL128/130, UL128/131A, UL130/131, UL128/130/131A, gH, gH/gL, gH/gL/UL128, gH/gL/UL130, gH/gL/UL131A, gH/gL/UL128/130, gH/gL/UL128/131A, gH/gL/UL130/131A and gH/gL/UL128/130/131A. Four hours post infection cells were fixed and permeabilized using Cytofix/Cytoperm solution (BD Biosciences). NAbs (1 mg/ml) were diluted 1:500 in perm/wash buffer (BD) and added to the cells for 1 hour at 4° C. After washing with perm/wash buffer, Alexa Fluor 647 Goat Anti-Mouse IgG (Life Technologies) was added at a dilution of 1:2,000. Cells were washed again and resuspended in PBS/0.1% BSA. Fifteen thousand events were collected using the Gallios Flow Cytometer (Beckman Coulter, Miami, Fla., USA) and analyzed with FlowJo Software (Tree Star, Ashland, Oreg., USA). Uninfected cells and cells infected with MVA-Venus were used as controls. GFP expression was analyzed for confirming MVA infection since all the constructs contain a GFP expression cassette (36, 62).

Cell-to-Cell Spread Inhibition Assay.

NAbs ability to inhibit cell-to-cell spread and/or syncytia formation was evaluated on EpC using TB40/E and TR. ARPE-19 cells were seeded on a black 96-well plate (Costar) and infected 24 hours later with HCMV TB40/E or TR (MOI of 1 as titrated on ARPE-19). After incubation for 24 hours, cells were extensively washed with PBS and two-fold serial dilutions of each NAb were added to the wells in a total volume of 200 μl. After 8 days incubation, the plates were imaged with a Zeiss Axiovert fluorescence microscope (Carl Zeiss, Jena, Germany) and cellular GFP was quantified using ImagePro Premier Software (Media Cybernetics, Silver Spring, Md., USA). The percent of spread inhibition (IC) for each dilution was calculated as: IC=[1−(fluorescence in infected wells incubated with NAb)/(fluorescence in infected wells without NAb)]×100. 50% cell-to-cell spread inhibition (IC50) was calculated by determining the linear slope of the graph plotting IC versus NAb dilution by using the next higher and lower IC values that were closest to 50%.

Antibody Binding Affinity.

Antibody binding affinity was determined as described (67). Briefly, 10 mg of purified NAbs were biotinylated using EZ-Link NHS-PEG4-Biotin Biotinylation Kit (Thermo Scientific/Pierce) following manufacturer's instructions. BHK-21 cells were infected with MVA-PC at an MOI of 5. After an incubation of 4 hours at 37° C., the cells were dispensed at a concentration of $1 \times 10^5$ cells/well in a 96-well V-bottom plate, followed by 2 hours incubation at 4° C. with two-fold serial dilutions of the biotinylated NAb in PBS/0.1% BSA. Dilutions ranged from 500 µg/ml to 0.1 ng/ml. Cells were washed twice with PBS/0.1% BSA and incubated for 1 hour at 4° C. in the presence of streptavidin-DyLight 650 (Thermo Scientific) diluted 1:500 in PBS/0.1% BSA. After washing twice, cells were fixed with 4% paraformaldehyde. Fifteen thousand events were acquired with the Gallios Flow Cytometer and analyzed with FlowJo Software. The equilibrium binding constant (Kd) was derived by plotting fluorescence as a function of the logarithm of NAb concentration to obtain a sigmoidal curve analyzed with the 4 Parameter Logistic (4PL) nonlinear regression model (GraphPad Prism 6 Software, San Diego, Calif., USA).

Competition Assay.

NAb competition was evaluated as follows. BHK-21 cells were infected with MVA-PC at an MOI of 5 and 4 hours later treated with Cytofix/Cytoperm. Around $1 \times 10^5$ cells were incubated for 2 hours with 20 to 100-fold excess unlabeled competitor NAb (from 100 to 200 µg/ml). After washing with perm/wash buffer cells were incubated for 2 hours in the presence of 1 to 5 µg/ml biotinilated NAbs. For every NAb, cells in which the unlabelled competitor was not added to the biotinilated NAbs were used to determine maximum binding. Cells were washed once with perm/wash buffer and incubated for 1 hour with streptavidin-DyLight 650 diluted 1:500. After a final washing step, cells were resuspended in PBS/0.1% BSA, acquired with Gallios Flow Cytometer and analyzed with FlowJo Software. For every antibody pair, the percentage of inhibition was calculated as: 100−[(% fluorescent cells with competitor NAb/% fluorescent cells without competitor NAb)×100]. The complete prevention of binding of a biotinilated NAb by its unlabelled counterpart was used as a validation of the assay.

NAb Variable Heavy and Light Chain Sequence Characterization.

Total RNA was extracted from hybridomas using the SV total RNA isolation system (Promega, Madison, Wis., USA). cDNA was generated by random hexamers (Qiagen GmbH, Hilden, Germany) and Superscript III reverse transcriptase (Life Technologies) following the manufacturer's instruction. The kappa variable genes were characterized by a 5'RACE PCR in which the cDNA was tailed with poly dGTP by terminal transferase (New England BioLabs, Ipswich, Mass., USA). A 3' reverse gene-specific primer located in the kappa constant region near the variable region (TG-GATGGTGGGAAGATGGATACAGT) (SEQ ID NO: 183) was adopted together with poly dCTP to amplify the kappa variable genes. For the gamma variable genes, a protocol from Fields et al. (68) was followed. VH and VL genes were amplified by Phusion high-fidelity DNA polymerase (Thermo Scientific) and cloned into pCR4Blunt-TOPO vector (Life Technologies) following the manufacturer's instruction. Three clones derived from each VH/VL genes were sequenced.

Immunoblot.

Immunoblot to determine NAbs binding to denaturated gH was performed using lysates from cells infected with a gH-expressing adenoviral vector (Ad-gH) as previously described (36). Anti-gH Ab AP86 (59), 18F10, 21E9, 62-11, 62-100 and 2-80 were employed at a dilution of 10 µg/ml. Anti-MEK1/2 (Cell Signaling Technology, Danvers, Mass., USA) was diluted 1:1000. Immunoblot to evaluate 18F10 and AP86 binding to lysates from cells infected with different HCMV strains was performed as described above with the difference that lysates consisted in $2.5 \times 10^5$ MRC-5 infected for 4 days with an MOI of 1 of HCMV strain Davis, Towne, AD169, TB40/E or TR. Anti-pp65 was used to show HCMV infection in all the samples independently from the strain used.

Example 1. Isolation of Durable HCMV Specific NAbs from MVA-gH/gL-PC Vaccinated Mice It was previously demonstrated that mice vaccinated three times by four week interval with MVA-gH/gL-PC develop high titer EpC specific NAb responses that remained stable over at least one year (36). Remarkably, only two vaccinations with MVA-gH/gL-PC appeared to be sufficient to induce maximum high titer EpC NAb titers. In order to characterize in detail the specific activity of the antibody response induced by MVA-gH/gL-PC, a panel of monoclonal NAbs was isolated after induction of anamnestic responses by a fourth dose of vaccination forty-eight to seventy-two weeks after initial immunization. NAb titers after the fourth vaccination could be boosted to levels that were observed after the second or third boost with MVA-gH/gL-PC at week four and eight (FIG. 1), suggesting that vector immunity had only little influence on the ability of MVA-gH/gL-PC to boost NAbs to gH/gL-PC. Splenocytes were immortalized by conventional hybridoma technology (66) and hybridoma supernatants were screened directly by ARPE-19 EpC based microneutralization using HCMV strain TB40/E for infection. Ten NAbs (1B2, 54E11, 21F6, 12E2, 13B5, 18F10, 21E9, 62-11, 62-100 and 2-80) that blocked HCMV infection of ARPE-19 were identified. NAbs were subcloned, purified by affinity chromatography, and characterized as described below.

Example 2. MVA-PC Vaccine-Derived NAbs Recognize Epitopes of the PC and gH

Figure 2A:
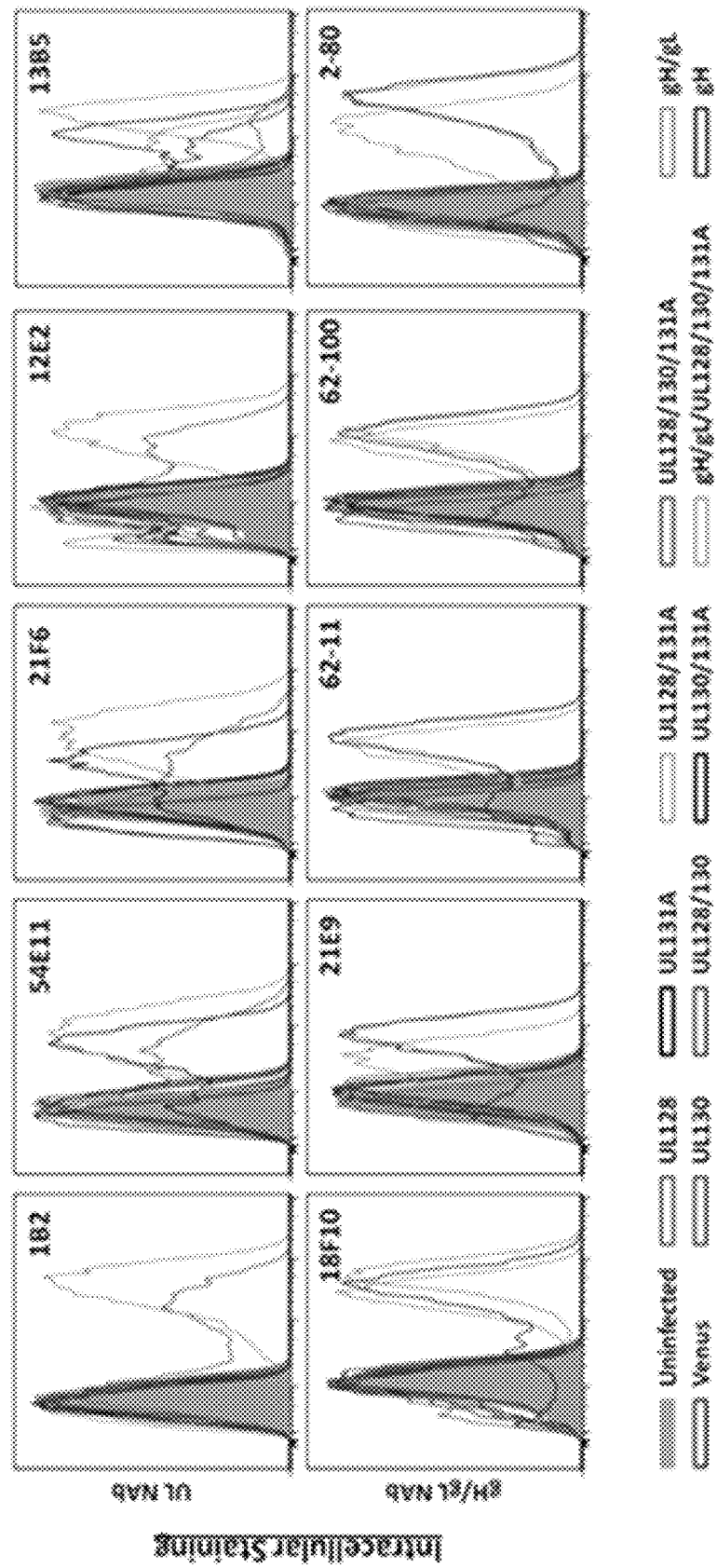
FIG. 2A shows intracellular recognition of PC subunits by isolated NAb. Shown is FC staining by MVA-PC vaccine-derived NAb of permeabilized BHK-21 cells infected with different MVA vectors expressing one or more subunits of the PC.

PC-specific NAbs isolated from chronically infected HCMV+ individuals predominantly recognize conformational antigenic sites formed by UL130/131A and UL128/130/131A (32, 33). Only one human NAb has been published that recognizes an epitope within the UL128 subunit (32). A panel of NAbs from mice immunized with the MVA-PC vaccine was isolated by conventional hybridoma technology combined with screening for neutralization against TB40/E on ARPE-19 EpC. In order to determine the antigen specificity of the vaccine-derived NAbs, intracellular flow cytometry (FC) staining of permeabilized BHK-21 cells infected with MVA expressing single subunits or combinations of two or more subunits of the PC was evaluated. Consistent with human NAbs, four vaccine-derived PC-specific NAbs that recognized quaternary epitopes formed by UL130/UL131A or UL128/130/131A, and one NAb (13B5) with UL128 specificity were identified (FIG. 2 and Table 2). Staining with 1B2 and 12E2 NAbs was observed with UL128/130/131A or all five PC subunits. Expression of single subunits or any PC subunit combination with only one or two of the UL128/130/131A subunits did not result in binding of 1B2 and 12E2. In contrast, NAbs 54E11 and 21F6 showed binding with UL130/131A, the three UL128/130/131A subunits, or all five PC subunits. Single subunits or PC subunit combinations lacking UL130/131A failed to enable binding of 54E11 and 21F6. NAb 13B5 showed binding with UL128 alone or combined with other PC subunits, whereas binding of 13B5 was not observed in the absence of UL128. Based on the vaccine's ability to elicit both EpC/EnC and FB specific NAbs (36), NAbs with gH specificity were also identified. Staining by these NAbs was confirmed with gH alone, in combination with gL, or together with all other four PC subunits. Binding of these antibodies was not observed when gH was missing (FIG. 2 and Table 2). Hence, MVA-PC elicits PC- and gH-specific NAbs that have antigen recognition patterns similar to human NAbs isolated from chronically infected HCMV+ individuals.

TABLE 2

NAb subunits recognition

| | UL128 | UL130 | UL131 | UL128 UL130 | UL128 UL131 | UL130 UL131 | UL128 UL130 UL131 | gH | gH/gL | gH/gL UL128 |
|---|---|---|---|---|---|---|---|---|---|---|
| 1B2 | - | - | - | - | - | - | + | - | - | - |
| 54E11 | - | - | - | - | - | + | + | - | - | - |
| 21F6 | - | - | - | - | - | + | + | - | - | - |
| 12E2 | - | - | - | - | - | - | + | - | - | - |
| 13B5 | + | - | - | + | + | - | + | - | - | + |
| 18F10 | - | - | - | - | - | - | - | + | + | + |
| 21E9 | - | - | - | - | - | - | - | + | + | + |
| 62-11 | - | - | - | - | - | - | - | + | + | + |
| 62-100 | - | - | - | - | - | - | - | + | + | + |
| 2-80 | - | - | - | - | - | - | - | + | + | + |
| 4A3 | - | - | - | - | - | + | - | - | - | - |
| 6G2 | - | - | - | - | - | - | - | + | + | + |
| 10G6 | - | - | - | - | - | - | - | + | + | + |
| 13B1 | - | - | - | - | - | - | - | + | + | + |
| 25H10 | - | - | - | - | - | - | - | + | + | + |

| | gH/gL UL130 | gH/gL UL131 | gH/gL UL128 UL130 | gH/gL UL128 UL131 | gH/gL UL130 UL131 | gH/gL UL128 UL130 UL131 |
|---|---|---|---|---|---|---|
| 1B2 | - | - | - | - | - | + |
| 54E11 | - | - | - | - | + | + |
| 21F6 | - | - | - | - | + | + |
| 12E2 | - | - | - | - | - | + |
| 13B5 | - | - | + | + | - | + |
| 18F10 | + | + | + | + | + | + |
| 21E9 | + | + | + | + | + | + |
| 62-11 | + | + | + | + | + | + |
| 62-100 | + | + | + | + | + | + |
| 2-80 | + | + | + | + | + | + |
| 4A3 | - | - | - | - | - | + |
| 6G2 | + | + | + | + | + | + |
| 10G6 | + | + | + | + | + | + |
| 13B1 | + | + | + | + | + | + |
| 25H10 | + | + | + | + | + | + |

Figure 2B:
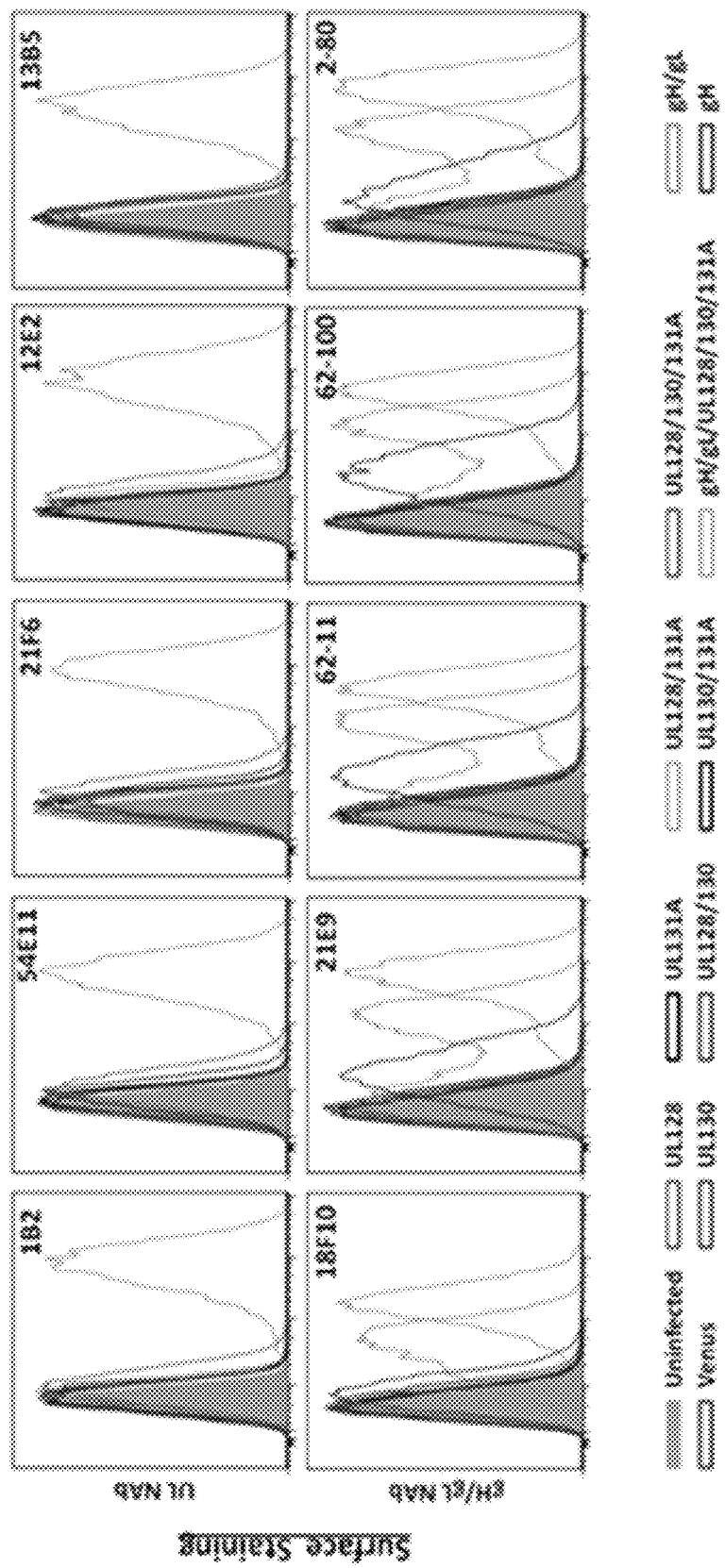
FIG. 2B shows cell surface recognition of PC subunits by isolated NAb. Shown is FC staining by MVA-PC vaccine-derived NAb of non-permeabilized BHK-21 cells infected with different MVA vectors expressing one or more subunits of the PC. Uninfected cells and cells infected with an MVA encoding for a fluorescent protein (Venus) were used as negative controls.

Example 3. MVA-PC-Infected Cells Present PC- and gH-Specific Neutralizing Epitopes at the Cell Surface Although it was reported that the five PC subunits expressed from MVA-PC assemble with each other intracellularly, it was unclear whether the complexes were transported to the cell surface and presented PC-specific neutralizing epitopes. The vaccine-derived NAbs for cell surface FC staining of live non-permeabilized BHK-21 cells infected with MVA-PC was compared to MVA vaccine vectors expressing single subunits or different subunit subset combinations of the PC. When compared to intracellular staining (FIG. 2A), different cell surface recognition patterns with the vaccine-derived PC-specific NAbs were observed (FIG. 2B). Intensive cell surface staining by the PC-specific NAbs was confirmed with all five PC subunits (MVA-PC), whereas no or only minimal cell surface staining by NAbs was observed with single subunits or subunit subsets of the complex (FIG. 2B). As confirmed for intracellular staining (FIG. 2A), intense cell surface staining by all gH-specific NAbs with gH alone, together with gL, or combined with all other four PC subunits was observed. In contrast to intracellular staining, cell surface staining by the anti-gH NAbs was more intense with all five PC subunits when compared to gH alone or only gH/gL. In addition, compared to gH single expression, stronger binding of the anti-gH NAbs was observed with gH/gL (FIG. 2B). These results demonstrate that the five PC subunits expressed from MVA-PC efficiently assemble with one another and present conformational neutralizing epitopes of the UL128/130/131A subunits and gH at the cell surface.

Figure 3:
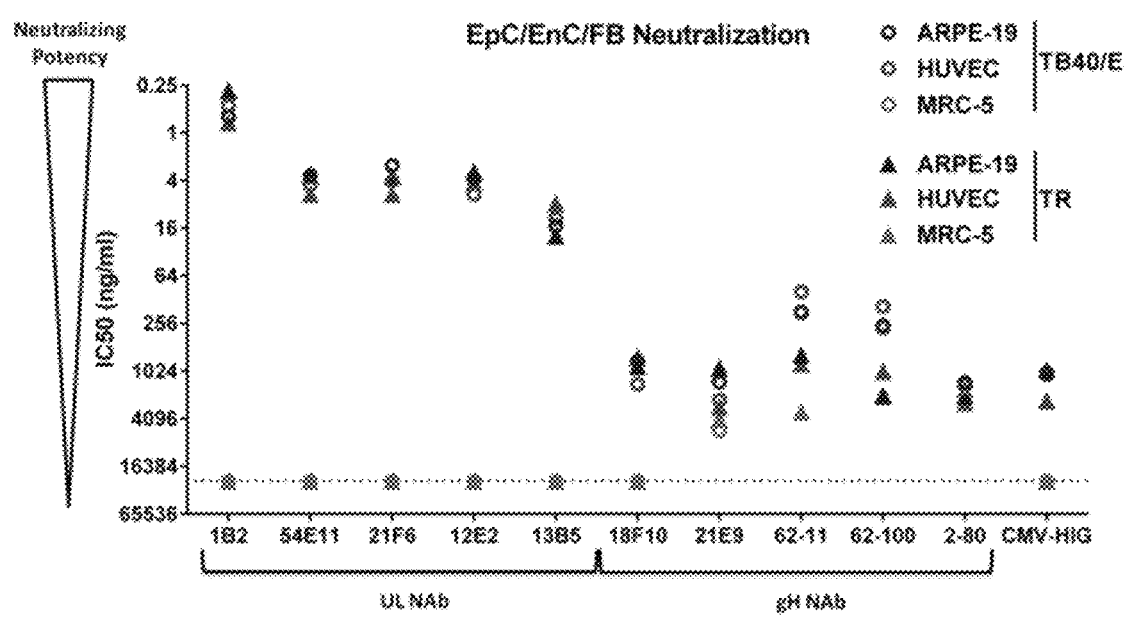
FIG. 3 shows neutralization potency of vaccine-derived NAb. NAb derived from MVA-PC immunized mice were used in a microneutralization assay to determine the antibody concentrations required to prevent 50% infection (IC50) of ARPE-19 EpC, HUVEC EnC, and MRC-5 FB with HCMV strains TB40/E and TR. CMV-HIG was used as a reference. Dotted line indicates the highest antibody concentration used in the assay (25 µg/ml).
Figure 4:
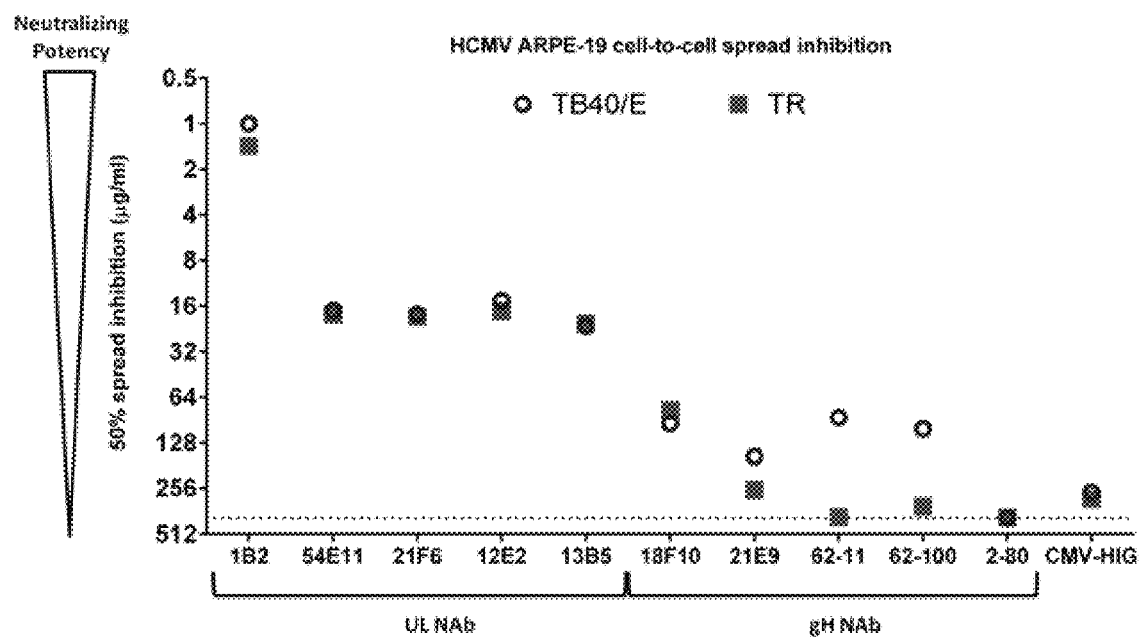
FIG. 4 shows inhibition of HCMV spread in EpC by NAb. ARPE-19 cells were infected with TB40/E or TR (MOI of 1), 24 hours later extensively washed, and incubated with serial dilutions of vaccine-derived NAb for 8 days. Cells were imaged for GFP quantification. The graph shows the NAb concentrations at which 50% reduction in the GFP positive area (IC50) in comparison to untreated controls was calculated. CMV-HIG was used as a control. The maximum evaluated antibody concentration is indicated by the dotted line.

Example 4. Vaccine-Derived PC-Specific NAbs are More Potent than gH-Specific NAb in Neutralizing HCMV In order to determine whether the vaccine-derived NAbs confer similar potency than previously described human NAbs (32) to prevent host cell entry, the inhibitory antibody concentration (IC50) that blocked 50% HCMV infection of ARPE-19 EpC, HUVEC EnC, or MRC-5 FB was evaluated using a standard microneutralization assay. Neutralization against HCMV strains TB40/E and TR was tested to evaluate whether sequence variation in the gH component influences the potency of the NAbs to neutralize HCMV (36, 69). Neutralization potency of HCMV hyperimmune globulin (CMV-HIG) was evaluated as a reference. All PC-specific NAbs blocked TB40/E or TR infection of ARPE-19 cells and HUVEC with potency that significantly exceeded (on average over 200-fold) that of anti-gH NAbs or CMV-HIG (FIG. 3 and Table 3). In contrast, most of the gH-specific NAbs inhibited HCMV infection of all investigated cell types with comparable potency, albeit with much lower potency than the PC-specific NAbs blocked ARPE-19/HU-VEC entry. Neutralization potency of the anti-gH NAbs was similar to that determined for CMV-HIG. Neutralization with CMV-HIG on MRC-5 FB at the highest investigated concentration (25 μg/ml) was not observed, which is consistent with observations obtained by others (37, 70). One gH-specific NAb (18F10) demonstrated inhibition potency comparable to the other anti-gH NAbs when measured on ARPE-19 cells and HUVEC, but it did not show ability to block HCMV infection of FB. The IC50 values of the vaccine-induced PC and gH-specific NAbs isolated were similar to published values determined for NAbs isolated from HCMV$^+$ individuals (Table 3). In contrast to the other anti-gH NAbs, two of the gH-specific NAbs (62-11, 62-100) blocked TR infection less potently than infection of TB40/E (FIG. 3), suggesting that anti-gH NAbs 62-11 and 62-100 may target epitopes that are antigenically distinct in TB40/E and TR. These results show that the vaccine-derived PC- and gH-specific NAbs have neutralization potency comparable to that observed for NAbs from chronically HCMV infected individuals.

analyzed by flow cytometry (FC) for staining by the isolated NAbs. All potent EpC/EnC neutralizers recognized antigenic sites that required co-expression of more than one subunit of UL128-UL131A, except one antibody (13B5) that showed specificity for UL128 (FIG. 2 and Table 2). NAbs 1B2 and 12E2 showed minimal antigen recognition for UL128/UL130/UL131A. These antibodies stained BHK cells infected with MVA-gH/gL-PC or MVA co-expressing UL128, UL130, and UL131A, though single subunits or any other subunit combination of gH/gL-PC were undetected (FIGS. 1 and 4). EpC/EnC neutralizer 54E11 and 21F6 demonstrated minimal antigen specificity for UL130/UL131A. These antibodies recognized co-expression of all five gH/gL-PC subunits, UL128/UL130/UL131A, or UL130/UL131A, whereas cells infected with MVA expressing single subunits or other gH/gL-PC subunit combinations remained unstained (FIG. 2 and Table 2). Antibody 13B5 with specificity for UL128 recognized UL128 single expression or UL128 expression together with any other combination of gH/gLPC subunits, but did not stain cells infected with MVA expressing only UL130, UL131A, or gH/gL (FIG. 2 and Table 2). All the NAbs that blocked EpCs/EnCs

TABLE 3

Potency of NAb in preventing HCMV TB40/E and TR infection of different cell types and epithelial cell-to-cell spread and their binding affinity to the PC

| Specificity/ NAb | TB40/E | | | | | TR | | | | |
|---|---|---|---|---|---|---|---|---|---|---|
| | IC50 (ng/ml) | | | | IC50 (μg/ml) ARPE-19 Spread | IC50 (ng/ml) | | | IC50 (μg/ml) ARPE-19 Spread | EC50 (M) Binding affinity |
| | ARPE-19 | HUVEC | MRC-5 | CTB | | ARPE-19 | HUVEC | MRC-5 | | |
| UL 1B2 | 0.6 | 0.5 | >25000 | 12.6 | 1 | 0.3 | 0.7 | >25000 | 1.4 | 3.2E−10 |
| 54E11 | 3.4 | 4.6 | >25000 | 24.9 | 17 | 3.4 | 5.9 | >25000 | 18 | 5.1E−10 |
| 21F6 | 2.6 | 4.0 | >25000 | 30.7 | 18 | 3.5 | 5.9 | >25000 | 19 | 6.2E−10 |
| 12E2 | 3.7 | 6.0 | >25000 | 72.1 | 15 | 3.1 | 4.2 | >25000 | 17 | 1.1E−09 |
| 13B5 | 15 | 12 | >25000 | 99.8 | 22 | 19.9 | 7.7 | >25000 | 21 | 6.8E−10 |
| 4A3 | 80.15 | 46.42 | >25000 | | | 44.6 | 10.15 | >25000 | | |
| gH 18F10 | 763 | 1490 | >25000 | 8800 | 95 | 885 | 675 | >25000 | 78 | 6.5E−09 |
| 21E9 | 1409 | 2374 | 5780 | 42362 | 157 | 926 | 2916 | 4141 | 262 | 1.8E−08 |
| 62-11 | 185 | 102 | 182 | 2760 | 87 | 641 | 830 | 3346 | 395 | 1.7E−09 |
| 62-100 | 270 | 156 | 293 | 3623 | 103 | 2126 | 1031 | 1983 | 337 | 3.3E−09 |
| 2-80 | 1433 | 1405 | 1597 | >50000 | >400 | 2125 | 2540 | 1717 | 398 | 2.8E−09 |
| 6G2 | 689 | | 542 | | | 1255 | | 6800 | | |
| 10G6 | 326 | | 481 | | | 706 | | 6315 | | |
| 13B1 | 3022 | | | | | 6993 | | | | |
| 25H10 | 188 | | 602 | | | 1076 | | 6235 | | |
| CMV-HIG | 1086 | 1124 | >25000 | 5478 | 271 | 991 | 2413 | >25000 | 299 | ND |
| gH AP86 | 1005 | ND | >25000 | ND | ND | ND | ND | ND | ND | ND |

In ARPE-19, HUVEC and MRC-5 neutralization assays the maximum Ab concentration tested was 25 μg/ml. In CTB neutralization assay the maximum Ab concentration tested was 50 μg/ml. In cell-to-cell spread assay the maximum Ab concentration was 400 μg/ml.
ND = not done.

Example 5. Vaccine-Derived NAbs Recognize Conformational Epitopes

Most of the potent NAbs of HCMV$^+$ individuals that block HCMV infection of EpCs target conformational epitopes constituted by two or more subunits of gH/gL-PC, but mainly epitopes formed by the UL128-UL131A subunits. In order to determine similar gH/gL-PC subunit specificity for the vaccine-derived NAbs, intracellular antibody recognition of single subunits, different combination of two or more subunits, or all five subunits of gH/gL-PC expressed from MVA was performed. Baby hamster kidney (BHK) cells that allow efficient MVA replication were infected with the different MVA constructs, fixed and permeabilized, and and FBs HCMV infection (21E9, 62-11, 62-100, 2-80, 13B1, 6G2, 10G6 and 25H10) showed specificity for gH, gH/gL and all five gH/gL-PC subunits expressed from MVA, whereas no staining was observed when any combination of the UL128 to UL131A was expressed without gH (FIG. 2 and Table 2). These antigen recognition patterns are strikingly similar to that of natural NAbs to gH/gL-PC. Finally, despite unable to neutralize HCMV entry of FBs, NAb 18F10 showed a minimal binding specificity for gH, and also bound when cells were infected with MVA-gH/gL-PC. This result shows for the first time the existence of an NAb specific for gH but neutralizing only entry into EpCs/EnCs.

Figure 5:
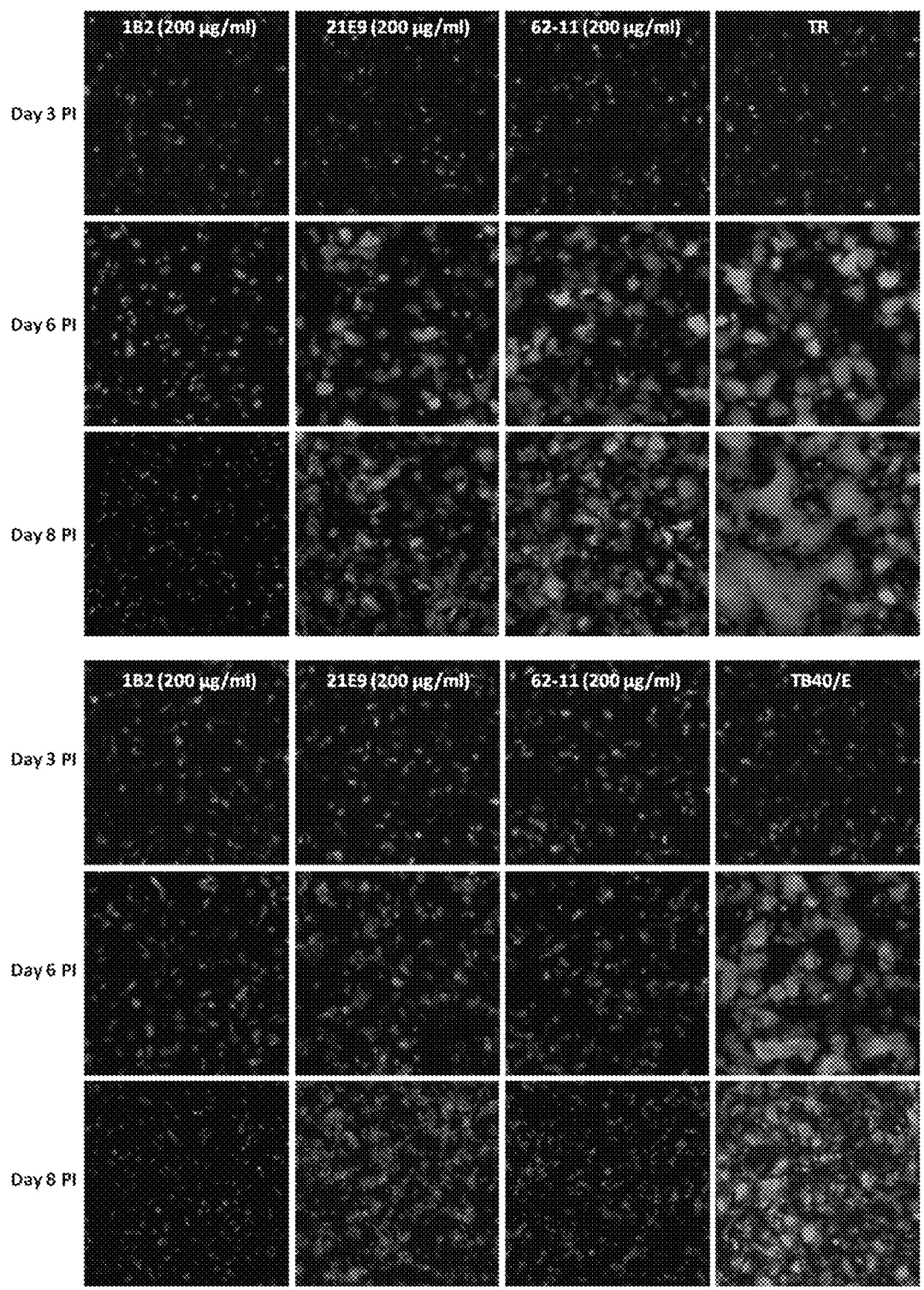
FIG. 5 shows NAbs mediated inhibition of TR and TB40/E cell-to-cell spread on EpCs. Shown are sequential pictures of TB40/E or TR infected cells in the presence or absence of NAb 1B2, 21E9 and 62-11 added at 200 µg/ml. NAbs were added at day 1 post-infection (PI) and pictures were taken at the center of the wells at day 3, 6 and 8 PI. The same magnification (50×) was used in all the pictures.

Example 6. PC-Specific NAbs Limit HCMV Spread in EpC More Potently than Anti-gH NAbs HCMV replication is highly cell-associated and the virus predominantly spreads from cell to cell (71, 72). Inhibition of HCMV cell-to-cell spread and/or syncytia formation besides neutralization of cell-free HCMV entry may be an important antibody function to prevent dissemination. To test whether the MVA-PC vaccine-derived NAbs can block spread of HCMV, the potency to inhibit HCMV TB40/E or TR cell-to-cell spread and/or syncytia formation in ARPE-19 EpC was evaluated. As shown in FIG. 3 for the neutralization potency, significant differences in the potency of the PC- and gH-specific NAbs to prevent HCMV cell-to-cell spread were found (FIG. 4 and Table 3). All NAbs specific for PC subunits blocked TB40/E and TR spread in ARPE-19 cells with potency that significantly exceeded those of the anti-gH NAbs or CMV-HIG. In contrast, the anti-gH NAbs demonstrated only very low spread inhibition potency, or were even unable to prevent HCMV spread in ARPE-19 cells at a cut-off concentration of 400 μg/ml. Most of the anti-gH NAbs demonstrated spread inhibition potency that was comparable to or only slightly higher than those of CMV-HIG. The ability of individual NAbs to block viral spread in ARPE-19 EpC was similar to their property to neutralize HCMV infection of these cells, with the variation that higher antibody amounts (1000-fold) were required to interfere with HCMV cell-to-cell spread than with HCMV entry (Table 3). Consistent with the neutralization by the anti-gH NAbs, less potent spread inhibition of HCMV TR than of TB40/E by two of the anti-gH NAbs (62-11 and 62-100) was observed, suggesting that sequence variation in the gH protein influences the ability of the NAb to prevent HCMV spread. FIG. 5 shows the effect of potent PC-specific NAb 1B2 and anti-gH NAbs 21E9 and 62-11 compared to untreated controls to interfere with TB40/E and TR spread and/or syncytia formation in ARPE-19 cells. These results indicate that PC-specific NAbs are more potent than anti-gH NAbs to prevent HCMV spread in EpC.

Figure 6A:
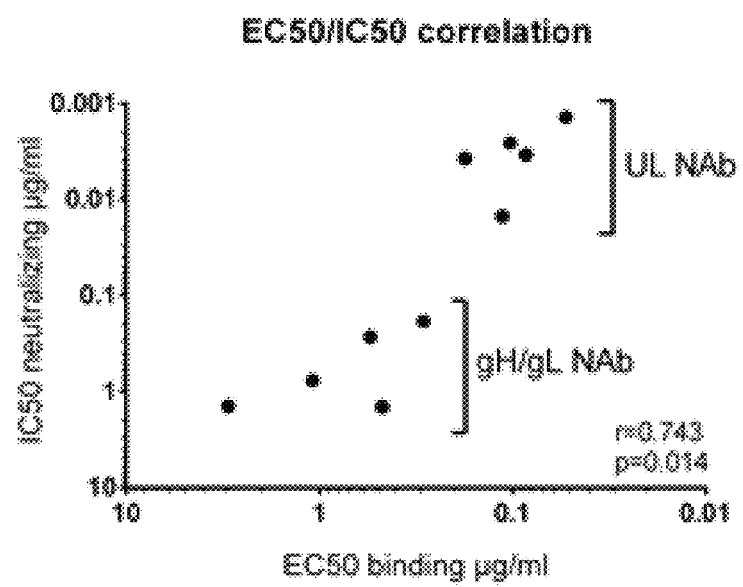
FIGS. 6A-6C show correlation analyses between NAb binding affinity and neutralizing potency.
Figure 6B:
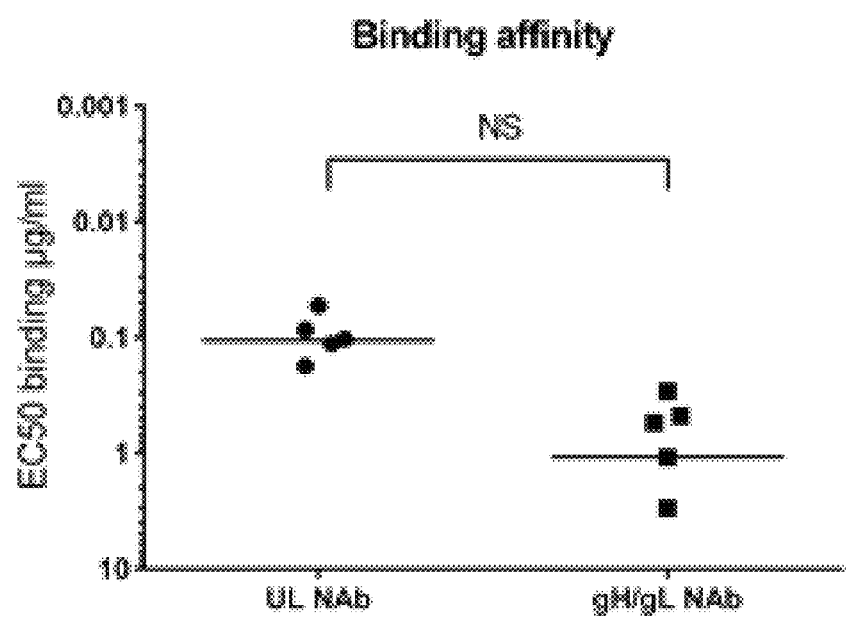
Figure 6C:
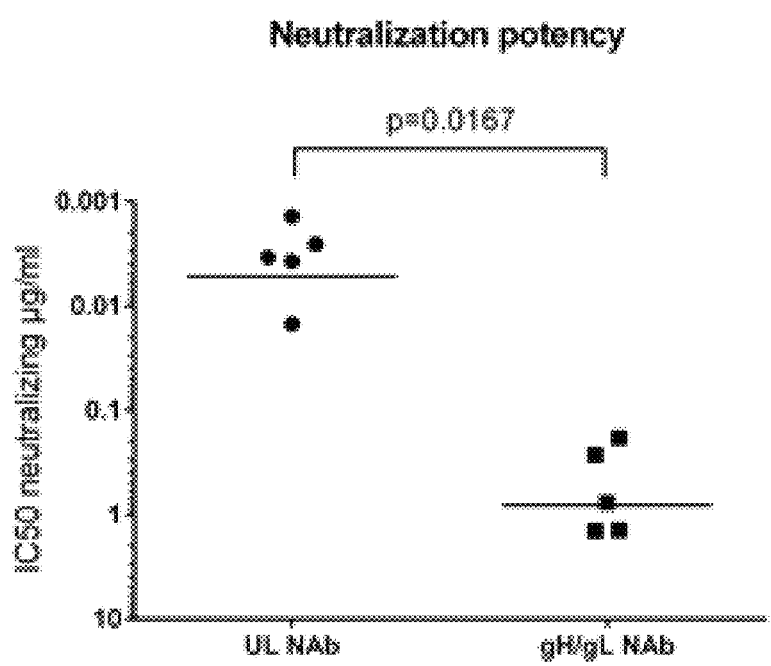

Example 7. Neutralization Potency of Vaccine-Induced NAbs May Correlate with Antibody Affinity It has been shown that a reduced risk for HCMV transmission to the fetus is associated with high affinity, highly neutralizing antibody responses (42, 73). Consequently, the affinity of the vaccine-induced NAbs to bind cell surface PC on MVA-PC infected BHK-21 cells was evaluated and whether the antibody affinity correlates with potency to neutralize HCMV was investigated. FIG. 6A shows a positive correlation between antibody affinity and neutralization potency taking into account all isolated NAbs ($r=0.743$, $p=0.014$). Consistent with the neutralization potency, higher binding affinity was observed with the PC-specific NAbs than with the anti-gH NAbs (FIG. 6A and Table 3). In addition, the highest affinity was observed with 1B2, which is the most potent NAb to block EpC/EnC entry identified (Table 3). However, despite a significant difference in neutralization potency between PC- and gH-specific NAbs ($p=0.0167$, FIG. 6C), the difference in binding affinity of the PC-specific NAbs and anti-gH NAbs was not significant ($p>0.05$, FIG. 6B). The EC50 values determined for the vaccine-derived NAbs were in the range of published values for HCMV NAbs observed by others (34). These findings provide evidence that the neutralization potency of vaccine-derived PC and gH-specific NAbs correlates with their ability to bind the PC.

Example 8. Vaccine-Derived PC- and gH-Specific NAbs Recognize Different Antigenic Target Sites It has been reported that human NAbs recognizing the PC target at least seven distinct antigenic sites (32, 33). In order to determine whether the vaccine-induced NAbs bind overlapping or non-overlapping target sites of the PC, the ability to cross-compete for binding to PC expressed in MVA-PC infected BHK-21 cells was evaluated. As shown in Table 4, binding competition was observed between the two PC-specific NAbs 1B2 and 12E2, indicating that 1B2 and 12E2 recognize overlapping target sites formed by UL128/130/131A. The same result was obtained with the PC-specific NAbs 54E11 and 21F6, demonstrating that these NAbs target similar binding sites constituted by UL130/131A. UL128/130/131A-specific NAbs and UL130/131A-specific NAbs did not compete for binding with each other or with the anti-UL128 NAb 13B5. Binding competitions between the anti-gH NAbs 62-11 and 62-100 and between anti-gH NAbs 21E9 and 2-80 were observed. Hence, 62-11 and 62-100 or 21E9 and 2-80 target similar antigenic sites on gH. In addition, 62-11 and 62-100 demonstrated ability to partially compete for binding with 21E9 and 2-80, suggesting that 62-11 and 62-100 share partially overlapping binding sites on gH with 21E9 and 2-80. In contrast to all other isolated gH NAbs, NAb 18F10 was not able to compete with any of the gH-specific NAbs. Overall three antigenic sites on the UL128/130/131A subunits and three antigenic sites on gH were identified (Table 4). The VH and VL genes from each NAb was sequenced as follows: mRNA was isolated from hybridoma cells and reverse transcribed into cDNA. Next, VH and VL regions were amplified by PCR, gel purified, ligated into a standard cloning vector and clones selected from LB plates. Multiple clones were selected for sequencing and the final sequence was confirmed by at least three identical sequencing results. Complementarity determining regions (CDRs) sequencing revealed that EpC/EnC NAbs 54E11 and 21F6, both binding to the same antigenic site on UL130/131A, are encoded by the same sequence (Table 5).

Although some of the NAbs competed for the same antigenic site, unique variable heavy ($V_H$) and light ($V_L$) chain sequences for most of the NAbs were determined (Table 5). Despite sharing the same antigenic binding site on UL128/130/131A, NAbs 1B2 and 12E2 have completely different CDR sequences. Of the gH NAbs competing for the same antigenic site, 62-11 and 62-100 share similar, but not identical, CDR sequences. Identical $V_H$ and $V_L$ sequences were only observed for the two UL130/131A-specific NAbs 21F6 and 54E11. It was confirmed that 54E11 and 21F6 have different isotypes (Table 5), suggesting that these NAbs were derived from the same centroblast B cell after class switch recombination (74). A very limited number of point mutations in $V_H$ and $V_L$ sequences of the NAbs when compared to germ line sequences were identified (Table 5), suggesting that, at least in immunized mice, potent HCMV NAbs are already encoded by the germline with very low influence of affinity maturation. This data indicate that vaccine-derived NAbs recognize predominantly distinct antigenic target sites on the UL128/130/131A subunits or gH.

TABLE 4

NAb competition for binding to the PC

| | Unlabelled Ab | Binding Inhibition (%) Biotinilated Abs | | | | | | | | | | Antigenic site* |
|---|---|---|---|---|---|---|---|---|---|---|---|---|
| | | 1B2 | 54E11 | 21F6 | 12E2 | 13B5 | 18F10 | 21E9 | 62-11 | 62-100 | 2-80 | AP86 | |
| UL NAb | 1B2 | 100 | 0 | 0 | 100 | 0 | 0 | ND | ND | ND | ND | ND | 1 UL |
| | 54E11 | 0 | 100 | 100 | 0 | 0 | 0 | ND | ND | ND | ND | ND | 2 UL |
| | 21F6 | 0 | 100 | 100 | 0 | 0 | 0 | ND | ND | ND | ND | ND | 2 UL |
| | 12E2 | 100 | 0 | 0 | 100 | 0 | 0 | ND | ND | ND | ND | ND | 1 UL |
| | 13B5 | 0 | 0 | 0 | 0 | 100 | 0 | ND | ND | ND | ND | ND | 3 UL |
| gH NAb | 18F10 | 0 | 0 | 0 | 0 | 0 | 100 | 0 | 0 | 0 | 0 | 100 | 1 gH |
| | 21E9 | ND | ND | ND | ND | ND | 0 | 100 | 32 | 28 | 100 | 0 | 2 gH |
| | 62-11 | ND | ND | ND | ND | ND | 0 | 46 | 100 | 100 | 54 | 0 | 3 gH |
| | 62-100 | ND | ND | ND | ND | ND | 0 | 51 | 100 | 100 | 57 | 0 | 3 gH |
| | 2-80 | ND | ND | ND | ND | ND | 0 | 100 | 43 | 40 | 100 | 0 | 2 gH |
| | AP86 | ND | ND | ND | ND | ND | 100 | 0 | 0 | 0 | 0 | 100 | 1 gH |

ND = not done;
*antigenic site numbers are arbitrarily assigned based on cross-competition.

TABLE 5

NAb binding affinity and sequence analysis

| Antibody | Specificity | Isotype (class and subclass, light chain type) | VL/VH CDR3 sequences | | VL % | | | VH %* | | |
|---|---|---|---|---|---|---|---|---|---|---|
| | | | VL CDR3 | VH CDR3 | aa | Mut aa | % mut | aa | Mut aa | % mut |
| 1B2 | UL128/130/131 | IgG1, k | QQSNRWPWT | ARGWLLPVFAY | 107 | 5 | 4.7 | 118 | 4 | 3.4 |
| 54E11 | UL130/131 | IgG1, k | QQYSKLPYT | AREHYYGINPLLGC | 107 | 1 | 0.9 | 121 | 1 | 0.8 |
| 21F6 | UL130/131 | IgG2a, k | QQYSKLPYT | AREHYYGINPLLGC | 107 | 1 | 0.9 | 121 | 1 | 0.8 |
| 12E2 | UL128/130/131 | IgG2a, k | QHSRELPWT | VRPKRDFQYLYAMDY | 111 | 2 | 1.8 | 122 | 6 | 4.9 |
| 13B5 | UL128 | IgG2a, k | QNGHTFPPT | VRSLYDYDEGYYFDS | 107 | 4 | 3.7 | 123 | 16 | 13.0 |
| 18F10 | gH | IgG1, k | SQSTHVPYT | ARTGYFDV | 112 | 6 | 5.4 | 116 | 9 | 7.8 |
| 21E9 | gH | IgG2a, k | QQDYSSPWT | ARKGYYGSSGYFDY | 107 | 1 | 0.9 | 121 | 2 | 1.7 |
| 62-11 | gH | IgG1, k | QQYSKLPYT | SNGYSSFAY | 107 | 2 | 1.9 | 116 | 7 | 6.0 |
| 62-100 | gH | IgG1, k | QQSNSWPLT | SNGYSSFAY | 107 | 2 | 1.9 | 116 | 7 | 6.0 |
| 2-80 | gH | IgG2a, k | QQSNEDPLT | ARRGDGLYSMDY | 111 | 2 | 1.8 | 119 | 2 | 1.7 |

*Mutations brought in by the VH primers (68) were excluded.

Example 9. NAb 18F10 Binds an Immunodominant Linear Epitope on gH

Figure 7A:
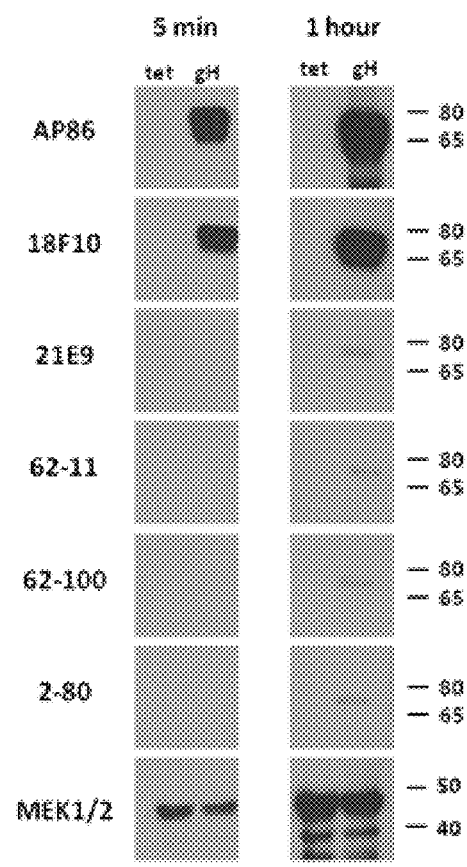
FIGS. 7A and 7B show recognition of linear gH by vaccine derived gH-specific NAb.
Figure 7B:
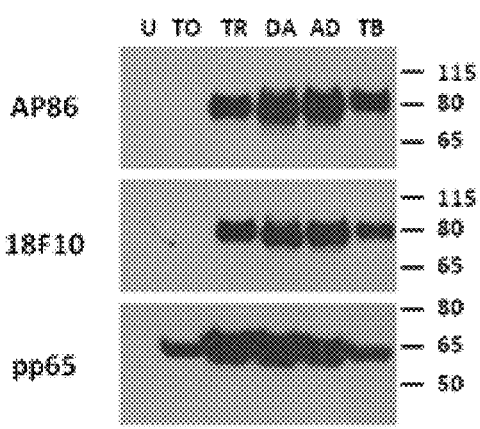
Figure 9:
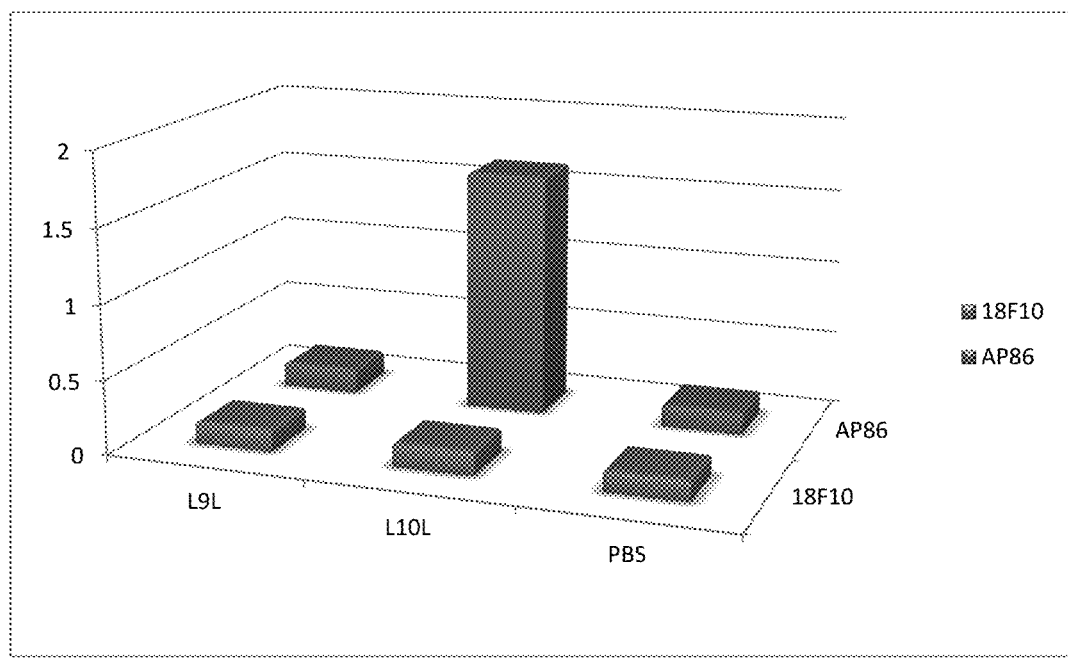
FIG. 9 shows an ELISA assay performed by coating the wells with L9L (2 µg/mL), L10L (2 µg/mL) or PBS and incubating with anti-gH NAbs 18F10 or AP86 (2 µg/mL).

Since all identified gH-specific NAbs showed binding to gH by intracellular and cell surface staining even in the absence of gL (FIG. 2 and Table 2), whether the anti-gH NAbs bind linear or conformational epitopes on the gH protein was investigated. Therefore, the NAb was tested to recognize gH expressed from adenoviral vectors (AdV) using immunoblot analysis under denaturing conditions. As a control, the well-characterized anti-gH antibody AP86 was used, which is known to bind the linear immunodominant neutralizing epitope of gH (34-LDPHAFHLLL-43) (SEQ ID NO: 184) (59). Compared to AP86, only anti-gH NAb 18F10 efficiently recognized denatured gH, while all other gH-specific NAbs demonstrated only minimal ability to react with the linear form of gH (FIG. 7A). Based on this observation, it is possible that 18F10 like AP86 binds the linear immunodominant epitope of gH. To obtain further evidence for the similar antigen recognition properties of AP86 and 18F10, the neutralization potency of 18F10 and AP86 to block TB40/E infection of MRC-5 FB or ARPE-19 EpC was determined. Different from previous reports (59), although comparable to what was observed for vaccine-derived anti-gH NAb 18F10, AP86 was unable to neutralize entry of TB40/E into MRC-5 FB (Table 3). However, AP86 had comparable potency to 18F10 to prevent entry of TB40/E into ARPE-19 cells (IC50 1 µg/ml. Table 3). Since the AP86 epitope is present in most HCMV strains but not in Towne due to a gap and a point mutation (34-LD*KAFHLLL-43) (SEQ ID NO: 185) (59), 18F10 and AP86 for recognition of gH in Towne, T R, Davis, AD169 and TB40/E infected MRC-5 cells were evaluated via immunoblot. Both 18F10 and AP86 bound to gH from TR, Davis, AD169 and TB40, but they did not bind to Towne gH (FIG. 7B). Finally, cross competition of AP86 with 18F10 was evaluated and, as a control, also with all other gH-specific NAbs to recognize the PC in MVA-PC infected BHK-21 cells. Only 18F10 competed with AP86 for binding to the PC (Table 4). An ELISA assay was performed with the TB40 specific peptide, L10L, (i.e., (LDPHAFHLLL) (SEQ ID NO: 184)) that binds AP86 and with the Towne specific peptide, L9L, (i.e., (LD*KAFHLLL) (SEQ ID NO: 185)) that does not bind AP85. Results show that despite binding to the same antigenic site, 18F10 and AP86 did not bind the same epitope (see FIG. 9). Therefore 18F10 binds to a novel epitope that was not previously described. These data indicate that binding of the vaccine-derived anti-gH NAb 18F10 overlaps with the linear immunodominant epitope of HCMV gH and, hence, provides further evidence that the NAb responses induced by MVA-PC are similar to those induced during natural HCMV infection.

Figure 8A:
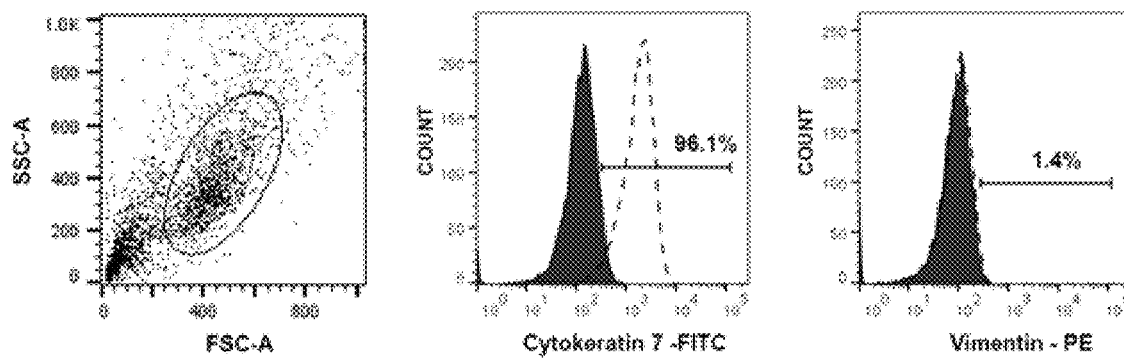
FIGS. 8A and 8B show neutralization of CTB infection by vaccine-derived NAb.
Figure 8B:
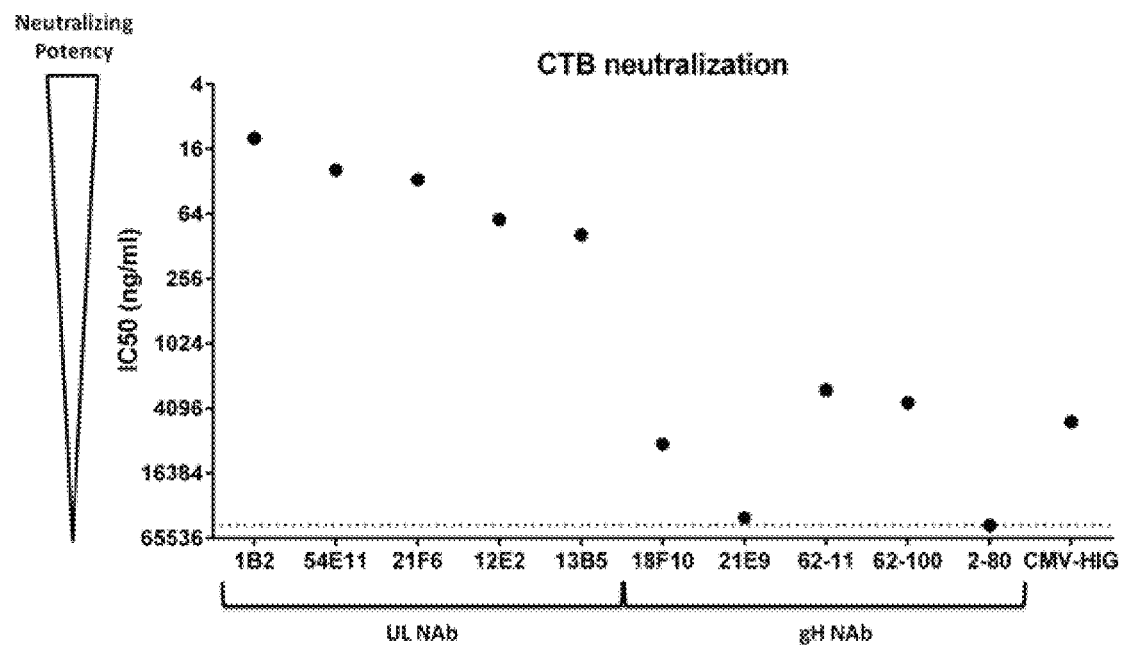

Example 10. PC-Specific NAbs are More Potent than Anti-gH NAbs to Block HCMV Infection of Placental CTB CTB are thought to be the key placental cells HCMV utilizes to cross the fetal-maternal interface (40, 41, 46). In order to determine whether the vaccine-derived NAbs can block HCMV infection of CTB, a standard microneutralization assay was used to evaluate the neutralization potency against TB40/E using freshly prepared primary CTB from term placentae. As shown in FIG. 8A, the prepared cell populations were almost exclusively positive for cytokeratin 7 and negative for vimentin, showing that almost all cells were primary CTB, while only minor proportions accounted for mesenchymal cells (57, 58, 75). Consistent with the potency to neutralize HCMV entry and cell-to-cell spread, the neutralization potency of all PC NAbs measured on CTB was significantly higher than that of the NAbs targeting gH or CMV-HIG (FIG. 8B and Table 3). Compared to all NAbs isolated, the highest potency to block CTB infection was demonstrated with PC-specific NAb 1B2, which had also the most potent ability to inhibit HCMV entry into EpC and spreading in these cells. In contrast, anti-gH NAbs showed lower level neutralization potency against TB40/E on CTB that was only comparable to that of CMV-HIG. Some anti-gH NAbs were even unable to prevent TB40/E infection of CTB at the highest investigated antibody concentration (50 µg/ml). These data demonstrated that NAbs specific for the UL128/130/131A subunits of the PC confer higher protection against HCMV infection of primary CTB from term placentae than NAbs targeting gH or antibody preparations from HCMV+ individuals.

Example 11. NAb 13B5 Binding Site

The NAb 13B5 Binding Site within UL128 is at Minimum 13 Amino Acids in Length.

Linear B cell epitopes vary greatly in length and range from 5-22 amino acids (1, 2) with an average of 15 (3). In order to define the amino acid sequence within UL128 that constitute the 13B5 epitope, binding of 13B5 to N-terminal and C-terminal truncated sequences of peptide 40 of the UL128 peptide library was evaluated via ELISA. Peptide 40 is composed of amino acids 157-KRLDVCR-AKMGYMLQ-171 of the UL128 protein, and demonstrated strongest binding to the 13B5 antibody and hence was likely to contain the minimal 13B5 binding sequence. Removal of the N-terminal amino acid K and sequential removal the four following amino acids (RLDV) from the C-terminus of peptide 40 resulted in dramatically reduced 13B5 binding. Complete loss of 13B5 binding was observed by removing six or more N-terminal amino acids from peptide 40 (FIG. 10A). Truncation of the two C-terminal amino acids LQ from peptide 40 did not show a reduction in 13B5 binding, though slightly decreased 13B5 binding was observed by additionally removing the M from the peptide 40 C-terminus (FIG. 10B). 13B5 binding was substantially decreased by removing the four C-terminal amino acids YMLQ from peptide 40, and was completely lost when five or more C-terminal amino acids of peptide 40 were removed (FIG. 10B). These results indicated that a 13 amino acids long peptide sequence ranging from K-157 to M-169 (KRLDVCRAKMGYM) of the UL128 protein is necessary and sufficient for efficient 13B5 binding. To investigate further whether additional amino acid residues localized at the N-terminus of K-157 of UL128 are critical for 13B5 recognition, 13B5 binding to peptides composed of the defined minimal 13B5 binding site was compared with peptides comprising the 13B5 binding site and one or two additional amino acids (K-155 and H-156) of UL128 added to the N-terminus. As shown in FIG. 10C, addition of the N-terminal amino acids (KH) to the 13B5 target sequence only minimally improved binding of 13B5 antibody, suggesting that these amino acids are not critical for 13B5 binding but they may slightly improve the interaction of the 13B5 antibody and its target site. In sum, these results suggest that NAb 13B5 targets a 13 amino acid long linear epitope sequence at the C-terminus of UL128 that is composed of residues 157-KRLDVCRAKMGYM-169 of the protein.

Most Residues of the 13B5 Target Site within UL128 are Critical for Antibody Binding.

Figure 10D:
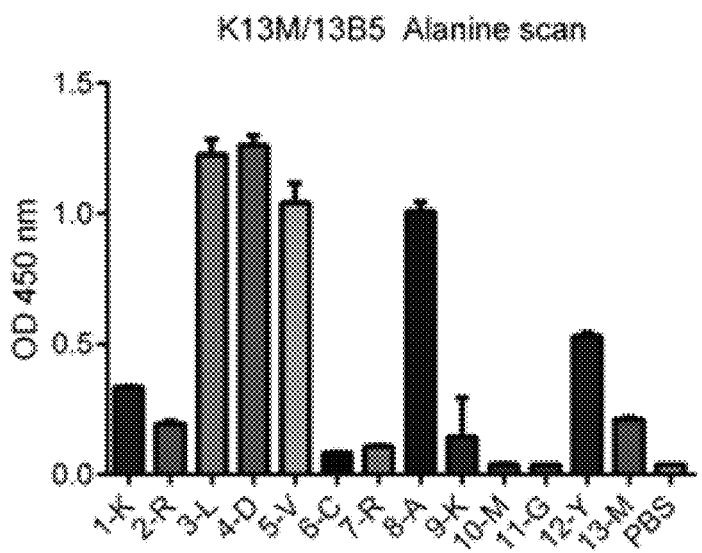

In order to define the amino acid residues of the 13B5 target site within UL128 that are critical for antibody binding, each residue of the defined 13 amino acid long 13B5 binding site was serially substituted with alanine residues, and the influence of these changes on 13B5 binding was evaluated. FIG. 10D shows the individual sequences of the mutated peptides as well as the testing of 13B5 binding to these peptides via ELISA. Note that peptide K13M is identical to the original sequence of the 13B5 binding site within UL128 (157-KRLDVCRAKMGYM-169). This peptide comprises an internal alanine and hence was used as control in the ELISA for testing 13B5 binding. Consistent with results obtained with truncation libraries, alanine substitution of the N-terminal K and C-terminal Y or M of K13M significantly reduced binding of the 13B5 antibody. Similarly, substituting most of the internal amino acids (C, R, K, M, and G) of K13M with alanine residues resulted in dramatically reduced or complete loss of 13B5 binding. In contrast, 13B5 binding was not impaired when one of the internal residues L, D, and V of K13M were substituted. In addition, substitution of L or D within K13M slightly increased 13B5 binding when compared to the original K13M sequence, suggesting that these amino acid substitutions slightly improved the interaction of 13B5 and its target sequence. Interestingly, the internal C within K13M that appeared essential for 13B5 binding corresponds to amino acid C-162 of UL128 that has previously been shown to form a disulfide bridge with gL in the PC (4). This suggests that NAb 13B5 targets a sequence within UL128 that is critical for interaction of the PC subunits. In sum, these results indicate that most of the amino acids of the 13B5 target site within UL128 are directly involved in the interaction with the 13B5 antibody, while three residues within the target site appear not to be involved directly in 13B5 binding.

Example 12. Validation of Small Peptides

Peptide Construction Based on the 13B5 Binding Site to Test Antibody Induction.

Figure 11A:
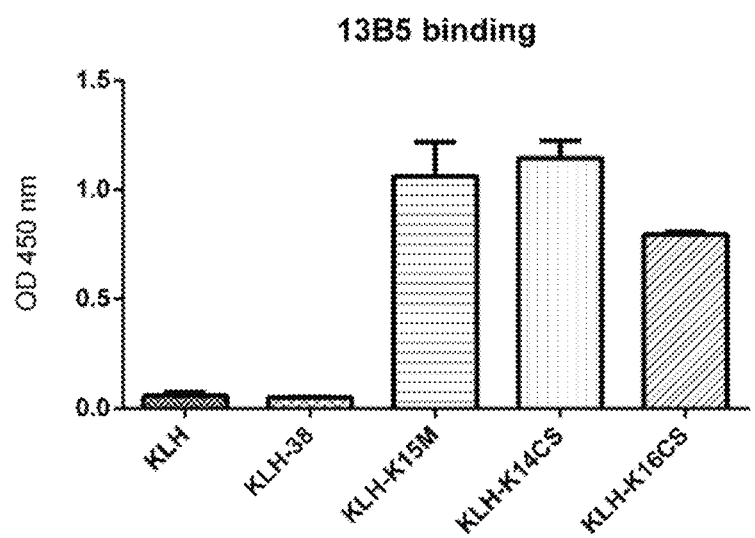
FIGS. 11A-11C show binding and neutralizing antibody induction by peptides based on the 13B5 epitope sequence.

To determine whether the UL128 binding site of NAb 13B5 is a neutralizing determinant, keyhole limpet hemocyanin (KLH)-coupled peptides based on the 13B5 binding site were evaluated for immunogenicity to elicit NAb in mice. For this, three different KLH-coupled peptide constructs were generated based on the 13B5 target sequence. In one construct, termed KLH-K15M (i.e., KLH-coupled SEQ ID NO: 179), KLH was coupled to the minimal 13B5 target sequence (K13M) via the existing internal C-162, and two additional residues of UL128 were added to the peptide C-terminus, which appeared to increase slightly the binding of 13B5 antibody. The second construct named KLH- K14CS (i.e., KLH-coupled SEQ ID NO: 180) was generated by coupling of KLH via a C-terminally added C residue to K13M in which the internal C-162 of the minimal 13B5 target sequence was substituted with a serine. The third construct, termed KLH-K16CS (i.e., KLH-coupled SEQ ID NO: 181), was generated in a similar way as the second construct (KLH-K14CS), except that it comprised two additional amino acid residues of UL128 at the N-terminus similar to the first construct (KLH-K15M). C to S amino acid substitutions in the second and third construct (KLH-K14CS, KLH-K16CS) were chosen because of the similarity in steric occupancy between these two residues. As shown in FIG. 11A, all KLH construct showed strong binding of 13B5 antibody, indicating that the KLH coupling and amino substitutions did not alter the interaction of the 13B5 target sequence with the 13B5 antibody. In addition, serine substitution of the internal C-162 in peptide K13M with minimal 13B5 target site—not coupled to KLH—and subsequent addition of a C-terminal cysteine did not result in a decrease of 13B5 binding when compared with the original K13M peptide. However, C-162 to serine substitution in K13M without adding a C-terminal cysteine dramatically decreased 13B5 binding, which is consistent with our findings with the alanine scanning procedure (see FIG. 10D). This suggests that the cysteine residue of the 13B5 target site is essential for 13B5 binding, but its location within the target site at position 162 of the UL128 protein sequence might not be absolutely fundamental for the antibody binding. As control, a peptide construct C-terminally coupled to KLH (KLH-38) consisting of library peptide 38 that was only partially overlapping with the 13B5 target site was generated. This peptide was similar to a recently tested UL128 peptide that has failed to stimulate NAb in rabbits (5). KLH-38 was unable to bind 13B5 antibody, supporting its use as a control construct. In sum, these results indicated that all KLH-coupled peptide constructs presented intact 13B5 target sites.

Figure 11B:
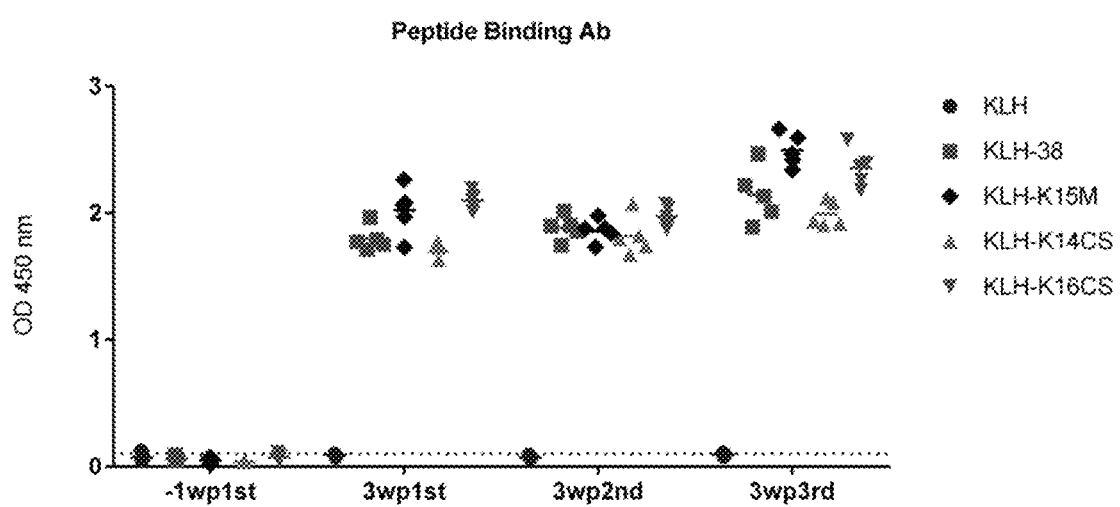
Figure 11C:
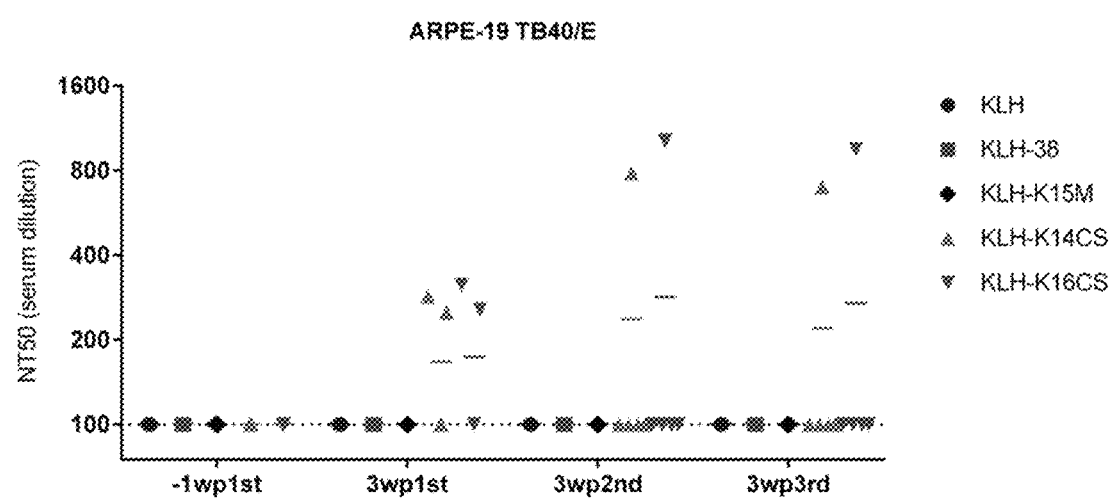

Peptides Based on the 13B5 Target Site have Ability to Elicit NAb in Mice. For testing whether the generated KLH coupled peptide constructs based on the 13B5 target site (KLH-K15M, KLH-K14CS, KLH-K16CS) have ability to elicit NAb in vivo, Balb/c mice were intraperitoneally immunized three times four weeks apart with the peptide constructs admixed in Freund's adjuvant. Serum binding antibodies and NAb were determined one week before and three weeks after each immunization. Binding antibodies of the individual groups were determined via ELISA using peptides as target antigens that were used for immunization (FIG. 11B). NAb titer at which 50% infection (NT50) was inhibited were determined by micro neutralization assay using ARPE-19 EC as cell substrate and HCMV strain TB40/E for infection (FIG. 11C). For control, mice were immunized with KLH only or KLH-38 with C-terminal UL128 peptide sequence that only partially overlapped with the 13B5 target site. As shown in FIG. 11B, all mice immunized with the peptide constructs developed binding antibodies against the peptide sequence with which they were vaccinated after the first immunization. These responses were not or only minimally boosted by a second and third immunization. In addition, Western Blot analysis of UL128 expressed from Ad vectors showed that mice immunized with KLH-K15M, KLH-K14CS, KLH-K16CS developed antibodies that recognized denatured UL128. NAb responses with NT50 titers ranging from 200 to 300 were detectable after the first immunization in only two out of five animals in each vaccine group immunized with KLH-K14CS or KLH-K16CS (FIG. 11C). These responses were boosted in only one animal in each of the KLH-K14CS or KLH-K16CS vaccine groups, reaching NT50 titers of 800 to 1200. These titers remained stable after the third immunization. In the two other animals that developed NAb after the first immunization, NAb declined and were undetectable after the booster immunizations. None of the animals immunized with the peptide construct KLH-K15M, control construct KLH-38, or KLH only developed NAb. These results indicate that peptides based on the 13B5 target site in which the internal cysteine residue was substituted by a serine and KLH was coupled via an additional cysteine residue to the C-terminus had ability to elicit NAb in mice. In contrast, peptides composed of the 13B5 target site that were coupled to KLH via the existing internal C-162 did not show immunogenicity for NAb induction. These results support that the identified 13B5 target site constitutes a neutralizing epitope within UL128.

REFERENCES

The references, patents and published patent applications listed below, and all references cited in the specification above are hereby incorporated by reference in their entireties, as if fully set forth herein.

1. Ludwig A, Hengel H. 2009. Epidemiological impact and disease burden of congenital cytomegalovirus infection in Europe. Euro Surveill 14:26-32.
2. Manicklal S, Emery V C, Lazzarotto T, Boppana S B, Gupta R K. 2013. The "silent" global burden of congenital cytomegalovirus. Clin Microbiol Rev 26:86-102.
3. Ornoy A, Diav-Citrin O. 2006. Fetal effects of primary and secondary cytomegalovirus infection in pregnancy. Reprod Toxicol 21:399-409.
4. Cannon M J, Davis K F. 2005. Washing our hands of the congenital cytomegalovirus disease epidemic. BMC Public Health 5:70.
5. Britt W. 2015. Controversies in the natural history of congenital human cytomegalovirus infection: the paradox of infection and disease in offspring of women with immunity prior to pregnancy. Med Microbiol Immunol doi: 10.1007/s00430-015-0399-9.
6. Kenneson A, Cannon M J. 2007. Review and meta-analysis of the epidemiology of congenital cytomegalovirus (CMV) infection. Rev Med Virol 17:253-276.
7. Cannon M J, Westbrook K, Levis D, Schleiss M R, Thackeray R, Pass R F. 2012. Awareness of and behaviors related to child-to-mother transmission of cytomegalovirus. Prev Med 54:351-357.
8. Pass R F, Anderson B. 2014. Mother-to-Child Transmission of Cytomegalovirus and Prevention of Congenital Infection. J Pediatric Infect Dis Soc 3:S2-S6.
9. Lazzarotto T, Gabrielli L, Guerra B, Cervi F, Piccirilli G, Simonazzi G, Chiereghin A, Bellini F, Landini M P. 2014. Diagnosis and prognosis of congenital CMV infection: a case report and review of the literature. Scand J Clin Lab Invest Suppl 244:34-40; discussion 39.
10. Pereira L, Petitt M, Fong A, Tsuge M, Tabata T, Fang-Hoover J, Maidji E, Zydek M, Zhou Y, Inoue N, Loghavi S, Pepkowitz S, Kauvar L M, Ogunyemi D. 2014. Intrauterine growth restriction caused by underlying congenital cytomegalovirus infection. J Infect Dis 209:1573-1584.
11. La Rosa C, Diamond D J. 2012. The immune response to human CMV. Future Virol 7:279-293.
12. Khanna R, Diamond D J. 2006. Human cytomegalovirus vaccine: time to look for alternative options. Trends Mol Med 12:26-33.

13. Dasari V, Smith C, Khanna R. 2013. Recent advances in designing an effective vaccine to prevent cytomegalovirus-associated clinical diseases. Expert Rev Vaccines 12:661-676.
14. Stratton K R, Durch J S, Lawrence R S. 2000. Vaccines for the 21st Century: A Tool for Decisionmaking, Washington (DC).
15. Krause P R, Bialek S R, Boppana S B, Griffiths P D, Laughlin C A, Ljungman P, Mocarski E S, Pass R F, Read J S, Schleiss M R, Plotkin S A. 2013. Priorities for CMV vaccine development. Vaccine 32:4-10.
16. Griffiths P, Plotkin S, Mocarski E, Pass R, Schleiss M, Krause P, Bialek S. 2013. Desirability and feasibility of a vaccine against cytomegalovirus. Vaccine 31 Suppl 2:B197-203.
17. Pass R F, Zhang C, Evans A, Simpson T, Andrews W, Huang M L, Corey L, Hill J, Davis E, Flanigan C, Cloud G. 2009. Vaccine prevention of maternal cytomegalovirus infection. N Engl J Med 360:1191-1199.
18. Pass R F. 2009. Development and evidence for efficacy of CMV glycoprotein B vaccine with MF59 adjuvant. J Clin Virol 46 Suppl 4:S73-76.
19. Griffiths P D, Stanton A, McCarrell E, Smith C, Osman M, Harber M, Davenport A, Jones G, Wheeler D C, O'Beirne J, Thorburn D, Patch D, Atkinson C E, Pichon S, Sweny P, Lanzman M, Woodford E, Rothwell E, Old N, Kinyanjui R, Haque T, Atabani S, Luck S, Prideaux S, Milne R S, Emery V C, Burroughs A K. 2011. Cytomegalovirus glycoprotein-B vaccine with MF59 adjuvant in transplant recipients: a phase 2 randomised placebo-controlled trial. Lancet 377:1256-1263.
20. Bernstein D I. 2014. Safety and Efficacy of a Cytomegalovirus Glycoprotein B (gB) Vaccine in Adolescent Girls, abstr IDWeek2014 Philadelphia, Pa., Friday, Oct. 10, 2014.
21. Wang D, Shenk T. 2005. Human cytomegalovirus virion protein complex required for epithelial and endothelial cell tropism. Proc Natl Acad Sci USA 102:18153-18158.
22. Ryckman B J, Jarvis M A, Drummond D D, Nelson J A, Johnson D C. 2006. Human cytomegalovirus entry into epithelial and endothelial cells depends on genes UL128 to UL150 and occurs by endocytosis and low-pH fusion. J Virol 80:710-722.
23. Vanarsdall A L, Johnson D C. 2012. Human cytomegalovirus entry into cells. Curr Opin Virol 2:37-42.
24. Ryckman B J, Chase M C, Johnson D C. 2008. HCMV gH/gL/UL128-131 interferes with virus entry into epithelial cells: evidence for cell type-specific receptors. Proc Natl Acad Sci USA 105:14118-14123.
25. Hahn G, Revello M G, Patrone M, Percivalle E, Campanini G, Sarasini A, Wagner M, Gallina A, Milanesi G, Koszinowski U, Baldanti F, Gerna G. 2004. Human cytomegalovirus UL131-128 genes are indispensable for virus growth in endothelial cells and virus transfer to leukocytes. J Virol 78:10023-10033.
26. Wang D, Yu Q C, Schroer J, Murphy E, Shenk T. 2007. Human cytomegalovirus uses two distinct pathways to enter retinal pigmented epithelial cells. Proc Natl Acad Sci USA 104:20037-20042.
27. Wille P T, Knoche A J, Nelson J A, Jarvis M A, Johnson D C. 2010. A human cytomegalovirus gO-null mutant fails to incorporate gH/gL into the virion envelope and is unable to enter fibroblasts and epithelial and endothelial cells. J Virol 84:2585-2596.
28. Vanarsdall A L, Chase M C, Johnson D C. 2011. Human cytomegalovirus glycoprotein gO complexes with gH/gL, promoting interference with viral entry into human fibroblasts but not entry into epithelial cells. J Virol 85:11638-11645.
29. Ciferri C, Chandramouli S, Donnarumma D, Nikitin P A, Cianfrocco M A, Gerrein R, Feire A L, Barnett S W, Lilja A E, Rappuoli R, Norais N, Settembre E C, Carfi A. 2015. Structural and biochemical studies of HCMV gH/gL/gO and Pentamer reveal mutually exclusive cell entry complexes. Proc Natl Acad Sci U S A 112:1767-1772.
30. Li G, Nguyen C C, Ryckman B J, Britt W J, Kamil J P. 2015. A viral regulator of glycoprotein complexes contributes to human cytomegalovirus cell tropism. Proc Natl Acad Sci USA 112:4471-4476.
31. Zhou M, Lanchy J M, Ryckman B J. 2015. Human cytomegalovirus gH/gL/gO promotes the fusion step of entry into all cell types whereas gH/gL/UL128-131 broadens virus tropism through a distinct mechanism. J Virol doi:10.1128/JVI.01325-15.
32. Macagno A, Bernasconi N L, Vanzetta F, Dander E, Sarasini A, Revello M G, Gerna G, Sallusto F, Lanzavecchia A. 2010. Isolation of human monoclonal antibodies that potently neutralize human cytomegalovirus infection by targeting different epitopes on the gH/gL/UL128-131A complex. J Virol 84:1005-1013.
33. Kabanova A, Perez L, Lilleri D, Marcandalli J, Agatic G, Becattini S, Preite S, Fuschillo D, Percivalle E, Sallusto F, Gerna G, Corti D, Lanzavecchia A. 2014. Antibody-driven design of a human cytomegalovirus gHgLpUL128L subunit vaccine that selectively elicits potent neutralizing antibodies. Proc Natl Acad Sci USA 111:17965-17970.
34. Freed D C, Tang Q, Tang A, Li F, He X, Huang Z, Meng W, Xia L, Finnefrock A C, Durr E, Espeseth A S, Casimiro D R, Zhang N, Shiver J W, Wang D, An Z, Fu T M. 2013. Pentameric complex of viral glycoprotein H is the primary target for potent neutralization by a human cytomegalovirus vaccine. Proc Natl Acad Sci USA 110: E4997-5005.
35. Wen Y, Monroe J, Linton C, Archer J, Beard C W, Barnett S W, Palladino G, Mason P W, Carfi A, Lilja A E. 2014. Human cytomegalovirus gH/gL/UL128/UL130/UL131A complex elicits potently neutralizing antibodies in mice. Vaccine 32:3796-3804.
36. Wussow F, Chiuppesi F, Martinez J, Campo J, Johnson E, Flechsig C, Newell M, Tran E, Ortiz J, La Rosa C, Herrmann A, Longmate J, Chakraborty R, Barry P A, Diamond D J. 2014. Human cytomegalovirus vaccine based on the envelope gH/gL pentamer complex. PLoS Pathog 10:e1004524.
37. Cui X, Meza B P, Adler S P, McVoy M A. 2008. Cytomegalovirus vaccines fail to induce epithelial entry neutralizing antibodies comparable to natural infection. Vaccine 26:5760-5766.
38. Gerna G, Sarasini A, Patrone M, Percivalle E, Fiorina L, Campanini G, Gallina A, Baldanti F, Revello MG. 2008. Human cytomegalovirus serum neutralizing antibodies block virus infection of endothelial/epithelial cells, but not fibroblasts, early during primary infection. J Gen Virol 89:853-865.
39. Revello M G, Gerna G. 2010. Human cytomegalovirus tropism for endothelial/epithelial cells: scientific background and clinical implications. Rev Med Virol 20:136-155.
40. Pereira L, Maidji E, McDonagh S, Tabata T. 2005. Insights into viral transmission at the uterine-placental interface. Trends Microbiol 13:164-174.

41. Pereira L, Maidji E. 2008. Cytomegalovirus infection in the human placenta: maternal immunity and developmentally regulated receptors on trophoblasts converge. Curr Top Microbiol Immunol 325:383-395.
42. Maidji E, McDonagh S, Genbacev O, Tabata T, Pereira L. 2006. Maternal antibodies enhance or prevent cytomegalovirus infection in the placenta by neonatal Fc receptor-mediated transcytosis. Am J Pathol 168:1210-1226.
43. McDonagh S, Maidji E, Chang H T, Pereira L. 2006. Patterns of human cytomegalovirus infection in term placentas: a preliminary analysis. J Clin Virol 35:210-215.
44. Tabata T, McDonagh S, Kawakatsu H, Pereira L. 2007. Cytotrophoblasts infected with a pathogenic human cytomegalovirus strain dysregulate cell-matrix and cell-cell adhesion molecules: a quantitative analysis. Placenta 28:527-537.
45. Trincado D E, Munro S C, Camaris C, Rawlinson W D. 2005. Highly sensitive detection and localization of maternally acquired human cytomegalovirus in placental tissue by in situ polymerase chain reaction. J Infect Dis 192:650-657.
46. Fisher S, Genbacev O, Maidji E, Pereira L. 2000. Human cytomegalovirus infection of placental cytotrophoblasts in vitro and in utero: implications for transmission and pathogenesis. J Virol 74:6808-6820.
47. Yamamoto-Tabata T, McDonagh S, Chang H T, Fisher S, Pereira L. 2004. Human cytomegalovirus interleukin-10 downregulates metalloproteinase activity and impairs endothelial cell migration and placental cytotrophoblast invasiveness in vitro. J Virol 78:2831-2840.
48. Rauwel B, Mariame B, Martin H, Nielsen R, Allart S, Pipy B, Mandrup S, Devignes M D, Evain-Brion D, Fournier T, Davrinche C. 2010. Activation of peroxisome proliferator-activated receptor gamma by human cytomegalovirus for de novo replication impairs migration and invasiveness of cytotrophoblasts from early placentas. J Virol 84:2946-2954.
49. Zydek M, Petitt M, Fang-Hoover J, Adler B, Kauvar L M, Pereira L, Tabata T. 2014. HCMV infection of human trophoblast progenitor cells of the placenta is neutralized by a human monoclonal antibody to glycoprotein B and not by antibodies to the pentamer complex. Viruses 6:1346-1364.
50. Kauvar L M, Liu K, Park M, DeChene N, Stephenson R, Tenorio E, Ellsworth S L, Tabata T, Petitt M, Tsuge M, Fang-Hoover J, Adler S P, Cui X, McVoy M A, Pereira L. 2015. A high-affinity native human antibody neutralizes human cytomegalovirus infection of diverse cell types. Antimicrob Agents Chemother 59:1558-1568.
51. Meyer H, Sutter G, Mayr A. 1991. Mapping of deletions in the genome of the highly attenuated vaccinia virus MVA and their influence on virulence. J Gen Virol 72 (Pt 5):1031-1038.
52. Harrer E, Bauerle M, Ferstl B, Chaplin P, Petzold B, Mateo L, Handley A, Tzatzaris M, Vollmar J, Bergmann S, Rittmaier M, Eismann K, Muller S, Kalden J R, Spriewald B, Willbold D, Harrer T. 2005. Therapeutic vaccination of HIV-1-infected patients on HAART with a recombinant HIV-1 nef-expressing MVA: safety, immunogenicity and influence on viral load during treatment interruption. Antivir Ther 10:285-300.
53. Johnson E L, Chakraborty R. 2012. Placental Hofbauer cells limit HIV-1 replication and potentially offset mother to child transmission (MTCT) by induction of immunoregulatory cytokines. Retrovirology 9:101.
54. Tang Z, Tadesse S, Norwitz E, Mor G, Abrahams V M, Guller S. 2011. Isolation of hofbauer cells from human term placentas with high yield and purity. Am J Reprod Immunol 66:336-348.
55. Johnson E L, Chu H, Byrareddy S N, Spearman P, Chakraborty R. 2015. Placental Hofbauer cells assemble and sequester HIV-1 in tetraspanin-positive compartments that are accessible to broadly neutralizing antibodies. J Int AIDS Soc 18:19385.
56. Maldonado-Estrada J, Menu E, Roques P, Barre-Sinoussi F, Chaouat G. 2004. Evaluation of Cytokeratin 7 as an accurate intracellular marker with which to assess the purity of human placental villous trophoblast cells by flow cytometry. J Immunol Methods 286:21-34.
57. Manoussaka M S, Jackson D J, Lock R J, Sooranna S R, Kumpel B M. 2005. Flow cytometric characterisation of cells of differing densities isolated from human term placentae and enrichment of villous trophoblast cells. Placenta 26:308-318.
58. Potgens A J, Gaus G, Frank H G, Kaufmann P. 2001. Characterization of trophoblast cell isolations by a modified flow cytometry assay. Placenta 22:251-255.
59. Urban M, Britt W, Mach M. 1992. The dominant linear neutralizing antibody-binding site of glycoprotein gp86 of human cytomegalovirus is strain specific. J Virol 66:1303-1311.
60. Britt W J, Auger D. 1985. Identification of a 65 000 dalton virion envelope protein of human cytomegalovirus. Virus Res 4:31-36.
61. Andreoni M, Faircloth M, Vugler L, Britt W J. 1989. A rapid microneutralization assay for the measurement of neutralizing antibody reactive with human cytomegalovirus. J Virol Methods 23:157-167.
62. Wussow F, Yue Y, Martinez J, Deere J D, Longmate J, Herrmann A, Barry P A, Diamond D J. 2013. A vaccine based on the rhesus cytomegalovirus UL128 complex induces broadly neutralizing antibodies in rhesus macaques. J Virol 87:1322-1332.
63. Wang Z, Martinez J, Zhou W, La Rosa C, Srivastava T, Dasgupta A, Rawal R, Li Z, Britt W J, Diamond D. 2010. Modified H5 promoter improves stability of insert genes while maintaining immunogenicity during extended passage of genetically engineered MVA vaccines. Vaccine 28:1547-1557.
64. Wang Z, La Rosa C, Maas R, Ly H, Brewer J, Mekhoubad S, Daftarian P, Longmate J, Britt W J, Diamond D J. 2004. Recombinant modified vaccinia virus Ankara expressing a soluble form of glycoprotein B causes durable immunity and neutralizing antibodies against multiple strains of human cytomegalovirus. J Virol 78:3965-3976.
65. Sinzger C, Hahn G, Digel M, Katona R, Sampaio K L, Messerle M, Hengel H, Koszinowski U, Brune W, Adler B. 2008. Cloning and sequencing of a highly productive, endotheliotropic virus strain derived from human cytomegalovirus TB40/E. J Gen Virol 89:359-368.
66. Zhang C. 2012. Hybridoma technology for the generation of monoclonal antibodies. Methods Mol Biol 901:117-135.
67. Even-Desrumeaux K, Chames P. 2012. Affinity determination of biotinylated antibodies by flow cytometry. Methods Mol Biol 907:443-449.
68. Fields C, O'Connell D, Xiao S, Lee G U, Billiald P, Muzard J. 2013. Creation of recombinant antigen-binding molecules derived from hybridomas secreting specific antibodies. Nat Protoc 8:1125-1148.

69. Boppana S B, Rivera L B, Fowler K B, Mach M, Britt W J. 2001. Intrauterine transmission of cytomegalovirus to infants of women with preconceptional immunity. N Engl J Med 344:1366-1371.
70. Fouts A E, Chan P, Stephan J P, Vandlen R, Feierbach B. 2012. Antibodies against the gH/gL/UL128/UL130/UL131 complex comprise the majority of the anti-cytomegalovirus (anti-CMV) neutralizing antibody response in CMV hyperimmune globulin. J Virol 86:7444-7447.
71. Scrivano L, Sinzger C, Nitschko H, Koszinowski U H, Adler B. 2011. HCMV spread and cell tropism are determined by distinct virus populations. PLoS Pathog 7:e1001256.
72. Cui X, Lee R, Adler S P, McVoy M A. 2013. Antibody inhibition of human cytomegalovirus spread in epithelial cell cultures. J Virol Methods 192:44-50.
73. Boppana S B, Britt W J. 1995. Antiviral antibody responses and intrauterine transmission after primary maternal cytomegalovirus infection. J Infect Dis 171: 1115-1121.
74. Li Z, Woo C J, Iglesias-Ussel M D, Ronai D, Scharff M D. 2004. The generation of antibody diversity through somatic hypermutation and class switch recombination. Genes Dev 18:1-11.
75. Frank H G, Genbacev O, Blaschitz A, Chen C P, Clarson L, Evain-Brion D, Gardner L, Malek A, Morrish D, Loke Y W, Tarrade A. 2000. Cell culture models of human trophoblast—primary culture of trophoblast—a workshop report. Placenta 21 Suppl A:S120-122.
76. Jacob C L, Lamorte L, Sepulveda E, Lorenz I C, Gauthier A, Franti M. 2013. Neutralizing antibodies are unable to inhibit direct viral cell-to-cell spread of human cytomegalovirus. Virology 444:140-147.
77. Buscher N, Paulus C, Nevels M, Tenzer S, Plachter B. 2015. The proteome of human cytomegalovirus virions and dense bodies is conserved across different strains. Med Microbiol Immunol 204:285-293.

Van Regenmortel M H. 2006. Immunoinformatics may lead to a reappraisal of the nature of B cell epitopes and of the feasibility of synthetic peptide vaccines. J Mol Recognit 19:183-187.

Singh H, Ansari H R, Raghava G P. 2013. Improved method for linear B-cell epitope prediction using antigen's primary sequence. PLoS One 8:e62216.

Kringelum J V, Nielsen M, Padkjaer S B, Lund O. 2013. Structural analysis of B-cell epitopes in antibody:protein complexes. Mol Immunol 53:24-34.

Ciferri C, Chandramouli S, Donnarumma D, Nikitin P A, Cianfrocco M A, Gerrein R, Feire A L, Barnett S W, Lilja A E, Rappuoli R, Norais N, Settembre E C, Carfi A. 2015. Structural and biochemical studies of HCMV gH/gL/gO and Pentamer reveal mutually exclusive cell entry complexes. Proc Natl Acad Sci USA 112:1767-1772.

Saccoccio F M, Sauer A L, Cui X, Armstrong A E, Habib el S E, Johnson D C, Ryckman B J, Klingelhutz A J, Adler S P, McVoy M A. 2011. Peptides from cytomegalovirus UL130 and UL131 proteins induce high titer antibodies that block viral entry into mucosal epithelial cells. Vaccine 29:2705-2711.

What is claimed is:

1. A method of preventing cell-to-cell spread of CMV, syncytia formation in epithelial cells, or both in a subject, comprising administering to the subject an effective amount of a composition comprising a vaccine-derived neutralizing antibody (NAb) against cytomegalovirus (CMV), which the vaccine-derived NAb is selected from the group consisting of:

(a) an antibody sharing at least 90% identity to the antibody comprising a variable heavy region comprising a CDR1$_{VH}$ sequence of SEQ ID NO: 3, a CDR2$_{VH}$ sequence of SEQ ID NO: 4, and a CDR3$_{VH}$ sequence of SEQ ID NO: 5; and a variable light region comprising a CDR1$_{VL}$ sequence of SEQ ID NO: 6, a CDR2$_{VL}$ sequence of SEQ ID NO: 7, and a CDR3$_{VL}$ sequence of SEQ ID NO: 8;

(b) an antibody sharing at least 90% identity to the antibody comprising a variable heavy region comprising a CDR1$_{VH}$ sequence of SEQ ID NO: 11, a CDR2$_{VH}$ sequence of SEQ ID NO: 12, and a CDR3$_{VH}$ sequence of SEQ ID NO: 13; and a variable light region comprising a CDR1$_{VL}$ sequence of SEQ ID NO: 14, a CDR2$_{VL}$ sequence of SEQ ID NO: 15, and a CDR3$_{VL}$ sequence of SEQ ID NO: 16;

(C) an antibody sharing at least 90% identity to the antibody comprising a variable heavy region comprising a CDR1$_{VH}$ sequence of SEQ ID NO: 19, a CDR2$_{VH}$ sequence of SEQ ID NO: 20, and a CDR3$_{VH}$ sequence of SEQ ID NO: 21; and a variable light region comprising a CDR1$_{VL}$ sequence of SEQ ID NO: 22, a CDR2$_{VL}$ sequence of SEQ ID NO: 23, and a CDR3$_{VL}$ sequence of SEQ ID NO: 24;

(d) an antibody sharing at least 90% identity to the antibody comprising a variable heavy region comprising a CDR1$_{VH}$ sequence of SEQ ID NO: 27, a CDR2$_{VH}$ sequence of SEQ ID NO: 28, and a CDR3$_{VH}$ sequence of SEQ ID NO: 29; and a variable light region comprising a CDR1$_{VL}$ sequence of SEQ ID NO: 30, a CDR2$_{VL}$ sequence of SEQ ID NO: 31, and a CDR3$_{VL}$ sequence of SEQ ID NO: 32;

(e) an antibody sharing at least 90% identity to the antibody comprising a variable heavy region comprising a CDR1$_{VH}$ sequence of SEQ ID NO: 35, a CDR2$_{VH}$ sequence of SEQ ID NO: 36, and a CDR3$_{VH}$ sequence of SEQ ID NO: 37; and a variable light region comprising a CDR1$_{VL}$ sequence of SEQ ID NO: 38, a CDR2$_{VL}$ sequence of SEQ ID NO: 39, and a CDR3$_{VL}$ sequence of SEQ ID NO: 40;

(f) an antibody sharing at least 90% identity to the antibody comprising a variable heavy region comprising a CDR1$_{VH}$ sequence of SEQ ID NO: 43, a CDR2$_{VH}$ sequence of SEQ ID NO: 44, and a CDR3$_{VH}$ sequence of SEQ ID NO: 45; and a variable light region comprising a CDR1$_{VL}$ sequence of SEQ ID NO: 46, a CDR2$_{VL}$ sequence of SEQ ID NO: 47, and a CDR3$_{VL}$ sequence of SEQ ID NO: 48;

(g) an antibody sharing at least 90% identity to the antibody comprising a variable heavy region comprising a CDR1$_{VH}$ sequence of SEQ ID NO: 51, a CDR2$_{VH}$ sequence of SEQ ID NO: 52, and a CDR3$_{VH}$ sequence of SEQ ID NO: 53; and a variable light region comprising a CDR1$_{VL}$ sequence of SEQ ID NO: 54, a CDR2$_{VL}$ sequence of SEQ ID NO: 55, and a CDR3$_{VL}$ sequence of SEQ ID NO: 56;

(h) an antibody sharing at least 90% identity to the antibody comprising a variable heavy region comprising a CDR1$_{VH}$ sequence of SEQ ID NO: 59, a CDR2$_{VH}$ sequence of SEQ ID NO: 60, and a CDR3$_{VH}$ sequence of SEQ ID NO: 61; and a variable light region comprising a CDR1$_{VL}$ sequence of SEQ ID NO: 62, a CDR2$_{VL}$ sequence of SEQ ID NO: 63, and a CDR3$_{VL}$ sequence of SEQ ID NO: 64;

(i) an antibody sharing at least 90% identity to the antibody comprising a variable heavy region comprising a CDR1$_{VH}$ sequence of SEQ ID NO: 67, a CDR2$_{VH}$ sequence of SEQ ID NO: 68, and a CDR3$_{VH}$ sequence of SEQ ID NO: 69; and a variable light region comprising a CDR1$_{VL}$ sequence of SEQ ID NO: 70, a CDR2$_{VL}$ sequence of SEQ ID NO: 71, and a CDR3$_{VL}$ sequence of SEQ ID NO: 72;

(j) an antibody sharing at least 90% identity to the antibody comprising a variable heavy region comprising a CDR1$_{VH}$ sequence of SEQ ID NO: 75, a CDR2$_{VH}$ sequence of SEQ ID NO: 76, and a CDR3$_{VH}$ sequence of SEQ ID NO: 77; and a variable light region comprising a CDR1$_{VL}$ sequence of SEQ ID NO: 78, a CDR2$_{VL}$ sequence of SEQ ID NO: 79, and a CDR3$_{VL}$ sequence of SEQ ID NO: 80;

(k) an antibody sharing at least 90% identity to the antibody comprising a variable heavy region comprising a CDR1$_{VH}$ sequence of SEQ ID NO: 83, a CDR2$_{VH}$ sequence of SEQ ID NO: 84, and a CDR3$_{VH}$ sequence of SEQ ID NO: 85; and a variable light region comprising a CDR1$_{VL}$ sequence of SEQ ID NO: 86, a CDR2$_{VL}$ sequence of SEQ ID NO: 87, and a CDR3$_{VL}$ sequence of SEQ ID NO: 88;

(l) an antibody sharing at least 90% identity to the antibody comprising a variable heavy region comprising a CDR1$_{VH}$ sequence of SEQ ID NO: 91, a CDR2$_{VH}$ sequence of SEQ ID NO: 92, and a CDR3$_{VH}$ sequence of SEQ ID NO: 93; and a variable light region comprising a CDR1$_{VL}$ sequence of SEQ ID NO: 94, a CDR2$_{VL}$ sequence of SEQ ID NO: 95, and a CDR3$_{VL}$ sequence of SEQ ID NO: 96;

(m) an antibody sharing at least 90% identity to the antibody comprising a variable heavy region comprising a CDR1$_{VH}$ sequence of SEQ ID NO: 99, a CDR2$_{VH}$ sequence of SEQ ID NO: 100, and a CDR3$_{VH}$ sequence of SEQ ID NO: 101; and a variable light region comprising a CDR1$_{VL}$ sequence of SEQ ID NO: 102, a CDR2$_{VL}$ sequence of SEQ ID NO: 103, and a CDR3$_{VL}$ sequence of SEQ ID NO: 104;

(n) an antibody sharing at least 90% identity to the antibody comprising a variable heavy region comprising a CDR1$_{VH}$ sequence of SEQ ID NO: 107, a CDR2$_{VH}$ sequence of SEQ ID NO: 108, and a CDR3$_{VH}$ sequence of SEQ ID NO: 109; and a variable light region comprising a CDR1$_{VL}$ sequence of SEQ ID NO: 110, a CDR2$_{VL}$ sequence of SEQ ID NO: 111, and a CDR3$_{VL}$ sequence of SEQ ID NO: 112;

(o) an antibody sharing at least 90% identity to the antibody comprising a variable heavy region comprising a CDR1$_{VH}$ sequence of SEQ ID NO: 115, a CDR2$_{VH}$ sequence of SEQ ID NO: 116, and a CDR3$_{VH}$ sequence of SEQ ID NO: 117; and a variable light region comprising a CDR1$_{VL}$ sequence of SEQ ID NO: 118, a CDR2$_{VL}$ sequence of SEQ ID NO: 119, and a CDR3$_{VL}$ sequence of SEQ ID NO: 120;

(p) an antibody sharing at least 90% identity to the antibody comprising a variable heavy region comprising a CDR1$_{VH}$ sequence of SEQ ID NO: 123, a CDR2$_{VH}$ sequence of SEQ ID NO: 124, and a CDR3$_{VH}$ sequence of SEQ ID NO: 125; and a variable light region comprising a CDR1$_{VL}$ sequence of SEQ ID NO: 126, a CDR2$_{VL}$ sequence of SEQ ID NO: 127, and a CDR3$_{VL}$ sequence of SEQ ID NO: 128;

(q) an antibody sharing at least 90% identity to the antibody comprising a variable heavy region comprising a CDR1$_{VH}$ sequence of SEQ ID NO: 131, a CDR2$_{VH}$ sequence of SEQ ID NO: 132, and a CDR3$_{VH}$ sequence of SEQ ID NO: 133; and a variable light region comprising a CDR1$_{VL}$ sequence of SEQ ID NO: 134, a CDR2$_{VL}$ sequence of SEQ ID NO: 135, and a CDR3$_{VL}$ sequence of SEQ ID NO: 136;

(r) an antibody sharing at least 90% identity to the antibody comprising a variable heavy region comprising a CDR1$_{VH}$ sequence of SEQ ID NO: 139, a CDR2$_{VH}$ sequence of SEQ ID NO: 140, and a CDR3$_{VH}$ sequence of SEQ ID NO: 141; and a variable light region comprising a CDR1$_{VL}$ sequence of SEQ ID NO: 142, a CDR2$_{VL}$ sequence of SEQ ID NO: 143, and a CDR3$_{VL}$ sequence of SEQ ID NO: 144;

(s) an antibody sharing at least 90% identity to the antibody comprising a variable heavy region comprising a CDR1$_{VH}$ sequence of SEQ ID NO: 147, a CDR2$_{VH}$ sequence of SEQ ID NO: 148, and a CDR3$_{VH}$ sequence of SEQ ID NO: 149; and a variable light region comprising a CDR1$_{VL}$ sequence of SEQ ID NO: 150, a CDR2$_{VL}$ sequence of SEQ ID NO: 151, and a CDR3$_{VL}$ sequence of SEQ ID NO: 152;

(t) an antibody sharing at least 90% identity to the antibody comprising a variable heavy region comprising a CDR1$_{VH}$ sequence of SEQ ID NO: 155, a CDR2$_{VH}$ sequence of SEQ ID NO: 156, and a CDR3$_{VH}$ sequence of SEQ ID NO: 157; and a variable light region comprising a CDR1$_{VL}$ sequence of SEQ ID NO: 158, a CDR2$_{VL}$ sequence of SEQ ID NO: 159, and a CDR3$_{VL}$ sequence of SEQ ID NO: 160;

(u) an antibody sharing at least 90% identity to the antibody comprising a variable heavy region comprising a CDR1$_{VH}$ sequence of SEQ ID NO: 163, a CDR2$_{VH}$ sequence of SEQ ID NO: 164, and a CDR3$_{VH}$ sequence of SEQ ID NO: 165; and a variable light region comprising a CDR1$_{VL}$ sequence of SEQ ID NO: 166, a CDR2$_{VL}$ sequence of SEQ ID NO: 167, and a CDR3$_{VL}$ sequence of SEQ ID NO: 168;

(v) an antibody sharing at least 90% identity to the antibody comprising a variable heavy region comprising a CDR1$_{VH}$ sequence of SEQ ID NO: 171, a CDR2$_{VH}$ sequence of SEQ ID NO: 172, and a CDR3$_{VH}$ sequence of SEQ ID NO: 173; and a variable light region comprising a CDR1$_{VL}$ sequence of SEQ ID NO: 174, a CDR2$_{VL}$ sequence of SEQ ID NO: 175, and a CDR3$_{VL}$ sequence of SEQ ID NO: 176.

2. The method of claim 1, wherein CMV infection of epithelial cells but not CMV infection of fibroblasts is neutralized in the subject.

3. The method of claim 1, wherein CMV infection of epithelial cells, endothelial cells, primary placental cytotrophoblast cells or a combination thereof is neutralized in the subject.

4. The method of claim 1, wherein CMV infection of fibroblasts, epithelial cells, endothelial cells, cytotrophoblasts or a combination thereof is prevented in the subject.

\* \* \* \* \*

UNITED STATES PATENT AND TRADEMARK OFFICE
CERTIFICATE OF CORRECTION

PATENT NO. : 11,384,137 B2
APPLICATION NO. : 16/680205
DATED : July 12, 2022
INVENTOR(S) : Don J. Diamond et al.

Page 1 of 1

It is certified that error appears in the above-identified patent and that said Letters Patent is hereby corrected as shown below:

In the Specification

Statement of Government Interest section, Column 1, Lines 20-23, please delete:
"This invention was made with government support under Grant Number R01 AI103960, awarded by the National Institutes of Health. The government has certain rights in the invention."

And insert:
--This invention was made with government support under R01 AI103960 awarded by the National Institutes of Health. The government has certain rights in the invention.--

Signed and Sealed this
Sixteenth Day of September, 2025

Coke Morgan Stewart
*Acting Director of the United States Patent and Trademark Office*

SEQUENCE LISTING

<160> NUMBER OF SEQ ID NOS: 215

<210> SEQ ID NO 1
<211> LENGTH: 355
<212> TYPE: DNA
<213> ORGANISM: Artificial Sequence
<220> FEATURE:
<223> OTHER INFORMATION: 1B2-VH vaccine-derived NAb

<400> SEQUENCE: 1

```
gaagtgcagc tggtggagtc tgggggaggc ttagtgaagc ctggagggtc cctgaaactc      60
tcctgtgcag cctctggatt cactttcagt gactattaca tgtattgggt tcgccagact     120
ccggaaaaga ggctggagtg ggtcgcaacc attagtgatg atggtaatta caccaactat     180
ccagacagtg tgaaggggcg attcaccatc tccagagaca atgccaagaa caatctttac     240
ctgcaaatga gcagtctgaa gtctgaggac acagccatgt attactgtgc aagaggatgg     300
ttactaccag tatttgctta ctggggccaa gggactctgg tcactgtctc tgctg          355
```

<210> SEQ ID NO 2
<211> LENGTH: 322
<212> TYPE: DNA
<213> ORGANISM: Artificial Sequence
<220> FEATURE:
<223> OTHER INFORMATION: 1B2-VL vaccine-derived NAb

<400> SEQUENCE: 2

```
gatattgtgc taactcagtc tccagccacc ctgtctgtga ctccaggaga tagcgtcagt      60
ctttcctgca gggccagcca gagtattggc aacaacctac actggtatca acaaaaatca     120
catgagtctc caaggcttct catcaaatat acttcccagt ccatctctgg aatcccctcc     180
aggttcagtg gcagtggatc agggacagat ttcactctca atatcaacag tgtggagact     240
```

```
gaagattttg gagtgtattt ctgtcagcag agtaacagat ggccgtggac gttcggtgga    300
ggcaccaagc tggaaatcaa ac                                             322
```

<210> SEQ ID NO 3
<211> LENGTH: 23
<212> TYPE: DNA
<213> ORGANISM: Artificial Sequence
<220> FEATURE:
<223> OTHER INFORMATION: 1B2-VH-CDR1 vaccine-derived NAb

<400> SEQUENCE: 3

```
ggattcactt tcagtgacta tta                                             23
```

<210> SEQ ID NO 4
<211> LENGTH: 24
<212> TYPE: DNA
<213> ORGANISM: Artificial Sequence
<220> FEATURE:
<223> OTHER INFORMATION: 1B2-VH-CDR2 vaccine-derived NAb

<400> SEQUENCE: 4

```
attagtgatg atggtaatta cacc                                            24
```

<210> SEQ ID NO 5
<211> LENGTH: 34
<212> TYPE: DNA
<213> ORGANISM: Artificial Sequence
<220> FEATURE:
<223> OTHER INFORMATION: 1B2-VH-CDR3 vaccine-derived NAb

<400> SEQUENCE: 5

```
gcaagaggat ggttactacc agtatttgct tact                                 34
```

<210> SEQ ID NO 6
<211> LENGTH: 18
<212> TYPE: DNA
<213> ORGANISM: Artificial Sequence
<220> FEATURE:
<223> OTHER INFORMATION: 1B2-VL-CDR1 vaccine-derived NAb

<400> SEQUENCE: 6

```
cagagtattg gcaacaac                                                   18
```

<210> SEQ ID NO 7
<211> LENGTH: 9
<212> TYPE: DNA
<213> ORGANISM: Artificial Sequence
<220> FEATURE:
<223> OTHER INFORMATION: 1B2-VL-CDR2 vaccine-derived NAb

<400> SEQUENCE: 7

```
tatacttcc                                                              9
```

<210> SEQ ID NO 8
<211> LENGTH: 27
<212> TYPE: DNA
<213> ORGANISM: Artificial Sequence
<220> FEATURE:
<223> OTHER INFORMATION: 1B2-VL-CDR3 vaccine-derived NAb

<400> SEQUENCE: 8

```
cagcagagta acagatggcc gtggacg                                         27
```

<210> SEQ ID NO 9

```
<211> LENGTH: 364
<212> TYPE: DNA
<213> ORGANISM: Artificial Sequence
<220> FEATURE:
<223> OTHER INFORMATION: 54E11-VH vaccine-derived NAb

<400> SEQUENCE: 9
cagatccagt tggtgcagtc tggacctgag ctgaagaagc tggagagac agtcaagatc      60
tcctgcaagg cttctggata taccttcaca agctatggaa tgaactgggt gaagcaggct    120
ccaggaaagg gtttaaagtg gatgggctgg ataaacacct acactggaga gccaacatat    180
gctgatgact tcaagggacg gtttgccttc tctttggaaa cctctgccag cactgcctat    240
ttacagatca acaacctcaa aaatgaggac acggctacat atttctgtgc aagagaacat    300
tactacggta ttaaccccct ttaggctgc tggggccaag gcaccactct cacagtctcc     360
tcag                                                                 364

<210> SEQ ID NO 10
<211> LENGTH: 322
<212> TYPE: DNA
<213> ORGANISM: Artificial Sequence
<220> FEATURE:
<223> OTHER INFORMATION: 54E11-VL vaccine-derived NAb

<400> SEQUENCE: 10
gatatccaga tgacacagac tacatcctcc ctgtctgcct ctctgggaga cagagtcacc      60
atcagttgca gtgcaagtca gggcattagc aattatttaa actggtatca gcagaaacca    120
gatggaactg ttaaactcct gatctatgac acatcaagtt acactcagg agtcccatca     180
aggttcagtg gcagtgggtc tgggacagat tattctctca caatcagcaa cctggaacct    240
gaagatattg ccacttacta ttgtcagcag tatagtaagc ttccttacac gttcggaggg    300
gggaccaagc tggaaataaa ac                                             322

<210> SEQ ID NO 11
<211> LENGTH: 24
<212> TYPE: DNA
<213> ORGANISM: Artificial Sequence
<220> FEATURE:
<223> OTHER INFORMATION: 54E11-VH-CDR1 vaccine-derived NAb

<400> SEQUENCE: 11
ggatatacct tcacaagcta tgga                                            24

<210> SEQ ID NO 12
<211> LENGTH: 24
<212> TYPE: DNA
<213> ORGANISM: Artificial Sequence
<220> FEATURE:
<223> OTHER INFORMATION: 54E11-VH-CDR2 vaccine-derived NAb

<400> SEQUENCE: 12
ataaacacct acactggaga gcca                                            24

<210> SEQ ID NO 13
<211> LENGTH: 42
<212> TYPE: DNA
<213> ORGANISM: Artificial Sequence
<220> FEATURE:
<223> OTHER INFORMATION: 54E11-VH-CDR3 vaccine-derived NAb

<400> SEQUENCE: 13
gcaagagaac attactacgg tattaacccc cttttaggct gc                        42
```

<210> SEQ ID NO 14
<211> LENGTH: 18
<212> TYPE: DNA
<213> ORGANISM: Artificial Sequence
<220> FEATURE:
<223> OTHER INFORMATION: 54E11-VL-CDR1 vaccine-derived NAb

<400> SEQUENCE: 14
cagggcatta gcaattat                                                   18

<210> SEQ ID NO 15
<211> LENGTH: 9
<212> TYPE: DNA
<213> ORGANISM: Artificial Sequence
<220> FEATURE:
<223> OTHER INFORMATION: 54E11-VL-CDR2 vaccine-derived NAb

<400> SEQUENCE: 15 gacacatca                                                              9

<210> SEQ ID NO 16
<211> LENGTH: 27
<212> TYPE: DNA
<213> ORGANISM: Artificial Sequence
<220> FEATURE:
<223> OTHER INFORMATION: 54E11-VL-CDR3 vaccine-derived NAb

<400> SEQUENCE: 16
cagcagtata gtaagcttcc ttacacg                                         27

<210> SEQ ID NO 17
<211> LENGTH: 364
<212> TYPE: DNA
<213> ORGANISM: Artificial Sequence
<220> FEATURE:
<223> OTHER INFORMATION: 21F6-VH vaccine-derived NAb

<400> SEQUENCE: 17
cagatccagt tggtgcagtc tggacctgag ctgaagaagc ctggagagac agtcaagatc     60
tcctgcaagg cttctggata taccttcaca agctatggaa tgaactgggt gaagcaggct    120
ccaggaaagg gtttaaagtg gatgggctgg ataaacacct acactggaga gccaacatat    180
gctgatgact caagggacg gtttgccttc tctttggaaa cctctgccag cactgcctat     240
ttacagatca caacctcaa aaatgaggac acggctacat atttctgtgc aagagaacat    300
tactacggta ttaaccccct tttaggctgc tggggccaag gcaccactct cacagtctcc    360
tcag                                                                 364

<210> SEQ ID NO 18
<211> LENGTH: 322
<212> TYPE: DNA
<213> ORGANISM: Artificial Sequence
<220> FEATURE:
<223> OTHER INFORMATION: 21F6-VL vaccine-derived NAb

<400> SEQUENCE: 18
gatatccaga tgacacagac tacatcctcc ctgtctgcct ctctgggaga cagagtcacc     60
atcagttgca gtgcaagtca gggcattagc aattatttaa actggtatca gcagaaacca    120
gatggaactg ttaaactcct gatctatgac acatcaagtt tacactcagg agtcccatca    180
aggttcagtg gcagtgggtc tgggacagat tattctctca caatcagcaa cctggaacct    240

```
gaagatattg ccacttacta ttgtcagcag tatagtaagc ttccttacac gttcggaggg        300
gggaccaagc tggaaataaa ac                                                 322

<210> SEQ ID NO 19
<211> LENGTH: 24
<212> TYPE: DNA
<213> ORGANISM: Artificial Sequence
<220> FEATURE:
<223> OTHER INFORMATION: 21F6-VH-CDR1 vaccine-derived NAb

<400> SEQUENCE: 19
ggatatacct tcacaagcta tgga                                               24

<210> SEQ ID NO 20
<211> LENGTH: 24
<212> TYPE: DNA
<213> ORGANISM: Artificial Sequence
<220> FEATURE:
<223> OTHER INFORMATION: 21F6-VH-CDR2 vaccine-derived NAb

<400> SEQUENCE: 20
ataaacacct acactggaga gcca                                               24

<210> SEQ ID NO 21
<211> LENGTH: 42
<212> TYPE: DNA
<213> ORGANISM: Artificial Sequence
<220> FEATURE:
<223> OTHER INFORMATION: 21F6-VH-CDR3 vaccine-derived NAb

<400> SEQUENCE: 21
gcaagagaac attactacgg tattaaccccc cttttaggct gc                          42

<210> SEQ ID NO 22
<211> LENGTH: 18
<212> TYPE: DNA
<213> ORGANISM: Artificial Sequence
<220> FEATURE:
<223> OTHER INFORMATION: 21F6-VL-CDR1 vaccine-derived NAb

<400> SEQUENCE: 22
cagggcatta gcaattat                                                      18

<210> SEQ ID NO 23
<211> LENGTH: 9
<212> TYPE: DNA
<213> ORGANISM: Artificial Sequence
<220> FEATURE:
<223> OTHER INFORMATION: 21F6-VL-CDR2 vaccine-derived NAb

<400> SEQUENCE: 23 gacacatca                                                                9

<210> SEQ ID NO 24
<211> LENGTH: 27
<212> TYPE: DNA
<213> ORGANISM: Artificial Sequence
<220> FEATURE:
<223> OTHER INFORMATION: 21F6-VL-CDR3 vaccine-derived NAb

<400> SEQUENCE: 24
cagcagtata gtaagcttcc ttacacg                                            27

<210> SEQ ID NO 25
<211> LENGTH: 367
```

```
<212> TYPE: DNA
<213> ORGANISM: Artificial Sequence
<220> FEATURE:
<223> OTHER INFORMATION: 12E2-VH vaccine-derived NAb

<400> SEQUENCE: 25
gaagtgaagc tggtggagtc tggggggaggc ttagtgcagc ctggagggtc cctgaaactc     60
tcctgtgcaa cctctggatt cactttcagt gactattaca tgttttgggt tcgccagact    120
ccagagaaga agctggagtg ggtcgcatac attagtaatg gtggtggtag cacctattat    180
ccagacactg taaagggccg attcaccatc tccagagaca tgacaagaa caccctatac     240 ctgcaaatga gtcgtctgaa gtctgacgac acagccttgt attactgtgt aagaccgaaa    300
cgggactttc aatacctcta tgctatggac tactggggtc aaggaacctc agtcaccgtc    360
tcctcag                                                              367

<210> SEQ ID NO 26
<211> LENGTH: 334
<212> TYPE: DNA
<213> ORGANISM: Artificial Sequence
<220> FEATURE:
<223> OTHER INFORMATION: 12E2-VL vaccine-derived NAb

<400> SEQUENCE: 26
gacattgtgc tgacacagtc tcctgcttcc ttagctgtat ctctggggca gagggccacc     60
atctcatgca gggccagcaa aagtgtcagt acatctggct atagttatat gcactggtac    120
caacagaaac caggacagtc acccaaactc ctcatctatc ttgcatccaa cctagaatct    180
ggggtccctg ccaggttcag tggcagtggg tctgggacag acttcaccct caacatccat    240
cctgtggagg acgaggatgc tgcaacctat tactgtcagc acagtaggga gcttccgtgg    300
acgttcggtg gaggcaccaa gctggaaatc aaac                                334

<210> SEQ ID NO 27
<211> LENGTH: 24
<212> TYPE: DNA
<213> ORGANISM: Artificial Sequence
<220> FEATURE:
<223> OTHER INFORMATION: 12E2-VH-CDR1 vaccine-derived NAb

<400> SEQUENCE: 27
ggattcactt tcagtgacta ttac                                            24

<210> SEQ ID NO 28
<211> LENGTH: 24
<212> TYPE: DNA
<213> ORGANISM: Artificial Sequence
<220> FEATURE:
<223> OTHER INFORMATION: 12E2-VH-CDR2 vaccine-derived NAb

<400> SEQUENCE: 28
attagtaatg gtggtggtag cacc                                            24

<210> SEQ ID NO 29
<211> LENGTH: 45
<212> TYPE: DNA
<213> ORGANISM: Artificial Sequence
<220> FEATURE:
<223> OTHER INFORMATION: 12E2-VH-CDR3 vaccine-derived NAb

<400> SEQUENCE: 29
gtaagaccga acgggacttt caatacctc tatgctatgg actac                      45
```

<210> SEQ ID NO 30
<211> LENGTH: 30
<212> TYPE: DNA
<213> ORGANISM: Artificial Sequence
<220> FEATURE:
<223> OTHER INFORMATION: 12E2-VL-CDR1 vaccine-derived NAb

<400> SEQUENCE: 30
aaaagtgtca gtacatctgg ctatagttat                                      30

<210> SEQ ID NO 31
<211> LENGTH: 9
<212> TYPE: DNA
<213> ORGANISM: Artificial Sequence
<220> FEATURE:
<223> OTHER INFORMATION: 12E2-VL-CDR2 vaccine-derived NAb

<400> SEQUENCE: 31 cttgcatcc                                                              9

<210> SEQ ID NO 32
<211> LENGTH: 27
<212> TYPE: DNA
<213> ORGANISM: Artificial Sequence
<220> FEATURE:
<223> OTHER INFORMATION: 12E2-VL-CDR3 vaccine-derived NAb

<400> SEQUENCE: 32
cagcacagta gggagcttcc gtggacg                                         27

<210> SEQ ID NO 33
<211> LENGTH: 370
<212> TYPE: DNA
<213> ORGANISM: Artificial Sequence
<220> FEATURE:
<223> OTHER INFORMATION: 13B5-VH vaccine-derived NAb

<400> SEQUENCE: 33
caggttactc tgaaagagtc tggccctggg atattgaagc cctcacagac cctcagtctg     60
acttgttctt tctctgggtt ttcactgacc acttctggtt tgggtgtagg ctggattcgt    120
cagccttcag ggaagggtct ggagtggctg gcacacattt ggtgggatga tgataaatac    180
tttaacccat ccctgaggaa ccagctcaca atctccaagg atacctccag aaaccaggta    240
ttcctcgaga tcaccagtgt gaccactgca gatactgcca cttactactg tgttcgaagc    300
ctttatgatt acgacgaggg gtactacttt gactcctggg gccaaggcac cactctcaca    360
gtctcctcag                                                           370

<210> SEQ ID NO 34
<211> LENGTH: 322
<212> TYPE: DNA
<213> ORGANISM: Artificial Sequence
<220> FEATURE:
<223> OTHER INFORMATION: 13B5-VL vaccine-derived NAb

<400> SEQUENCE: 34
gacattgtga tgactcagtc tccagccacc ctgtctgtga atccaggaga tagagtctct     60
ctctcctgca gggccagcca gagtattagc gactacttac actggtatca acaaaaatca    120
catgagtctc caaggcttct catcaaatac gcttcccaat ccatctctgg gatcccctcc    180
aggttcagtg gcagtggatc agggtcagat ttcactctca gtatcaacag tgtggaacct    240
gaagatgttg gagtgtatta ttgtcaaaat ggtcacacct ttcctccgac gttcggtgga    300
ggcaccaagc tggaaatcaa ac                                              322

<210> SEQ ID NO 35
<211> LENGTH: 30
<212> TYPE: DNA
<213> ORGANISM: Artificial Sequence
<220> FEATURE:
<223> OTHER INFORMATION: 13B5-VH-CDR1 vaccine-derived NAb

<400> SEQUENCE: 35
gggttttcac tgaccacttc tggtttgggt                                       30

<210> SEQ ID NO 36
<211> LENGTH: 21
<212> TYPE: DNA
<213> ORGANISM: Artificial Sequence
<220> FEATURE:
<223> OTHER INFORMATION: 13B5-VH-CDR2 vaccine-derived NAb

<400> SEQUENCE: 36
atttggtggg atgatgataa a                                                21

<210> SEQ ID NO 37
<211> LENGTH: 45
<212> TYPE: DNA
<213> ORGANISM: Artificial Sequence
<220> FEATURE:
<223> OTHER INFORMATION: 13B5-VH-CDR3 vaccine-derived NAb

<400> SEQUENCE: 37
gttcgaagcc tttatgatta cgacgagggg tactactttg actcc                      45

<210> SEQ ID NO 38
<211> LENGTH: 18
<212> TYPE: DNA
<213> ORGANISM: Artificial Sequence
<220> FEATURE:
<223> OTHER INFORMATION: 13B5-VL-CDR1 vaccine-derived NAb

<400> SEQUENCE: 38
cagagtatta gcgactac                                                    18

<210> SEQ ID NO 39
<211> LENGTH: 9
<212> TYPE: DNA
<213> ORGANISM: Artificial Sequence
<220> FEATURE:
<223> OTHER INFORMATION: 13B5-VL-CDR2 vaccine-derived NAb

<400> SEQUENCE: 39 tacgcttcc                                                               9

<210> SEQ ID NO 40
<211> LENGTH: 27
<212> TYPE: DNA
<213> ORGANISM: Artificial Sequence
<220> FEATURE:
<223> OTHER INFORMATION: 13B5-VL-CDR3 vaccine-derived NAb

<400> SEQUENCE: 40
caaaatggtc acacctttcc tccgacg                                          27

<210> SEQ ID NO 41
<211> LENGTH: 349
<212> TYPE: DNA

```
<213> ORGANISM: Artificial Sequence
<220> FEATURE:
<223> OTHER INFORMATION: 18F10-VH vaccine-derived NAb

<400> SEQUENCE: 41
cagattactc agaaagagtc tggccctggg atattgcagc cctcccagac cctcagtctg    60
acttgttctt tctctgggtt ttcactgagc acttatggta taggaatagg ctggattcgt   120
cagccttcag ggaagggtct ggagtggctg gcacacattt ggtggaatga taataagaac   180
tataacacag ccctgaagag ccggctcaca atctccaagg atccctccaa caaccaggta   240
ttcctcaaga tcgccagtgt ggacactgca gatactgcca catacttctg tgctcgaact   300
gggtacttcg atgtctgggg cgcagggacc acggtcaccg tctcctcag              349

<210> SEQ ID NO 42
<211> LENGTH: 337
<212> TYPE: DNA
<213> ORGANISM: Artificial Sequence
<220> FEATURE:
<223> OTHER INFORMATION: 18F10-VL vaccine-derived NAb

<400> SEQUENCE: 42
gatgttgtga tgacccaaac tccactctcc ctgcctgtca gtcttggaga tcaagtctcc    60
atttcttgca gctctagtca gagccttgtg cacagtaatg aaacaccta tatacattgg   120 tacctgcaga aaccaggcca gtctccaaag ctcctgatct acacagtttc caaccgattt   180
tctggggtcc cagacaggtt cagtggcagt ggatcaggga cagatttcac actcaagatc   240
agcagagtgg aggctgagga tctgggactt tatttctgct ctcaaagtac acatgttccg   300
tacacgttcg gaggggggac caagctggaa ataaaac                            337

<210> SEQ ID NO 43
<211> LENGTH: 30
<212> TYPE: DNA
<213> ORGANISM: Artificial Sequence
<220> FEATURE:
<223> OTHER INFORMATION: 18F10-VH-CDR1 vaccine-derived NAb

<400> SEQUENCE: 43
gggttttcac tgagcactta tggtatagga                                     30

<210> SEQ ID NO 44
<211> LENGTH: 21
<212> TYPE: DNA
<213> ORGANISM: Artificial Sequence
<220> FEATURE:
<223> OTHER INFORMATION: 18F10-VH-CDR2 vaccine-derived NAb

<400> SEQUENCE: 44
atttggtgga atgataataa g                                              21

<210> SEQ ID NO 45
<211> LENGTH: 24
<212> TYPE: DNA
<213> ORGANISM: Artificial Sequence
<220> FEATURE:
<223> OTHER INFORMATION: 18F10-VH-CDR3 vaccine-derived NAb

<400> SEQUENCE: 45
gctcgaactg ggtacttcga tgtc                                           24

<210> SEQ ID NO 46
<211> LENGTH: 33
```

```
<212> TYPE: DNA
<213> ORGANISM: Artificial Sequence
<220> FEATURE:
<223> OTHER INFORMATION: 18F10-VL-CDR1 vaccine-derived NAb

<400> SEQUENCE: 46
cagagccttg tgcacagtaa tggaaacacc tat                            33

<210> SEQ ID NO 47
<211> LENGTH: 9
<212> TYPE: DNA
<213> ORGANISM: Artificial Sequence
<220> FEATURE:
<223> OTHER INFORMATION: 18F10-VL-CDR2 vaccine-derived NAb

<400> SEQUENCE: 47 acagtttcc                                                        9

<210> SEQ ID NO 48
<211> LENGTH: 27
<212> TYPE: DNA
<213> ORGANISM: Artificial Sequence
<220> FEATURE:
<223> OTHER INFORMATION: 18F10-VL-CDR3 vaccine-derived NAb

<400> SEQUENCE: 48
tctcaaagta cacatgttcc gtacacg                                   27

<210> SEQ ID NO 49
<211> LENGTH: 364
<212> TYPE: DNA
<213> ORGANISM: Artificial Sequence
<220> FEATURE:
<223> OTHER INFORMATION: 21E9-VH vaccine-derived NAb

<400> SEQUENCE: 49
cagatccagt tggtgcagtc tggacctgag ctgaagaagc ctggagagac agtcaagatc    60
tcctgcaagg cttctgggta taccttcaca atctatggaa tgaactgggt gaagcaggct   120
ccaggaaagg gtttaaagtg gatgggctgg ataaacacct acactggaga gccaacatat   180
gctgatgact caggggacg gtttgccttc tctttggaaa cctctgccag cactgcctat    240
ttgcagatca caacctcaa aaatgaggac acggctacat atttctgtgc aagaaagggg    300
tactacggta gtagcgggta ctttgactac tggggccaag gcaccactct cacagtctcc   360
tcag                                                               364

<210> SEQ ID NO 50
<211> LENGTH: 322
<212> TYPE: DNA
<213> ORGANISM: Artificial Sequence
<220> FEATURE:
<223> OTHER INFORMATION: 21E9-VL vaccine-derived NAb

<400> SEQUENCE: 50
agtattgtga tgacccagac tcccaaattc ctgcttgtat cagcaggaga cagggttacc    60
ataacctgca aggccagtca gagtgtgagt aatgatgtat cttggtacca acagaagcca   120
gggcagtctc ctaaactgct gatatactat gcgtccaatc gctacactgg agtccctgat   180
cgcttcactg gcagtggata tgggacggat ttcactttca ccatcagcac tgtgcaggct   240
gaagacctgg cagtttattt ctgtcagcag gattatagct ctccgtggac gttcggtgga   300
ggcaccaagc tggaaatcaa ac                                           322
```

```
<210> SEQ ID NO 51
<211> LENGTH: 24
<212> TYPE: DNA
<213> ORGANISM: Artificial Sequence
<220> FEATURE:
<223> OTHER INFORMATION: 21E9-VH-CDR1 vaccine-derived NAb

<400> SEQUENCE: 51
gggtatacct tcacaatcta tgga                                          24

<210> SEQ ID NO 52
<211> LENGTH: 24
<212> TYPE: DNA
<213> ORGANISM: Artificial Sequence
<220> FEATURE:
<223> OTHER INFORMATION: 21E9-VH-CDR2 vaccine-derived NAb

<400> SEQUENCE: 52
ataaacacct acactggaga gcca                                          24

<210> SEQ ID NO 53
<211> LENGTH: 42
<212> TYPE: DNA
<213> ORGANISM: Artificial Sequence
<220> FEATURE:
<223> OTHER INFORMATION: 21E9-VH-CDR3 vaccine-derived NAb

<400> SEQUENCE: 53
gcaagaaagg ggtactacgg tagtagcggg tactttgact ac                      42

<210> SEQ ID NO 54
<211> LENGTH: 18
<212> TYPE: DNA
<213> ORGANISM: Artificial Sequence
<220> FEATURE:
<223> OTHER INFORMATION: 21E9-VL-CDR1 vaccine-derived NAb

<400> SEQUENCE: 54
cagagtgtga gtaatgat                                                 18

<210> SEQ ID NO 55
<211> LENGTH: 9
<212> TYPE: DNA
<213> ORGANISM: Artificial Sequence
<220> FEATURE:
<223> OTHER INFORMATION: 21E9-VL-CDR2 vaccine-derived NAb

<400> SEQUENCE: 55 tatgcgtcc                                                            9

<210> SEQ ID NO 56
<211> LENGTH: 27
<212> TYPE: DNA
<213> ORGANISM: Artificial Sequence
<220> FEATURE:
<223> OTHER INFORMATION: 21E9-VL-CDR3 vaccine-derived NAb

<400> SEQUENCE: 56
cagcaggatt atagctctcc gtggacg                                       27

<210> SEQ ID NO 57
<211> LENGTH: 346
<212> TYPE: DNA
<213> ORGANISM: Artificial Sequence
<220> FEATURE:
<223> OTHER INFORMATION: 4A3-VH vaccine-derived NAb
```

<400> SEQUENCE: 57

```
caggtccaac tgcagcagcc tggggctgag ctggtgaggc ctggggcttc agtgaaactg      60
tcctgcaagg cttctggcta caccttcacc atctactgga tgaactgggt gaagcagagg     120
cctggacaag gccttgaatg gattggtatg attgatcctt cagacagtga aactcactac     180
aatcagatgt tcaaggacaa ggccacattg actgtagaca atcctccag cactgcctac      240
atgcagctca gcagcctgac atctgaggac tctgcggtct attactgtgc aagttctggg     300
acgggggctt actggggcca aggactctg ctcactgtct ctgcag                     346
```

<210> SEQ ID NO 58
<211> LENGTH: 337
<212> TYPE: DNA
<213> ORGANISM: Artificial Sequence
<220> FEATURE:
<223> OTHER INFORMATION: 4A3-VL vaccine-derived NAb

<400> SEQUENCE: 58

```
gatgttgtga tgacccagac tccactcact ttgtcggtta ccattgggaca accagcctcc     60
atctcttgca gtcaagtca gagcctctta gatagtgatg gaaagacata tttgaattgg     120
ttgttacaga ggccaggcca gtctccaaag cgcctgatct atttggtgtc taaactggac     180
tctggagtcc ctgacaggtt cactggcagt ggatcaggga cagatttcac actgaaaatc     240
agcagattgg aagctgagga tttgggagtt tattattgct ggcaaggtac acattttccg     300
tacacgttcg gaggggggac caagctggaa ataaaac                              337
```

<210> SEQ ID NO 59
<211> LENGTH: 24
<212> TYPE: DNA
<213> ORGANISM: Artificial Sequence
<220> FEATURE:
<223> OTHER INFORMATION: 4A3-VH-CDR1 vaccine-derived NAb

<400> SEQUENCE: 59

```
ggctacacct tcaccatcta ctgg                                             24
```

<210> SEQ ID NO 60
<211> LENGTH: 24
<212> TYPE: DNA
<213> ORGANISM: Artificial Sequence
<220> FEATURE:
<223> OTHER INFORMATION: 4A3-VH-CDR2 vaccine-derived NAb

<400> SEQUENCE: 60

```
attgatcctt cagacagtga aact                                             24
```

<210> SEQ ID NO 61
<211> LENGTH: 24
<212> TYPE: DNA
<213> ORGANISM: Artificial Sequence
<220> FEATURE:
<223> OTHER INFORMATION: 4A3-VH-CDR3 vaccine-derived NAb

<400> SEQUENCE: 61

```
gcaagttctg ggacgggggc ttac                                             24
```

<210> SEQ ID NO 62
<211> LENGTH: 33
<212> TYPE: DNA
<213> ORGANISM: Artificial Sequence
<220> FEATURE:

<223> OTHER INFORMATION: 4A3-VL-CDR1 vaccine-derived NAb

<400> SEQUENCE: 62
cagagcctct tagatagtga tggaaagaca tat                                33

<210> SEQ ID NO 63
<211> LENGTH: 9
<212> TYPE: DNA
<213> ORGANISM: Artificial Sequence
<220> FEATURE:
<223> OTHER INFORMATION: 4A3-VL-CDR2 vaccine-derived NAb

<400> SEQUENCE: 63 ttggtgtct                                                            9

<210> SEQ ID NO 64
<211> LENGTH: 27
<212> TYPE: DNA
<213> ORGANISM: Artificial Sequence
<220> FEATURE:
<223> OTHER INFORMATION: 4A3-VL-CDR3 vaccine-derived NAb

<400> SEQUENCE: 64
tggcaaggta cacattttcc gtacacg                                       27

<210> SEQ ID NO 65
<211> LENGTH: 349
<212> TYPE: DNA
<213> ORGANISM: Artificial Sequence
<220> FEATURE:
<223> OTHER INFORMATION: 62-11-VH vaccine-derived NAb

<400> SEQUENCE: 65
caggtccaac tgcagcagcc tggggctgag ctggtgaggc ctggggcttc agtgaagctg    60
tcctgcaagg cttctggcta caccttcacc agctactgga tgaactgggt gaagcagagg   120
cctggacaag gccttgaatg gattggtatg attgatcctt cagacagtga aactcactac   180
aatcaaatgt tcaaggacaa ggccacattg actgtagaca atcctccag cacagcctac    240 atgcaactca gcagcctgac atctgaggac tctgcggtct attactgttc aaatggttac   300
tcctcctttg cttactgggg ccaagggact ctggtcactg tctctgtag               349

<210> SEQ ID NO 66
<211> LENGTH: 322
<212> TYPE: DNA
<213> ORGANISM: Artificial Sequence
<220> FEATURE:
<223> OTHER INFORMATION: 62-11-VL vaccine-derived NAb

<400> SEQUENCE: 66
gatgtccaga tgacacagac tacatcctcc ctgtctgcct ctctgggaga cagagtcacc    60
atcagttgca gtgcaagtca gggcattagc aattatttaa actggtatca gcagaaacca   120
gatggaactg ttaaactcct gatctatgac acatcaagtt tacactcagg agtcccatca   180
aggttcagtg gcagtgggtc tgggacagat tattctctca caatcagcaa cctggaacct   240
gaagatattg ccacttacta ttgtcagcag tatagtaagc ttccctacac gttcggaggg   300
gggaccaagc tggaaataaa ac                                            322

<210> SEQ ID NO 67
<211> LENGTH: 24
<212> TYPE: DNA
<213> ORGANISM: Artificial Sequence

```
<220> FEATURE:
<223> OTHER INFORMATION: 62-11-VH-CDR1 vaccine-derived NAb

<400> SEQUENCE: 67
ggctacacct tcaccagcta ctgg                                              24

<210> SEQ ID NO 68
<211> LENGTH: 24
<212> TYPE: DNA
<213> ORGANISM: Artificial Sequence
<220> FEATURE:
<223> OTHER INFORMATION: 62-11-VH-CDR2 vaccine-derived NAb

<400> SEQUENCE: 68
attgatcctt cagacagtga aact                                              24

<210> SEQ ID NO 69
<211> LENGTH: 27
<212> TYPE: DNA
<213> ORGANISM: Artificial Sequence
<220> FEATURE:
<223> OTHER INFORMATION: 62-11-VH-CDR3 vaccine-derived NAb

<400> SEQUENCE: 69
tcaaatggtt actcctcctt tgcttac                                           27

<210> SEQ ID NO 70
<211> LENGTH: 18
<212> TYPE: DNA
<213> ORGANISM: Artificial Sequence
<220> FEATURE:
<223> OTHER INFORMATION: 62-11-VL-CDR1 vaccine-derived NAb

<400> SEQUENCE: 70
cagggcatta gcaattat                                                     18

<210> SEQ ID NO 71
<211> LENGTH: 9
<212> TYPE: DNA
<213> ORGANISM: Artificial Sequence
<220> FEATURE:
<223> OTHER INFORMATION: 62-11-VL-CDR2 vaccine-derived NAb

<400> SEQUENCE: 71 gacacatca                                                                9

<210> SEQ ID NO 72
<211> LENGTH: 27
<212> TYPE: DNA
<213> ORGANISM: Artificial Sequence
<220> FEATURE:
<223> OTHER INFORMATION: 62-11-VL-CDR3 vaccine-derived NAb

<400> SEQUENCE: 72
cagcagtata gtaagcttcc ctacacg                                           27

<210> SEQ ID NO 73
<211> LENGTH: 349
<212> TYPE: DNA
<213> ORGANISM: Artificial Sequence
<220> FEATURE:
<223> OTHER INFORMATION: 62-100-VH vaccine-derived NAb

<400> SEQUENCE: 73
caggtccaac tgcagcagcc tggggctgag ctggtgaggc ctggggcttc agtgaagctg       60
```

```
tcctgcaagg cttctggcta caccttcacc agctactgga tgaactgggt gaagcagagg    120
cctggacaag gccttgaatg gattggtatg attgatcctt cagacagtga aactcactac    180
aatcaaatgt tcaaggacaa ggccacattg actgtagaca atcctccag  cacagcctac    240 atgcaactca gcagcctgac atctgaggac tctgcggtct attactgttc aaatggttac    300
tcctcctttg cttactgggg ccaagggact ctggtcactg tctctgtag               349
```

<210> SEQ ID NO 74
<211> LENGTH: 322
<212> TYPE: DNA
<213> ORGANISM: Artificial Sequence
<220> FEATURE:
<223> OTHER INFORMATION: 62-100-VL vaccine-derived NAb

<400> SEQUENCE: 74

```
gatattgtgc taactcagtc tccagccacc ctgtctgtga ctccaggaga tagcgtcagt     60
ctttcctgca gggccagcca agtattagc  aacaacctac actggtatca acaaaaatca    120
catgagtctc caaggcttct catcaagtat gcttcccagt ccatctctgg atcccctcc     180 aggttcagtg gcagtggatc agggacagat ttcactctca gtatcaacag tgtggagact    240
gaagattttg gaagtatgt  ctgtcaacag agtaacagct ggccactcac gttcggctcg    300
gggacaaagt tggaaataaa ac                                             322
```

<210> SEQ ID NO 75
<211> LENGTH: 24
<212> TYPE: DNA
<213> ORGANISM: Artificial Sequence
<220> FEATURE:
<223> OTHER INFORMATION: 62-100-VH-CDR1 vaccine-derived NAb

<400> SEQUENCE: 75

```
ggctacacct tcaccagcta ctgg                                            24
```

<210> SEQ ID NO 76
<211> LENGTH: 24
<212> TYPE: DNA
<213> ORGANISM: Artificial Sequence
<220> FEATURE:
<223> OTHER INFORMATION: 62-100-VH-CDR2 vaccine-derived NAb

<400> SEQUENCE: 76

```
attgatcctt cagacagtga aact                                            24
```

<210> SEQ ID NO 77
<211> LENGTH: 27
<212> TYPE: DNA
<213> ORGANISM: Artificial Sequence
<220> FEATURE:
<223> OTHER INFORMATION: 62-100-VH-CDR3 vaccine-derived NAb

<400> SEQUENCE: 77

```
tcaaatggtt actcctcctt tgcttac                                         27
```

<210> SEQ ID NO 78
<211> LENGTH: 18
<212> TYPE: DNA
<213> ORGANISM: Artificial Sequence
<220> FEATURE:
<223> OTHER INFORMATION: 62-100-VL-CDR1 vaccine-derived NAb

<400> SEQUENCE: 78

```
caaagtatta gcaacaac                                                   18
```

<210> SEQ ID NO 79
<211> LENGTH: 9
<212> TYPE: DNA
<213> ORGANISM: Artificial Sequence
<220> FEATURE:
<223> OTHER INFORMATION: 62-100-VL-CDR2 vaccine-derived NAb

<400> SEQUENCE: 79 tatgcttcc                                                                                       9

<210> SEQ ID NO 80
<211> LENGTH: 27
<212> TYPE: DNA
<213> ORGANISM: Artificial Sequence
<220> FEATURE:
<223> OTHER INFORMATION: 62-100-VL-CDR3 vaccine-derived NAb

<400> SEQUENCE: 80
caacagagta acagctggcc actcacg                                                                  27

<210> SEQ ID NO 81
<211> LENGTH: 358
<212> TYPE: DNA
<213> ORGANISM: Artificial Sequence
<220> FEATURE:
<223> OTHER INFORMATION: 2-80-VH vaccine-derived NAb

<400> SEQUENCE: 81
cagatccagt tggtgcagtc tggacctgag ctgaagaagc ctggagagac agtcaagatc          60
tcctgcaagg cttctggata taccttcaca aactttggaa tgaactgggt gaagcaggct         120
ccaggaaagg gtttaaagtg gatgggctgg ataaacacct acactggaga gccaacatat         180
gctgatgact caagggacg gtttgccttc tctttggaaa cctctgccag cactgcctct          240
ttgcagatca acaacctcaa aaatgaggac acggctacat atttctgtgc aagaaggggg         300
gatggcctct attctatgga ctactggggt caaggaacct cagtcaccgt ctcctcag           358

<210> SEQ ID NO 82
<211> LENGTH: 334
<212> TYPE: DNA
<213> ORGANISM: Artificial Sequence
<220> FEATURE:
<223> OTHER INFORMATION: 2-80-VL vaccine-derived NAb

<400> SEQUENCE: 82
gacattgtgc tgacccaatc tccagcttct ttggctgtgt ctctggggca gagggccacc          60
atatcctgca gagccagtga agtattgat agttatggca atagtttat gtactggtac          120 cagcagaaac aggacagcc acccaaactc ctcatctatc gtgcatccaa cctagaatct         180
gggatccctg ccaggttcag tggcagtggg tctaggacag acttcaccct caccattaat         240
cctgtggagg ctgatgatgt tgcaacctat tactgtcagc aaagtaatga ggatcctctc         300
acgttcggtg ctgggaccaa gctggagctg aaac                                     334

<210> SEQ ID NO 83
<211> LENGTH: 24
<212> TYPE: DNA
<213> ORGANISM: Artificial Sequence
<220> FEATURE:
<223> OTHER INFORMATION: 2-80-VH-CDR1 vaccine-derived NAb

<400> SEQUENCE: 83 ggatataccct tcacaaactt tgga                                              24

<210> SEQ ID NO 84
<211> LENGTH: 24
<212> TYPE: DNA
<213> ORGANISM: Artificial Sequence
<220> FEATURE:
<223> OTHER INFORMATION: 2-80-VH-CDR2 vaccine-derived NAb

<400> SEQUENCE: 84 ataaacaccct acactggaga gcca                                              24

<210> SEQ ID NO 85
<211> LENGTH: 36
<212> TYPE: DNA
<213> ORGANISM: Artificial Sequence
<220> FEATURE:
<223> OTHER INFORMATION: 2-80-VH-CDR3 vaccine-derived NAb

<400> SEQUENCE: 85
gcaagaaggg gggatggcct ctattctatg gactac                                  36

<210> SEQ ID NO 86
<211> LENGTH: 30
<212> TYPE: DNA
<213> ORGANISM: Artificial Sequence
<220> FEATURE:
<223> OTHER INFORMATION: 2-80-VL-CDR1 vaccine-derived NAb

<400> SEQUENCE: 86
gaaagtattg atagttatgg caatagtttt                                         30

<210> SEQ ID NO 87
<211> LENGTH: 9
<212> TYPE: DNA
<213> ORGANISM: Artificial Sequence
<220> FEATURE:
<223> OTHER INFORMATION: 2-80-VL-CDR2 vaccine-derived NAb

<400> SEQUENCE: 87 cgtgcatcc                                                                 9

<210> SEQ ID NO 88
<211> LENGTH: 27
<212> TYPE: DNA
<213> ORGANISM: Artificial Sequence
<220> FEATURE:
<223> OTHER INFORMATION: 2-80-VL-CDR3 vaccine-derived NAb

<400> SEQUENCE: 88
cagcaaagta atgaggatcc tctcacg                                            27

<210> SEQ ID NO 89
<211> LENGTH: 118
<212> TYPE: PRT
<213> ORGANISM: Artificial Sequence
<220> FEATURE:
<223> OTHER INFORMATION: 1B2-VH vaccine-derived NAb

<400> SEQUENCE: 89

Glu Val Gln Leu Val Glu Ser Gly Gly Val Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val

```
                35                  40                  45
Ala Thr Ile Ser Asp Asp Gly Asn Tyr Thr Asn Tyr Pro Asp Ser Val
        50                  55                  60
Lys Gly Arg Phe Thr Ile Ser Arg Asp Asn Ala Lys Asn Asn Leu Tyr
65                  70                  75                  80
Leu Gln Met Ser Ser Leu Lys Ser Glu Asp Thr Ala Met Tyr Tyr Cys
                85                  90                  95
Ala Arg Gly Trp Leu Leu Pro Val Phe Ala Tyr Trp Gly Gln Gly Thr
            100                 105                 110
Leu Val Thr Val Ser Ala
        115

<210> SEQ ID NO 90
<211> LENGTH: 107
<212> TYPE: PRT
<213> ORGANISM: Artificial Sequence
<220> FEATURE:
<223> OTHER INFORMATION: 1B2-VL vaccine-derived NAb

<400> SEQUENCE: 90

Asp Ile Val Leu Thr Gln Ser Pro Ala Thr Leu Ser Val Thr Pro Gly
1               5                   10                  15
Asp Ser Val Ser Leu Ser Cys Arg Ala Ser Gln Ser Ile Gly Asn Asn
            20                  25                  30
Leu His Trp Tyr Gln Gln Lys Ser His Glu Ser Pro Arg Leu Leu Ile
        35                  40                  45
Lys Tyr Thr Ser Gln Ser Ile Ser Gly Ile Pro Ser Arg Phe Ser Gly
    50                  55                  60
Ser Gly Ser Gly Thr Asp Phe Thr Leu Asn Ile Asn Ser Val Glu Thr
65                  70                  75                  80
Glu Asp Phe Gly Val Tyr Phe Cys Gln Gln Ser Asn Arg Trp Pro Trp
                85                  90                  95
Thr Phe Gly Gly Gly Thr Lys Leu Glu Ile Lys
            100                 105

<210> SEQ ID NO 91
<211> LENGTH: 8
<212> TYPE: PRT
<213> ORGANISM: Artificial Sequence
<220> FEATURE:
<223> OTHER INFORMATION: 1B2-VH-CDR1 vaccine-derived NAb

<400> SEQUENCE: 91

Gly Phe Thr Phe Ser Asp Tyr Tyr
1               5

<210> SEQ ID NO 92
<211> LENGTH: 8
<212> TYPE: PRT
<213> ORGANISM: Artificial Sequence
<220> FEATURE:
<223> OTHER INFORMATION: 1B2-VH-CDR2 vaccine-derived NAb

<400> SEQUENCE: 92

Ile Ser Asp Asp Gly Asn Tyr Thr
1               5

<210> SEQ ID NO 93
<211> LENGTH: 11
<212> TYPE: PRT
<213> ORGANISM: Artificial Sequence
```

```
<220> FEATURE:
<223> OTHER INFORMATION: 1B2-VH-CDR3 vaccine-derived NAb

<400> SEQUENCE: 93

Ala Arg Gly Trp Leu Leu Pro Val Phe Ala Tyr
1               5                   10

<210> SEQ ID NO 94
<211> LENGTH: 6
<212> TYPE: PRT
<213> ORGANISM: Artificial Sequence
<220> FEATURE:
<223> OTHER INFORMATION: 1B2-VL-CDR1 vaccine-derived NAb

<400> SEQUENCE: 94

Gln Ser Ile Gly Asn Asn
1               5

<210> SEQ ID NO 95
<211> LENGTH: 3
<212> TYPE: PRT
<213> ORGANISM: Artificial Sequence
<220> FEATURE:
<223> OTHER INFORMATION: 1B2-VL-CDR2 vaccine-derived NAb

<400> SEQUENCE: 95

Tyr Thr Ser
1

<210> SEQ ID NO 96
<211> LENGTH: 9
<212> TYPE: PRT
<213> ORGANISM: Artificial Sequence
<220> FEATURE:
<223> OTHER INFORMATION: 1B2-VL-CDR3 vaccine-derived NAb

<400> SEQUENCE: 96

Gln Gln Ser Asn Arg Trp Pro Trp Thr
1               5

<210> SEQ ID NO 97
<211> LENGTH: 121
<212> TYPE: PRT
<213> ORGANISM: Artificial Sequence
<220> FEATURE:
<223> OTHER INFORMATION: 54E11-VH vaccine-derived NAb

<400> SEQUENCE: 97

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ser Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu His Tyr Tyr Gly Ile Asn Pro Leu Leu Gly Cys Trp Gly
            100                 105                 110

Gln Gly Thr Thr Leu Thr Val Ser Ser
```

<210> SEQ ID NO 98
<211> LENGTH: 107
<212> TYPE: PRT
<213> ORGANISM: Artificial Sequence
<220> FEATURE:
<223> OTHER INFORMATION: 54E11-VL vaccine-derived NAb

<400> SEQUENCE: 98

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Asp Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys
            100                 105

<210> SEQ ID NO 99
<211> LENGTH: 8
<212> TYPE: PRT
<213> ORGANISM: Artificial Sequence
<220> FEATURE:
<223> OTHER INFORMATION: 54E11-VH-CDR1 vaccine-derived NAb

<400> SEQUENCE: 99

Gly Tyr Thr Phe Thr Ser Tyr Gly
1               5

<210> SEQ ID NO 100
<211> LENGTH: 8
<212> TYPE: PRT
<213> ORGANISM: Artificial Sequence
<220> FEATURE:
<223> OTHER INFORMATION: 54E11-VH-CDR2 vaccine-derived NAb

<400> SEQUENCE: 100

Ile Asn Thr Tyr Thr Gly Glu Pro
1               5

<210> SEQ ID NO 101
<211> LENGTH: 14
<212> TYPE: PRT
<213> ORGANISM: Artificial Sequence
<220> FEATURE:
<223> OTHER INFORMATION: 54E11-VH-CDR3 vaccine-derived NAb

<400> SEQUENCE: 101

Ala Arg Glu His Tyr Tyr Gly Ile Asn Pro Leu Leu Gly Cys
1               5                   10

<210> SEQ ID NO 102
<211> LENGTH: 6
<212> TYPE: PRT
<213> ORGANISM: Artificial Sequence
<220> FEATURE:
<223> OTHER INFORMATION: 54E11-VL-CDR1 vaccine-derived NAb

```
<400> SEQUENCE: 102

Gln Gly Ile Ser Asn Tyr
1               5

<210> SEQ ID NO 103
<211> LENGTH: 3
<212> TYPE: PRT
<213> ORGANISM: Artificial Sequence
<220> FEATURE:
<223> OTHER INFORMATION: 54E11-VL-CDR2 vaccine-derived NAb

<400> SEQUENCE: 103

Asp Thr Ser
1

<210> SEQ ID NO 104
<211> LENGTH: 9
<212> TYPE: PRT
<213> ORGANISM: Artificial Sequence
<220> FEATURE:
<223> OTHER INFORMATION: 54E11-VL-CDR3 vaccine-derived NAb

<400> SEQUENCE: 104

Gln Gln Tyr Ser Lys Leu Pro Tyr Thr
1               5

<210> SEQ ID NO 105
<211> LENGTH: 121
<212> TYPE: PRT
<213> ORGANISM: Artificial Sequence
<220> FEATURE:
<223> OTHER INFORMATION: 21F6-VH vaccine-derived NAb

<400> SEQUENCE: 105

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ser Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu His Tyr Tyr Gly Ile Asn Pro Leu Leu Gly Cys Trp Gly
            100                 105                 110

Gln Gly Thr Thr Leu Thr Val Ser Ser
        115                 120

<210> SEQ ID NO 106
<211> LENGTH: 107
<212> TYPE: PRT
<213> ORGANISM: Artificial Sequence
<220> FEATURE:
<223> OTHER INFORMATION: 21F6-VL vaccine-derived NAb

<400> SEQUENCE: 106

Asp Ile Gln Met Thr Gln Thr Thr Ser Ser Leu Ser Ala Ser Leu Gly
1               5                   10                  15
```

```
Asp Arg Val Thr Ile Ser Cys Ser Ala Ser Gln Gly Ile Ser Asn Tyr
             20                  25                  30

Leu Asn Trp Tyr Gln Gln Lys Pro Asp Gly Thr Val Lys Leu Leu Ile
         35                  40                  45

Tyr Asp Thr Ser Ser Leu His Ser Gly Val Pro Ser Arg Phe Ser Gly
     50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Tyr
                 85                  90                  95

Thr Phe Gly Gly Gly Thr Lys Leu Glu Ile Lys
            100                 105
```

<210> SEQ ID NO 107
<211> LENGTH: 8
<212> TYPE: PRT
<213> ORGANISM: Artificial Sequence
<220> FEATURE:
<223> OTHER INFORMATION: 21F6-VH-CDR1 vaccine-derived NAb

<400> SEQUENCE: 107

```
Gly Tyr Thr Phe Thr Ser Tyr Gly
 1               5
```

<210> SEQ ID NO 108
<211> LENGTH: 8
<212> TYPE: PRT
<213> ORGANISM: Artificial Sequence
<220> FEATURE:
<223> OTHER INFORMATION: 21F6-VH-CDR2 vaccine-derived NAb

<400> SEQUENCE: 108

```
Ile Asn Thr Tyr Thr Gly Glu Pro
 1               5
```

<210> SEQ ID NO 109
<211> LENGTH: 14
<212> TYPE: PRT
<213> ORGANISM: Artificial Sequence
<220> FEATURE:
<223> OTHER INFORMATION: 21F6-VH-CDR3 vaccine-derived NAb

<400> SEQUENCE: 109

```
Ala Arg Glu His Tyr Tyr Gly Ile Asn Pro Leu Leu Gly Cys
 1               5                   10
```

<210> SEQ ID NO 110
<211> LENGTH: 6
<212> TYPE: PRT
<213> ORGANISM: Artificial Sequence
<220> FEATURE:
<223> OTHER INFORMATION: 21F6-VL-CDR1 vaccine-derived NAb

<400> SEQUENCE: 110

```
Gln Gly Ile Ser Asn Tyr
 1               5
```

<210> SEQ ID NO 111
<211> LENGTH: 3
<212> TYPE: PRT
<213> ORGANISM: Artificial Sequence
<220> FEATURE:
<223> OTHER INFORMATION: 21F6-VL-CDR2 vaccine-derived NAb

<400> SEQUENCE: 111

Asp Thr Ser
1

<210> SEQ ID NO 112
<211> LENGTH: 9
<212> TYPE: PRT
<213> ORGANISM: Artificial Sequence
<220> FEATURE:
<223> OTHER INFORMATION: 21F6-VL-CDR3 vaccine-derived NAb

<400> SEQUENCE: 112

Gln Gln Tyr Ser Lys Leu Pro Tyr Thr
1               5

<210> SEQ ID NO 113
<211> LENGTH: 122
<212> TYPE: PRT
<213> ORGANISM: Artificial Sequence
<220> FEATURE:
<223> OTHER INFORMATION: 12E2-VH vaccine-derived NAb

<400> SEQUENCE: 113

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Phe Trp Val Arg Gln Thr Pro Glu Lys Lys Leu Glu Trp Val
            35                  40                  45

Ala Tyr Ile Ser Asn Gly Gly Ser Thr Tyr Tyr Pro Asp Thr Val
        50                  55                  60

Lys Gly Arg Phe Thr Ile Ser Arg Asp Asn Asp Lys Asn Thr Leu Tyr
65                  70                  75                  80

Leu Gln Met Ser Arg Leu Lys Ser Asp Asp Thr Ala Leu Tyr Tyr Cys
                85                  90                  95

Val Arg Pro Lys Arg Asp Phe Gln Tyr Leu Tyr Ala Met Asp Tyr Trp
            100                 105                 110

Gly Gln Gly Thr Ser Val Thr Val Ser Ser
        115                 120

<210> SEQ ID NO 114
<211> LENGTH: 111
<212> TYPE: PRT
<213> ORGANISM: Artificial Sequence
<220> FEATURE:
<223> OTHER INFORMATION: 12E2-VL vaccine-derived NAb

<400> SEQUENCE: 114

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Met His Trp Tyr Gln Gln Lys Pro Gly Gln Ser Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Asp Glu Asp Ala Ala Thr Tyr Tyr Cys Gln His Ser Arg
                85                  90                  95

```
Glu Leu Pro Trp Thr Phe Gly Gly Gly Thr Lys Leu Glu Ile Lys
            100                 105                 110

<210> SEQ ID NO 115
<211> LENGTH: 8
<212> TYPE: PRT
<213> ORGANISM: Artificial Sequence
<220> FEATURE:
<223> OTHER INFORMATION: 12E2-VH-CDR1 vaccine-derived NAb

<400> SEQUENCE: 115

Gly Phe Thr Phe Ser Asp Tyr Tyr
1               5

<210> SEQ ID NO 116
<211> LENGTH: 8
<212> TYPE: PRT
<213> ORGANISM: Artificial Sequence
<220> FEATURE:
<223> OTHER INFORMATION: 12E2-VH-CDR2 vaccine-derived NAb

<400> SEQUENCE: 116

Ile Ser Asn Gly Gly Gly Ser Thr
1               5

<210> SEQ ID NO 117
<211> LENGTH: 15
<212> TYPE: PRT
<213> ORGANISM: Artificial Sequence
<220> FEATURE:
<223> OTHER INFORMATION: 12E2-VH-CDR3 vaccine-derived NAb

<400> SEQUENCE: 117

Val Arg Pro Lys Arg Asp Phe Gln Tyr Leu Tyr Ala Met Asp Tyr
1               5                   10                  15

<210> SEQ ID NO 118
<211> LENGTH: 10
<212> TYPE: PRT
<213> ORGANISM: Artificial Sequence
<220> FEATURE:
<223> OTHER INFORMATION: 12E2-VL-CDR1 vaccine-derived NAb

<400> SEQUENCE: 118

Lys Ser Val Ser Thr Ser Gly Tyr Ser Tyr
1               5                   10

<210> SEQ ID NO 119
<211> LENGTH: 3
<212> TYPE: PRT
<213> ORGANISM: Artificial Sequence
<220> FEATURE:
<223> OTHER INFORMATION: 12E2-VL-CDR2 vaccine-derived NAb

<400> SEQUENCE: 119

Leu Ala Ser
1

<210> SEQ ID NO 120
<211> LENGTH: 9
<212> TYPE: PRT
<213> ORGANISM: Artificial Sequence
<220> FEATURE:
<223> OTHER INFORMATION: 12E2-VL-CDR3 vaccine-derived NAb

<400> SEQUENCE: 120

Gln His Ser Arg Glu Leu Pro Trp Thr
```

<210> SEQ ID NO 121
<211> LENGTH: 123
<212> TYPE: PRT
<213> ORGANISM: Artificial Sequence
<220> FEATURE:
<223> OTHER INFORMATION: 13B5-VH vaccine-derived NAb

<400> SEQUENCE: 121

```
Gln Val Thr Leu Lys Glu Ser Gly Pro Gly Ile Leu Lys Pro Ser Gln
1               5                   10                  15
Thr Leu Ser Leu Thr Cys Ser Phe Ser Gly Phe Ser Leu Thr Thr Ser
            20                  25                  30
Gly Leu Gly Val Gly Trp Ile Arg Gln Pro Ser Gly Lys Gly Leu Glu
        35                  40                  45
Trp Leu Ala His Ile Trp Trp Asp Asp Lys Tyr Phe Asn Pro Ser
    50                  55                  60
Leu Arg Asn Gln Leu Thr Ile Ser Lys Asp Thr Ser Arg Asn Gln Val
65                  70                  75                  80
Phe Leu Glu Ile Thr Ser Val Thr Thr Ala Asp Thr Ala Thr Tyr Tyr
                85                  90                  95
Cys Val Arg Ser Leu Tyr Asp Tyr Asp Glu Gly Tyr Tyr Phe Asp Ser
            100                 105                 110
Trp Gly Gln Gly Thr Thr Leu Thr Val Ser Ser
        115                 120
```

<210> SEQ ID NO 122
<211> LENGTH: 107
<212> TYPE: PRT
<213> ORGANISM: Artificial Sequence
<220> FEATURE:
<223> OTHER INFORMATION: 13B5-VL vaccine-derived NAb

<400> SEQUENCE: 122

```
Glu Ile Val Met Ile Gln Ser Pro Ala Thr Leu Ser Val Asn Pro Gly
1               5                   10                  15
Asp Arg Val Ser Leu Ser Cys Arg Ala Ser Gln Ser Ile Ser Asp Tyr
            20                  25                  30
Leu His Trp Tyr Gln Gln Lys Ser His Glu Ser Pro Arg Leu Leu Ile
        35                  40                  45
Lys Tyr Ala Ser Gln Ser Ile Ser Gly Ile Pro Ser Arg Phe Ser Gly
    50                  55                  60
Ser Gly Ser Gly Ser Asp Phe Thr Leu Ser Ile Asn Ser Val Glu Pro
65                  70                  75                  80
Glu Asp Val Gly Val Tyr Tyr Cys Gln Asn Gly His Thr Phe Pro Pro
                85                  90                  95
Thr Phe Gly Gly Gly Thr Lys Leu Glu Ile Lys
            100                 105
```

<210> SEQ ID NO 123
<211> LENGTH: 10
<212> TYPE: PRT
<213> ORGANISM: Artificial Sequence
<220> FEATURE:
<223> OTHER INFORMATION: 13B5-VH-CDR1 vaccine-derived NAb

<400> SEQUENCE: 123

```
Gly Phe Ser Leu Thr Thr Ser Gly Leu Gly
1               5                   10
```

```
<210> SEQ ID NO 124
<211> LENGTH: 7
<212> TYPE: PRT
<213> ORGANISM: Artificial Sequence
<220> FEATURE:
<223> OTHER INFORMATION: 13B5-VH-CDR2 vaccine-derived NAb

<400> SEQUENCE: 124

Ile Trp Trp Asp Asp Asp Lys
1               5

<210> SEQ ID NO 125
<211> LENGTH: 15
<212> TYPE: PRT
<213> ORGANISM: Artificial Sequence
<220> FEATURE:
<223> OTHER INFORMATION: 13B5-VH-CDR3 vaccine-derived NAb

<400> SEQUENCE: 125

Val Arg Ser Leu Tyr Asp Tyr Asp Glu Gly Tyr Tyr Phe Asp Ser
1               5                   10                  15

<210> SEQ ID NO 126
<211> LENGTH: 6
<212> TYPE: PRT
<213> ORGANISM: Artificial Sequence
<220> FEATURE:
<223> OTHER INFORMATION: 13B5-VL-CDR1 vaccine-derived NAb

<400> SEQUENCE: 126

Gln Ser Ile Ser Asp Tyr
1               5

<210> SEQ ID NO 127
<211> LENGTH: 3
<212> TYPE: PRT
<213> ORGANISM: Artificial Sequence
<220> FEATURE:
<223> OTHER INFORMATION: 13B5-VL-CDR2 vaccine-derived NAb

<400> SEQUENCE: 127

Tyr Ala Ser
1

<210> SEQ ID NO 128
<211> LENGTH: 9
<212> TYPE: PRT
<213> ORGANISM: Artificial Sequence
<220> FEATURE:
<223> OTHER INFORMATION: 13B5-VL-CDR3 vaccine-derived NAb

<400> SEQUENCE: 128

Gln Asn Gly His Thr Phe Pro Pro Thr
1               5

<210> SEQ ID NO 129
<211> LENGTH: 116
<212> TYPE: PRT
<213> ORGANISM: Artificial Sequence
<220> FEATURE:
<223> OTHER INFORMATION: 18F10-VH vaccine-derived NAb

<400> SEQUENCE: 129

Gln Val Thr Leu Lys Glu Ser Gly Pro Gly Ile Leu Gln Pro Ser Gln
1               5                   10                  15
```

Thr Leu Ser Leu Thr Cys Ser Phe Ser Gly Phe Ser Leu Ser Thr Tyr
            20                  25                  30

Gly Ile Gly Ile Gly Trp Ile Arg Gln Pro Ser Gly Lys Gly Leu Glu
        35                  40                  45

Trp Leu Ala His Ile Trp Trp Asn Asp Asn Lys Asn Tyr Asn Thr Ala
50                      55                  60

Leu Lys Ser Arg Leu Thr Ile Ser Lys Asp Pro Ser Asn Asn Gln Val
65                  70                  75                  80

Phe Leu Lys Ile Ala Ser Val Asp Thr Ala Asp Thr Ala Thr Tyr Phe
                85                  90                  95

Cys Ala Arg Thr Gly Tyr Phe Asp Val Trp Gly Ala Gly Thr Thr Val
            100                 105                 110

Thr Val Ser Ser
        115

<210> SEQ ID NO 130
<211> LENGTH: 112
<212> TYPE: PRT
<213> ORGANISM: Artificial Sequence
<220> FEATURE:
<223> OTHER INFORMATION: 18F10-VL vaccine-derived NAb

<400> SEQUENCE: 130

Asp Val Val Leu Thr Gln Thr Pro Leu Ser Leu Pro Val Ser Leu Gly
1               5                   10                  15

Asp Gln Val Ser Ile Ser Cys Ser Ser Ser Gln Ser Leu Val His Ser
            20                  25                  30

Asn Gly Asn Thr Tyr Ile His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 131
<211> LENGTH: 10
<212> TYPE: PRT
<213> ORGANISM: Artificial Sequence
<220> FEATURE:
<223> OTHER INFORMATION: 18F10-VH-CDR1 vaccine-derived NAb

<400> SEQUENCE: 131

Gly Phe Ser Leu Ser Thr Tyr Gly Ile Gly
1               5                   10

<210> SEQ ID NO 132
<211> LENGTH: 7
<212> TYPE: PRT
<213> ORGANISM: Artificial Sequence
<220> FEATURE:
<223> OTHER INFORMATION: 18F10-VH-CDR2 vaccine-derived NAb

<400> SEQUENCE: 132

Ile Trp Trp Asn Asp Asn Lys
1               5

```
<210> SEQ ID NO 133
<211> LENGTH: 8
<212> TYPE: PRT
<213> ORGANISM: Artificial Sequence
<220> FEATURE:
<223> OTHER INFORMATION: 18F10-VH-CDR3 vaccine-derived NAb

<400> SEQUENCE: 133

Ala Arg Thr Gly Tyr Phe Asp Val
1               5

<210> SEQ ID NO 134
<211> LENGTH: 11
<212> TYPE: PRT
<213> ORGANISM: Artificial Sequence
<220> FEATURE:
<223> OTHER INFORMATION: 18F10-VL-CDR1 vaccine-derived NAb

<400> SEQUENCE: 134

Gln Ser Leu Val His Ser Asn Gly Asn Thr Tyr
1               5                   10

<210> SEQ ID NO 135
<211> LENGTH: 3
<212> TYPE: PRT
<213> ORGANISM: Artificial Sequence
<220> FEATURE:
<223> OTHER INFORMATION: 18F10-VL-CDR2 vaccine-derived NAb

<400> SEQUENCE: 135

Thr Val Ser
1

<210> SEQ ID NO 136
<211> LENGTH: 9
<212> TYPE: PRT
<213> ORGANISM: Artificial Sequence
<220> FEATURE:
<223> OTHER INFORMATION: 18F10-VL-CDR3 vaccine-derived NAb

<400> SEQUENCE: 136

Ser Gln Ser Thr His Val Pro Tyr Thr
1               5

<210> SEQ ID NO 137
<211> LENGTH: 121
<212> TYPE: PRT
<213> ORGANISM: Artificial Sequence
<220> FEATURE:
<223> OTHER INFORMATION: 21E9-VH vaccine-derived NAb

<400> SEQUENCE: 137

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ile Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95
```

Ala Arg Lys Gly Tyr Tyr Gly Ser Ser Gly Tyr Phe Asp Tyr Trp Gly
            100                 105                 110

Gln Gly Thr Thr Leu Thr Val Ser Ser
        115                 120

<210> SEQ ID NO 138
<211> LENGTH: 107
<212> TYPE: PRT
<213> ORGANISM: Artificial Sequence
<220> FEATURE:
<223> OTHER INFORMATION: 21E9-VL vaccine-derived NAb

<400> SEQUENCE: 138

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ser Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 139
<211> LENGTH: 8
<212> TYPE: PRT
<213> ORGANISM: Artificial Sequence
<220> FEATURE:
<223> OTHER INFORMATION: 21E9-VH-CDR1 vaccine-derived NAb

<400> SEQUENCE: 139

Gly Tyr Thr Phe Thr Ile Tyr Gly
1               5

<210> SEQ ID NO 140
<211> LENGTH: 8
<212> TYPE: PRT
<213> ORGANISM: Artificial Sequence
<220> FEATURE:
<223> OTHER INFORMATION: 21E9-VH-CDR2 vaccine-derived NAb

<400> SEQUENCE: 140

Ile Asn Thr Tyr Thr Gly Glu Pro
1               5

<210> SEQ ID NO 141
<211> LENGTH: 14
<212> TYPE: PRT
<213> ORGANISM: Artificial Sequence
<220> FEATURE:
<223> OTHER INFORMATION: 21E9-VH-CDR3 vaccine-derived NAb

<400> SEQUENCE: 141

Ala Arg Lys Gly Tyr Tyr Gly Ser Ser Gly Tyr Phe Asp Tyr
1               5                   10

<210> SEQ ID NO 142
<211> LENGTH: 6

```
<212> TYPE: PRT
<213> ORGANISM: Artificial Sequence
<220> FEATURE:
<223> OTHER INFORMATION: 21E9-VL-CDR1 vaccine-derived NAb

<400> SEQUENCE: 142

Gln Ser Val Ser Asn Asp
1               5

<210> SEQ ID NO 143
<211> LENGTH: 3
<212> TYPE: PRT
<213> ORGANISM: Artificial Sequence
<220> FEATURE:
<223> OTHER INFORMATION: 21E9-VL-CDR2 vaccine-derived NAb

<400> SEQUENCE: 143

Tyr Ala Ser
1

<210> SEQ ID NO 144
<211> LENGTH: 9
<212> TYPE: PRT
<213> ORGANISM: Artificial Sequence
<220> FEATURE:
<223> OTHER INFORMATION: 21E9-VL-CDR3 vaccine-derived NAb

<400> SEQUENCE: 144

Gln Gln Asp Tyr Ser Ser Pro Trp Thr
1               5

<210> SEQ ID NO 145
<211> LENGTH: 115
<212> TYPE: PRT
<213> ORGANISM: Artificial Sequence
<220> FEATURE:
<223> OTHER INFORMATION: 4A3-VH vaccine-derived NAb

<400> SEQUENCE: 145

Gln Val Gln Leu Gln Gln Pro Gly Pro Glu Leu Val Arg Pro Gly Ala
1               5                   10                  15

Ser Val Lys Leu Ser Cys Lys Ala Ser Gly Tyr Thr Phe Thr Ile Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Ser Gly Thr Gly Ala Tyr Trp Gly Gln Gly Thr Leu Leu Thr
            100                 105                 110

Val Ser Ala
        115

<210> SEQ ID NO 146
<211> LENGTH: 112
<212> TYPE: PRT
<213> ORGANISM: Artificial Sequence
<220> FEATURE:
<223> OTHER INFORMATION: 4A3-VL vaccine-derived NAb

<400> SEQUENCE: 146
```

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Leu Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110
```

<210> SEQ ID NO 147
<211> LENGTH: 8
<212> TYPE: PRT
<213> ORGANISM: Artificial Sequence
<220> FEATURE:
<223> OTHER INFORMATION: 4A3-VH-CDR1 vaccine-derived NAb

<400> SEQUENCE: 147

```
Gly Tyr Thr Phe Thr Ile Tyr Trp
1               5
```

<210> SEQ ID NO 148
<211> LENGTH: 8
<212> TYPE: PRT
<213> ORGANISM: Artificial Sequence
<220> FEATURE:
<223> OTHER INFORMATION: 4A3-VH-CDR2 vaccine-derived NAb

<400> SEQUENCE: 148

```
Ile Asp Pro Ser Asp Ser Glu Thr
1               5
```

<210> SEQ ID NO 149
<211> LENGTH: 8
<212> TYPE: PRT
<213> ORGANISM: Artificial Sequence
<220> FEATURE:
<223> OTHER INFORMATION: 4A3-VH-CDR3 vaccine-derived NAb

<400> SEQUENCE: 149

```
Ala Ser Ser Gly Thr Gly Ala Tyr
1               5
```

<210> SEQ ID NO 150
<211> LENGTH: 11
<212> TYPE: PRT
<213> ORGANISM: Artificial Sequence
<220> FEATURE:
<223> OTHER INFORMATION: 4A3-VL-CDR1 vaccine-derived NAb

<400> SEQUENCE: 150

```
Gln Ser Leu Leu Asp Ser Asp Gly Lys Thr Tyr
1               5                   10
```

<210> SEQ ID NO 151
<211> LENGTH: 3
<212> TYPE: PRT
<213> ORGANISM: Artificial Sequence

```
<220> FEATURE:
<223> OTHER INFORMATION: 4A3-VL-CDR2 vaccine-derived NAb

<400> SEQUENCE: 151

Leu Val Ser
1

<210> SEQ ID NO 152
<211> LENGTH: 9
<212> TYPE: PRT
<213> ORGANISM: Artificial Sequence
<220> FEATURE:
<223> OTHER INFORMATION: 4A3-VL-CDR3 vaccine-derived NAb

<400> SEQUENCE: 152

Trp Gln Gly Thr His Phe Pro Tyr Thr
1               5

<210> SEQ ID NO 153
<211> LENGTH: 116
<212> TYPE: PRT
<213> ORGANISM: Artificial Sequence
<220> FEATURE:
<223> OTHER INFORMATION: 62-11-VH vaccine-derived NAb

<400> SEQUENCE: 153

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Asn Gly Tyr Ser Ser Phe Ala Tyr Trp Gly Gln Gly Thr Leu Val
            100                 105                 110

Thr Val Ser Val
        115

<210> SEQ ID NO 154
<211> LENGTH: 107
<212> TYPE: PRT
<213> ORGANISM: Artificial Sequence
<220> FEATURE:
<223> OTHER INFORMATION: 62-11-VL vaccine-derived NAb

<400> SEQUENCE: 154

Asp Val Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Asp Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80
```

-continued

Glu Asp Ile Ala Thr Tyr Tyr Cys Gln Gln Tyr Ser Lys Leu Pro Tyr
            85                  90                  95

Thr Phe Gly Gly Gly Thr Lys Leu Glu Ile Lys
            100                 105

<210> SEQ ID NO 155
<211> LENGTH: 8
<212> TYPE: PRT
<213> ORGANISM: Artificial Sequence
<220> FEATURE:
<223> OTHER INFORMATION: 62-11-VH-CDR1 vaccine-derived NAb

<400> SEQUENCE: 155

Gly Tyr Thr Phe Thr Ser Tyr Trp
1               5

<210> SEQ ID NO 156
<211> LENGTH: 8
<212> TYPE: PRT
<213> ORGANISM: Artificial Sequence
<220> FEATURE:
<223> OTHER INFORMATION: 62-11-VH-CDR2 vaccine-derived NAb

<400> SEQUENCE: 156

Ile Asp Pro Ser Asp Ser Glu Thr
1               5

<210> SEQ ID NO 157
<211> LENGTH: 9
<212> TYPE: PRT
<213> ORGANISM: Artificial Sequence
<220> FEATURE:
<223> OTHER INFORMATION: 62-11-VH-CDR3 vaccine-derived NAb

<400> SEQUENCE: 157

Ser Asn Gly Tyr Ser Ser Phe Ala Tyr
1               5

<210> SEQ ID NO 158
<211> LENGTH: 6
<212> TYPE: PRT
<213> ORGANISM: Artificial Sequence
<220> FEATURE:
<223> OTHER INFORMATION: 62-11-VL-CDR1 vaccine-derived NAb

<400> SEQUENCE: 158

Gln Gly Ile Ser Asn Tyr
1               5

<210> SEQ ID NO 159
<211> LENGTH: 3
<212> TYPE: PRT
<213> ORGANISM: Artificial Sequence
<220> FEATURE:
<223> OTHER INFORMATION: 62-11-VL-CDR2 vaccine-derived NAb

<400> SEQUENCE: 159

Asp Thr Ser
1

<210> SEQ ID NO 160
<211> LENGTH: 9
<212> TYPE: PRT
<213> ORGANISM: Artificial Sequence
<220> FEATURE:
<223> OTHER INFORMATION: 62-11-VL-CDR3 vaccine-derived NAb

<400> SEQUENCE: 160

Gln Gln Tyr Ser Lys Leu Pro Tyr Thr
1               5

<210> SEQ ID NO 161
<211> LENGTH: 116
<212> TYPE: PRT
<213> ORGANISM: Artificial Sequence
<220> FEATURE:
<223> OTHER INFORMATION: 62-100-VH vaccine-derived NAb

<400> SEQUENCE: 161

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Met Asn Trp Val Lys Gln Arg Pro Gly Gln Gly Leu Glu Trp Ile
            35                  40                  45

Gly Met Ile Asp Pro Ser Asp Ser Glu Thr His Tyr Asn Gln Met Phe
        50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Asn Gly Tyr Ser Ser Phe Ala Tyr Trp Gly Gln Gly Thr Leu Val
            100                 105                 110

Thr Val Ser Val
        115

<210> SEQ ID NO 162
<211> LENGTH: 107
<212> TYPE: PRT
<213> ORGANISM: Artificial Sequence
<220> FEATURE:
<223> OTHER INFORMATION: 62-100-VL vaccine-derived NAb

<400> SEQUENCE: 162

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
65                  70                  75                  80

Glu Asp Phe Gly Lys Tyr Val Cys Gln Gln Ser Asn Ser Trp Pro Leu
                85                  90                  95

Thr Phe Gly Ser Gly Thr Lys Leu Glu Ile Lys
            100                 105

<210> SEQ ID NO 163
<211> LENGTH: 8
<212> TYPE: PRT
<213> ORGANISM: Artificial Sequence
<220> FEATURE:
<223> OTHER INFORMATION: 62-100-VH-CDR1 vaccine-derived NAb

```
<400> SEQUENCE: 163

Gly Tyr Thr Phe Thr Ser Tyr Trp
1               5

<210> SEQ ID NO 164
<211> LENGTH: 8
<212> TYPE: PRT
<213> ORGANISM: Artificial Sequence
<220> FEATURE:
<223> OTHER INFORMATION: 62-100-VH-CDR2 vaccine-derived NAb

<400> SEQUENCE: 164

Ile Asp Pro Ser Asp Ser Glu Thr
1               5

<210> SEQ ID NO 165
<211> LENGTH: 9
<212> TYPE: PRT
<213> ORGANISM: Artificial Sequence
<220> FEATURE:
<223> OTHER INFORMATION: 62-100-VH-CDR3 vaccine-derived NAb

<400> SEQUENCE: 165

Ser Asn Gly Tyr Ser Ser Phe Ala Tyr
1               5

<210> SEQ ID NO 166
<211> LENGTH: 6
<212> TYPE: PRT
<213> ORGANISM: Artificial Sequence
<220> FEATURE:
<223> OTHER INFORMATION: 62-100-VL-CDR1 vaccine-derived NAb

<400> SEQUENCE: 166

Gln Ser Ile Ser Asn Asn
1               5

<210> SEQ ID NO 167
<211> LENGTH: 3
<212> TYPE: PRT
<213> ORGANISM: Artificial Sequence
<220> FEATURE:
<223> OTHER INFORMATION: 62-100-VL-CDR2 vaccine-derived NAb

<400> SEQUENCE: 167

Tyr Ala Ser
1

<210> SEQ ID NO 168
<211> LENGTH: 9
<212> TYPE: PRT
<213> ORGANISM: Artificial Sequence
<220> FEATURE:
<223> OTHER INFORMATION: 62-100-VL-CDR3 vaccine-derived NAb

<400> SEQUENCE: 168

Gln Gln Ser Asn Ser Trp Pro Leu Thr
1               5

<210> SEQ ID NO 169
<211> LENGTH: 119
<212> TYPE: PRT
<213> ORGANISM: Artificial Sequence
<220> FEATURE:
<223> OTHER INFORMATION: 2-80-VH vaccine-derived NAb

<400> SEQUENCE: 169
```

-continued

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Glu Asp Thr Ala Thr Tyr Phe Cys
                85                  90                  95

Ala Arg Arg Gly Asp Gly Leu Tyr Ser Met Asp Tyr Trp Gly Gln Gly
            100                 105                 110

Thr Ser Val Thr Val Ser Ser
        115

<210> SEQ ID NO 170
<211> LENGTH: 111
<212> TYPE: PRT
<213> ORGANISM: Artificial Sequence
<220> FEATURE:
<223> OTHER INFORMATION: 2-80-VL vaccine-derived NAb

<400> SEQUENCE: 170

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Ile Asp Ser Tyr
            20                  25                  30

Gly Asn Ser Phe Met Tyr Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Leu Thr Phe Gly Ala Gly Thr Lys Leu Glu Leu Lys
            100                 105                 110

<210> SEQ ID NO 171
<211> LENGTH: 8
<212> TYPE: PRT
<213> ORGANISM: Artificial Sequence
<220> FEATURE:
<223> OTHER INFORMATION: 2-80-VH-CDR1 vaccine-derived NAb

<400> SEQUENCE: 171

Gly Tyr Thr Phe Thr Asn Phe Gly
1               5

<210> SEQ ID NO 172
<211> LENGTH: 8
<212> TYPE: PRT
<213> ORGANISM: Artificial Sequence
<220> FEATURE:
<223> OTHER INFORMATION: 2-80-VH-CDR2 vaccine-derived NAb

<400> SEQUENCE: 172

```
Ile Asn Thr Tyr Thr Gly Glu Pro
1               5

<210> SEQ ID NO 173
<211> LENGTH: 12
<212> TYPE: PRT
<213> ORGANISM: Artificial Sequence
<220> FEATURE:
<223> OTHER INFORMATION: 2-80-VH-CDR3 vaccine-derived NAb

<400> SEQUENCE: 173

Ala Arg Arg Gly Asp Gly Leu Tyr Ser Met Asp Tyr
1               5                   10

<210> SEQ ID NO 174
<211> LENGTH: 10
<212> TYPE: PRT
<213> ORGANISM: Artificial Sequence
<220> FEATURE:
<223> OTHER INFORMATION: 2-80-VL-CDR1 vaccine-derived NAb

<400> SEQUENCE: 174

Glu Ser Ile Asp Ser Tyr Gly Asn Ser Phe
1               5                   10

<210> SEQ ID NO 175
<211> LENGTH: 3
<212> TYPE: PRT
<213> ORGANISM: Artificial Sequence
<220> FEATURE:
<223> OTHER INFORMATION: 2-80-VL-CDR2 vaccine-derived NAb

<400> SEQUENCE: 175

Arg Ala Ser
1

<210> SEQ ID NO 176
<211> LENGTH: 9
<212> TYPE: PRT
<213> ORGANISM: Artificial Sequence
<220> FEATURE:
<223> OTHER INFORMATION: 2-80-VL-CDR3 vaccine-derived NAb

<400> SEQUENCE: 176

Gln Gln Ser Asn Glu Asp Pro Leu Thr
1               5

<210> SEQ ID NO 177
<211> LENGTH: 13
<212> TYPE: PRT
<213> ORGANISM: Artificial Sequence
<220> FEATURE:
<223> OTHER INFORMATION: K13M peptide

<400> SEQUENCE: 177

Lys Arg Leu Asp Val Cys Arg Ala Lys Met Gly Tyr Met
1               5                   10

<210> SEQ ID NO 178
<211> LENGTH: 14
<212> TYPE: PRT
<213> ORGANISM: Artificial Sequence
<220> FEATURE:
<223> OTHER INFORMATION: H14M peptide

<400> SEQUENCE: 178

His Lys Arg Leu Asp Val Cys Arg Ala Lys Met Gly Tyr Met
```

```
<210> SEQ ID NO 179
<211> LENGTH: 15
<212> TYPE: PRT
<213> ORGANISM: Artificial Sequence
<220> FEATURE:
<223> OTHER INFORMATION: K15M peptide

<400> SEQUENCE: 179

Lys His Lys Arg Leu Asp Val Cys Arg Ala Lys Met Gly Tyr Met
1               5                   10                  15

<210> SEQ ID NO 180
<211> LENGTH: 14
<212> TYPE: PRT
<213> ORGANISM: Artificial Sequence
<220> FEATURE:
<223> OTHER INFORMATION: K14CS peptide

<400> SEQUENCE: 180

Lys Arg Leu Asp Val Ser Arg Ala Lys Met Gly Tyr Met Cys
1               5                   10

<210> SEQ ID NO 181
<211> LENGTH: 16
<212> TYPE: PRT
<213> ORGANISM: Artificial Sequence
<220> FEATURE:
<223> OTHER INFORMATION: non-native sequence

<400> SEQUENCE: 181

Lys His Lys Arg Leu Asp Val Ser Arg Ala Lys Met Gly Tyr Met Cys
1               5                   10                  15

<210> SEQ ID NO 182
<211> LENGTH: 13
<212> TYPE: PRT
<213> ORGANISM: Artificial Sequence
<220> FEATURE:
<223> OTHER INFORMATION: K13MS peptide

<400> SEQUENCE: 182

Lys Arg Leu Asp Val Ser Arg Ala Lys Met Gly Tyr Met
1               5                   10

<210> SEQ ID NO 183
<211> LENGTH: 25
<212> TYPE: DNA
<213> ORGANISM: Artificial Sequence
<220> FEATURE:
<223> OTHER INFORMATION: reverse primer

<400> SEQUENCE: 183
tggatggtgg gaagatggat acagt                                    25

<210> SEQ ID NO 184
<211> LENGTH: 10
<212> TYPE: PRT
<213> ORGANISM: Artificial Sequence
<220> FEATURE:
<223> OTHER INFORMATION: L10L TB40 specific peptide

<400> SEQUENCE: 184

Leu Asp Pro His Ala Phe His Leu Leu Leu
1               5                   10
```

<210> SEQ ID NO 185
<211> LENGTH: 9
<212> TYPE: PRT
<213> ORGANISM: Artificial Sequence
<220> FEATURE:
<223> OTHER INFORMATION: L9L Towne specific peptide

<400> SEQUENCE: 185

Leu Asp Lys Ala Phe His Leu Leu Leu
1               5

<210> SEQ ID NO 186
<211> LENGTH: 15
<212> TYPE: PRT
<213> ORGANISM: Artificial Sequence
<220> FEATURE:
<223> OTHER INFORMATION: N-terminal truncated peptide

<400> SEQUENCE: 186

Lys Arg Leu Asp Val Cys Arg Ala Lys Met Gly Tyr Met Leu Gln
1               5                   10                  15

<210> SEQ ID NO 187
<211> LENGTH: 14
<212> TYPE: PRT
<213> ORGANISM: Artificial Sequence
<220> FEATURE:
<223> OTHER INFORMATION: N-terminal truncated peptide

<400> SEQUENCE: 187

Arg Leu Asp Val Cys Arg Ala Lys Met Gly Tyr Met Leu Gln
1               5                   10

<210> SEQ ID NO 188
<211> LENGTH: 13
<212> TYPE: PRT
<213> ORGANISM: Artificial Sequence
<220> FEATURE:
<223> OTHER INFORMATION: N-terminal truncated peptide

<400> SEQUENCE: 188

Leu Asp Val Cys Arg Ala Lys Met Gly Tyr Met Leu Gln
1               5                   10

<210> SEQ ID NO 189
<211> LENGTH: 12
<212> TYPE: PRT
<213> ORGANISM: Artificial Sequence
<220> FEATURE:
<223> OTHER INFORMATION: N-terminal truncated peptide

<400> SEQUENCE: 189

Asp Val Cys Arg Ala Lys Met Gly Tyr Met Leu Gln
1               5                   10

<210> SEQ ID NO 190
<211> LENGTH: 11
<212> TYPE: PRT
<213> ORGANISM: Artificial Sequence
<220> FEATURE:
<223> OTHER INFORMATION: N-terminal truncated peptide

<400> SEQUENCE: 190

Val Cys Arg Ala Lys Met Gly Tyr Met Leu Gln
1               5                   10

```
<210> SEQ ID NO 191
<211> LENGTH: 10
<212> TYPE: PRT
<213> ORGANISM: Artificial Sequence
<220> FEATURE:
<223> OTHER INFORMATION: N-terminal truncated peptide

<400> SEQUENCE: 191

Cys Arg Ala Lys Met Gly Tyr Met Leu Gln
1               5                   10

<210> SEQ ID NO 192
<211> LENGTH: 9
<212> TYPE: PRT
<213> ORGANISM: Artificial Sequence
<220> FEATURE:
<223> OTHER INFORMATION: N-terminal truncated peptide

<400> SEQUENCE: 192

Arg Ala Lys Met Gly Tyr Met Leu Gln
1               5

<210> SEQ ID NO 193
<211> LENGTH: 8
<212> TYPE: PRT
<213> ORGANISM: Artificial Sequence
<220> FEATURE:
<223> OTHER INFORMATION: N-terminal truncated peptide

<400> SEQUENCE: 193

Ala Lys Met Gly Tyr Met Leu Gln
1               5

<210> SEQ ID NO 194
<211> LENGTH: 7
<212> TYPE: PRT
<213> ORGANISM: Artificial Sequence
<220> FEATURE:
<223> OTHER INFORMATION: N-terminal truncated peptide

<400> SEQUENCE: 194

Lys Met Gly Tyr Met Leu Gln
1               5

<210> SEQ ID NO 195
<211> LENGTH: 6
<212> TYPE: PRT
<213> ORGANISM: Artificial Sequence
<220> FEATURE:
<223> OTHER INFORMATION: N-terminal truncated peptide

<400> SEQUENCE: 195

Met Gly Tyr Met Leu Gln
1               5

<210> SEQ ID NO 196
<211> LENGTH: 14
<212> TYPE: PRT
<213> ORGANISM: Artificial Sequence
<220> FEATURE:
<223> OTHER INFORMATION: C-terminal truncated peptide

<400> SEQUENCE: 196

Lys Arg Leu Asp Val Cys Arg Ala Lys Met Gly Tyr Met Leu
1               5                   10

<210> SEQ ID NO 197
```

```
<211> LENGTH: 12
<212> TYPE: PRT
<213> ORGANISM: Artificial Sequence
<220> FEATURE:
<223> OTHER INFORMATION: C-terminal truncated peptide

<400> SEQUENCE: 197

Lys Arg Leu Asp Val Cys Arg Ala Lys Met Gly Tyr
1               5                   10

<210> SEQ ID NO 198
<211> LENGTH: 11
<212> TYPE: PRT
<213> ORGANISM: Artificial Sequence
<220> FEATURE:
<223> OTHER INFORMATION: C-terminal truncated peptide

<400> SEQUENCE: 198

Lys Arg Leu Asp Val Cys Arg Ala Lys Met Gly
1               5                   10

<210> SEQ ID NO 199
<211> LENGTH: 10
<212> TYPE: PRT
<213> ORGANISM: Artificial Sequence
<220> FEATURE:
<223> OTHER INFORMATION: C-terminal truncated peptide

<400> SEQUENCE: 199

Lys Arg Leu Asp Val Cys Arg Ala Lys Met
1               5                   10

<210> SEQ ID NO 200
<211> LENGTH: 9
<212> TYPE: PRT
<213> ORGANISM: Artificial Sequence
<220> FEATURE:
<223> OTHER INFORMATION: C-terminal truncated peptide

<400> SEQUENCE: 200

Lys Arg Leu Asp Val Cys Arg Ala Lys
1               5

<210> SEQ ID NO 201
<211> LENGTH: 8
<212> TYPE: PRT
<213> ORGANISM: Artificial Sequence
<220> FEATURE:
<223> OTHER INFORMATION: C-terminal truncated peptide

<400> SEQUENCE: 201

Lys Arg Leu Asp Val Cys Arg Ala
1               5

<210> SEQ ID NO 202
<211> LENGTH: 7
<212> TYPE: PRT
<213> ORGANISM: Artificial Sequence
<220> FEATURE:
<223> OTHER INFORMATION: C-terminal truncated peptide

<400> SEQUENCE: 202

Lys Arg Leu Asp Val Cys Arg
1               5

<210> SEQ ID NO 203
<211> LENGTH: 6
```

```
<212> TYPE: PRT
<213> ORGANISM: Artificial Sequence
<220> FEATURE:
<223> OTHER INFORMATION: C-terminal truncated peptide

<400> SEQUENCE: 203

Lys Arg Leu Asp Val Cys
1               5

<210> SEQ ID NO 204
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 204

Ala Arg Leu Asp Val Cys Arg Ala Lys Met Gly Tyr Met
1               5                   10

<210> SEQ ID NO 205
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 205

Lys Ala Leu Asp Val Cys Arg Ala Lys Met Gly Tyr Met
1               5                   10

<210> SEQ ID NO 206
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 206

Lys Arg Ala Asp Val Cys Arg Ala Lys Met Gly Tyr Met
1               5                   10

<210> SEQ ID NO 207
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 207

Lys Arg Leu Ala Val Cys Arg Ala Lys Met Gly Tyr Met
1               5                   10

<210> SEQ ID NO 208
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 208

Lys Arg Leu Asp Ala Cys Arg Ala Lys Met Gly Tyr Met
1               5                   10

<210> SEQ ID NO 209
<211> LENGTH: 13
<212> TYPE: PRT
```

<213> ORGANISM: Artificial Sequence
<220> FEATURE:
<223> OTHER INFORMATION: K13M peptide alanine scan

<400> SEQUENCE: 209

Lys Arg Leu Asp Val Ala Arg Ala Lys Met Gly Tyr Met
1               5                   10

<210> SEQ ID NO 210
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 210

Lys Arg Leu Asp Val Cys Ala Ala Lys Met Gly Tyr Met
1               5                   10

<210> SEQ ID NO 211
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 211

Lys Arg Leu Asp Val Cys Arg Ala Ala Met Gly Tyr Met
1               5                   10

<210> SEQ ID NO 212
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 212

Lys Arg Leu Asp Val Cys Arg Ala Lys Ala Gly Tyr Met
1               5                   10

<210> SEQ ID NO 213
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 213

Lys Arg Leu Asp Val Cys Arg Ala Lys Met Ala Tyr Met
1               5                   10

<210> SEQ ID NO 214
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 214

Lys Arg Leu Asp Val Cys Arg Ala Lys Met Gly Ala Met
1               5                   10

<210> SEQ ID NO 215
<211> LENGTH: 13
<212> TYPE: PRT
<213> ORGANISM: Artificial Sequence
<220> FEATURE:
<223> OTHER INFORMATION: K13M peptide alanine scan

<400> SEQUENCE: 215

Lys Arg Leu Asp Val Cys Arg Ala Lys Met Gly Tyr Ala
1               5                   10